# United States Patent [19]

Grollier et al.

[11] 4,240,450

[45] Dec. 23, 1980

[54] COMPOSITION AND PROCESS FOR THE TREATMENT OF KERATIN MATERIALS WITH POLYMERS

[75] Inventors: Jean-Francois Grollier; Claire Fiquet; Chantal Fourcadier, all of Paris; Claude Dubief, Versailles; Daniele Cauwet, Crosne, all of France

[73] Assignee: L'Oreal, Paris, France

[21] Appl. No.: 886,554

[22] Filed: Mar. 14, 1978

[30] Foreign Application Priority Data

Mar. 15, 1977 [LU] Luxembourg .......................... 76955

[51] Int. Cl.$^3$ .................. A45D 7/00; A61K 7/08; A61K 7/11; A61K 7/13

[52] U.S. Cl. .......................................... 132/7; 8/404; 8/406; 424/DIG. 1; 424/DIG. 2; 424/47; 424/61; 424/70; 424/71; 424/72; 424/73; 424/18; 424/81

[58] Field of Search ............... 424/DIG. 1, DIG. 2, 424/47, 70, 71, 61, 72, 73, 78, 81; 8/10.1, 10.2, 10, 11, 32; 132/7

[56] References Cited

U.S. PATENT DOCUMENTS

| | | | |
|---|---|---|---|
| 2,047,398 | 7/1936 | Voss et al. ............................. 260/2 |
| 2,182,306 | 12/1939 | Ulrich et al. ........................... 260/2 |
| 2,261,002 | 10/1941 | Ritter .................................... 260/570 |
| 2,271,378 | 1/1942 | Searle .................................... 424/329 |
| 2,273,780 | 2/1942 | Dittmar ................................. 260/28 |
| 2,375,853 | 5/1945 | Kirby et al. ........................... 260/583 |
| 2,388,614 | 11/1945 | Kirby et al. ........................... 424/329 |
| 2,454,547 | 11/1948 | Bock et al. ........................... 260/567.6 |
| 2,723,248 | 11/1955 | Wright ................................... 424/47 |
| 2,926,161 | 2/1960 | Butler et al. .......................... 260/89.7 |
| 2,961,347 | 11/1960 | Floyd .................................... 8/128 X |
| 3,206,462 | 9/1965 | McCarty ............................... 260/256.4 |
| 3,227,615 | 1/1966 | Korden ................................. 424/71 |
| 3,288,770 | 11/1966 | Butler ................................... 260/88.3 |
| 3,372,149 | 3/1968 | Fertig et al. .......................... 260/78.4 |
| 3,874,870 | 4/1975 | Green et al. .......................... 424/329 X |
| 3,917,817 | 11/1975 | Vanlerberghe et al. ............... 424/70 |
| 3,928,224 | 12/1975 | Vanlerberghe et al. ............... 252/172 |
| 3,929,990 | 12/1975 | Green et al. .......................... 424/78 |
| 3,958,581 | 5/1976 | Abegg et al. ......................... 132/7 |
| 3,966,398 | 6/1976 | Vanlerberghe et al. ............... 8/11 |
| 3,966,404 | 6/1976 | Papantoniou et al. ............... 8/127.51 |
| 3,966,904 | 6/1976 | Green et al. .......................... 424/78 |
| 3,972,336 | 8/1976 | Nowak et al. ........................ 132/7 |
| 4,001,432 | 1/1977 | Green et al. .......................... 424/329 |
| 4,005,193 | 1/1977 | Green et al. .......................... 424/168 |
| 4,013,787 | 3/1977 | Vanlerberghe et al. ............... 424/70 |
| 4,025,617 | 5/1977 | Green et al. .......................... 424/78 |
| 4,025,627 | 5/1977 | Green et al. .......................... 424/248.4 |
| 4,025,653 | 5/1977 | Green et al. .......................... 424/325 |
| 4,026,945 | 5/1977 | Green et al. .......................... 260/567.6 P |
| 4,027,020 | 5/1977 | Green et al. .......................... 424/248.56 |

FOREIGN PATENT DOCUMENTS

| | | | |
|---|---|---|---|
| 2184890 | 12/1973 | France ................................... 424/71 |
| 2270846 | 12/1975 | France ................................... 424/71 |
| 2280361 | 2/1976 | France ................................... 424/71 |
| 2316271 | 1/1977 | France ................................... 424/71 |

*Primary Examiner*—Natalie Trousof
*Assistant Examiner*—Vera C. Clarke
*Attorney, Agent, or Firm*—Fleit & Jacobson

[57] ABSTRACT

New compositions for the treatment of keratin material, in particular human hair, skin and nails are provided comprising a combination of a cationic polymer with an anionic polymer. Surprisingly the anionic polymer can be retained well on the hair, even after rinsing, when applied with the cationic polymer.

29 Claims, No Drawings`

COMPOSITION AND PROCESS FOR THE TREATMENT OF KERATIN MATERIALS WITH POLYMERS

The present invention relates to compositions based on polymers which are for use in the treatment of keratin materials, in particular hair as well as skin and the nails.

In general it is desired to obtain, for example during treatment of keratin fibres, in particular hair, easy combing out, an agreeable feel and a suppleness for the wet hair, which must, moreover, be simple to set in waves and be non-sticky.

For dry hair, the treatments are intended to make the hair glossy, easy to style, free from electrostatic charge, springy, soft to the touch and non-sticky, hold well, such that it does not rapidly become greasy again and such that volume is given to the head of hair.

Numerous compositions containing either anionic polymers or cationic polymers are known. In sofar as they contribute certain desired properties, especially cosmetic properties to the hair, these compositions nevertheless do not enable all of the qualities sought to be obtained at the same time.

The same holds true in respect of the treatment of the skin with polymer compositions where it is sought to avoid the covering being slippery or sticky, or in the treatment of the nails where the film must be glossy and hard whilst retaining good suppleness preventing splitting under the mechanical strains to which the nails are subjected.

Amongst these different polymers, anionic polymers are known which provide certain properties such as the strengthening of the keratin fibre and the hold of the head of hair. Moreover, such polymers have valuable gloss characteristics, which are desirable in the treatment of keratin materials.

The anionic polymers, however, have the disadvantage that they fix poorly to keratin materials. Thus, when they are applied to hair in compositions which are not intended to be rinsed out, such as setting lotions, lacquers or restructuring lotions, powdering resulting from too great a friability and poor substantivity is frequently found.

These anionic polymers, although recommended, cannot, moreover, be used efficiently in compositions intended to be rinsed out, such as shampoos, nor in lotions termed rinses, which are used to produce a conditioning effect on the hair, or in treatment creams applied before or after colouring, bleaching, shampooing or permanent waving. As is well known, these polymers are in fact to a large extent removed during washing.

An object of the present invention is to provide compositions which enable one to fix anionic polymers to keratin materials in significant amounts, even when the compositions are intended to be rinsed off.

Cationic polymers are well known in the art for their substantivity, which is the more significant as the cationic character is more pronounced, and which enables them to become fixed and to remain on, especially, hair. When they are used on hair, these polymers facilitate combing out of the hair and impart to the hair softness and suppleness.

However, the use of these polymers on their own does not enable all of the cosmetic properties sought to be imparted to keratin materials, such as to hair, to nails and to the skin.

Thus, when they are used in compositions for treatment of the skin, they have the disadvantage of rendering the skin slippery and sticky; when they are used in the treatment of hair the hair frequently lacks hold; when they are used in the treatment of the nails, the coating is often too pliable.

We have found, surprisingly, according to the present invention, that the anchoring of anionic polymers to keratin material is possible if these polymers are used in combination with cationic polymers.

This anchoring of anionic polymers to keratin material by means of a cationic polymer is due, essentially, to an interaction between these two types of polymers. Although the precise nature of this interaction may not be known perfectly, it is assumed that, in certain cases, a complex is formed which can be redissolved subsequently if precipitation should occur.

Moreover, this interaction makes it possible to obtain results inherent in the product resulting therefrom.

Accordingly the present invention provides a composition, intended to be used in the treatment of keratin materials, containing at least one anionic polymer and at least one cationic polymer and, in general, a solvent medium.

The compositions according to the invention are, in general, intended to be used for cosmetic purposes. They can be employed, especially, in the treatment of hair, nails and the skin.

Thus, the use of a combination of a cationic polymer with an anionic polymer in wavesetting lotions and restructuring lotions for the hair has enabled a perceptible reduction in powdering to be found.

When it is applied to nails, the combination leads, surprisingly, to strengthening of the nails.

Skin treated with lotions of the "after shave" or "toilet water" type remains smooth and supple.

The most surprising result is obtained, however, with compositions intended to be rinsed out.

It is possible, directly after shampooing with a shampoo containing the combination according to the invention, to give the hair a waveset having a good long term hold. Hair treated with these shampoos as well as with lotions termed "rinses", treatment creams and also any composition the application of which is usually followed by rinsing, has a good long term hold, volume and gloss and reduced static electricity.

It is found, moreover, that skin treated with a composition intended to be rinsed, such as a shaving foam, remains supple and smooth.

When during treatment of the hair, it is desired to obtain a good hold, particularly valuable results can be obtained when a combination of anionic polymer and strongly or moderately substantive cationic polymer, such as those containing a large number of tertiary or quaternary amino structural units, is used; when it is desired to obtain a head of hair which is soft and supple and has volume and reduced static electricity, valuable results can be obtained when cationic polymers are combined with anionic polymers derived from a carboxylic acid and, in particular, those derived from acrylic or methacrylic acid, from crotonic acid containing at least one recurring unit other than from vinyl acetate, or from maleic anhydride.

The combination gives advantageous results when it is used together with a surface-active agent. This surface-active agent can act as an agent transferring the combination to the keratin material and, in certain cases, as a solubilizing agent for the precipitate which can form with certain combinations of cationic and anionic polymers.

Valuable results are obtained, especially by combining the most substantive cationic polymer with a surface-active agent which is weakly anionic but which suffices to solubilise the combination, in the latter precipitates thereby to bring the maximum amount of anionic polymers onto the hair and to obtain a good hold.

Preferably, non-ionic to weakly anionic surface-active agents are used in combination with moderately substantive cationic polymers, of the polyamino-amide or polyalkylene-amine type, and anionic polymers, and strongly anionic surface-active agents are used with highly substantive cationic polymers, of the cyclopolymer or quaternary ammonium type, and anionic polymers.

If a precipitate forms during mixing of the anionic polymer and the cationic polymer, it is possible to use cosmetically acceptable solvents, in addition to or in place of the surface-active agent, or to redissolve the complex by adding an excess either of the anionic polymer or of the cationic polymer.

Finally, it is possible to change the pH of the composition with a view to obtaining the latter in solution. It is thus possible to prepare and to apply the composition according to the invention to the keratin material at a pH at which the combination is soluble in an aqueous medium and then to apply a second composition to obtain a pH on the keratin material which gives rise to maximum deposition and, in particular, to precipitation of the combination on the keratin material.

A further possibility involves preparing the composition under pH conditions at which the combination is soluble, lyophilizing this combination and preparing the composition just before application to the keratin material by dissolving it in the appropriate medium.

Again, the combination according to the invention can form on the keratin material, such as hair, and this can be of value when the polymers have a tendency to precipitate under the usual conditions for application of the composition. It is thus possible successively to apply a lotion or a shampoo containing the cationic polymer and then a shampoo containing an anionic polymer, which treatment can include, if necessary, an intermediate rinsing stage, or to effect permanent waving using a cationic polymer in the first reducing, composition and the anionic polymer with the fixing agent for the permanent wave in the second composition. This procedure, carried out in two stages, likewise makes it possible to work under different pH conditions, which can be adjusted so as to give conditions under which each polymer is soluble and to obtain, during mixing, a pH which results in good deposition of the combination according to the invention on the keratin material.

The anionic polymers used in the combination according to the invention generally have a molecular weight of 500 to 5 million and advantageously of 10,000 to 3 million.

The cationic polymers used in the combination according to the invention generally have a molecular weight of 500 to 2 or 5 million.

The cationic polymers which can be used in the present invention generally contain primary, secondary, tertiary or quaternary amino groups.

The anionic polymers which can be used in the invention generally possess sulphonic, carboxylic or phosphoric acid groupings.

The compositions usually have a pH from 2 to 11 and preferably from 4 to 10 and can be in the form of aqueous or aqueous-alcoholic solutions, gels, emulsions, creams, milk or dispersions.

The solvent medium can consist of water or any other organic or inorganic cosmetically acceptable solvent, or a mixture thereof.

Amongst the cationic polymers which can be used according to the invention, the following may be mentioned:

(1) Quaternary derivatives of cellulose ethers, described in French Pat. No. 1,492,597, the disclosure of which is hereby incorporated by reference, corresponding to the structural formula:

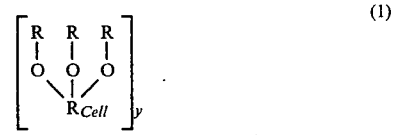

wherein $R_{Cell}$ is the radical of an anhydroglucose unit, y is a number having a value of, say, 50 to 20,000 and each R individually represents a substituent which is a group of the general formula:

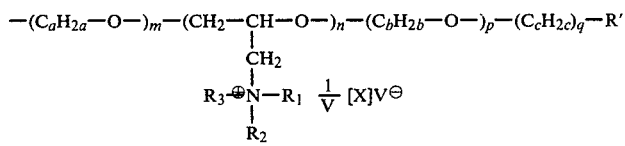

wherein a is an integer having a value of 2 or 3; b is an integer having a value of 2 or 3; c is an integer having a value of 1 to 3; m is 0 or an integer having a value of 1 to 10; n is 0 or an integer having a value of 1 to 3; p is 0 or an integer having a value of 1 to 10; q is 0 or 1; R' is a radical of the formula

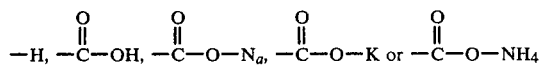

provided that R' represents -H when q is zero; $R_1$, $R_2$ and $R_3$, taken individually, each represent an alkyl, aryl, aralkyl, alkaryl, cycloalkyl, alkoxyalkyl or alkoxyaryl radical, containing up to 10 carbon atoms, provided that when the radical is an alkoxyalkyl radical there are at least 2 carbon atoms separating the oxygen atom from the nitrogen atom and also provided that the total number of carbon atoms present in the radicals represented by $R_1$, $R_2$ and $R_3$ is from 3 to 12; or $R_1$, $R_2$ and $R_3$, taken together, can, together with the nitrogen atom to which they are linked, represent one of the following radicals: pyridine, α-methylpyridine, 3,5-di-methylpyridine, 2,4,6-trimethylpyridine, N-methylpiperidine, N-ethylpiperidine, N-methyl-morpholine or N-ethyl-morpholine; X is an anion and V is an integer equal to the valency of X; and the mean value of n per anhydroglucose unit of this cellulose ether is from 0.01 to 1, and the mean value of (m+n+p+q) per anhydroglucose unit of this cellulose ether is from about 0.01 to 4.

The most particularly preferred polymers are those corresponding to the formula (1) given above in which a and b are 2, q is 0, m, n and p have the values given above, R' denotes hydrogen and $R_1$, $R_2$ and $R_3$ denote methyl. The mean values per anhydroglucose unit are from 0.35 to 0.45 for n and 1 to 2 for the sum of m+p and X denotes chloride.

The preferred ethers used in the invention have viscosities at 25° C. of 50 to 35,000 centipoise as 2% strength by weight aqueous solutions, measured by the ASTM method D-2364-65 (model LVF Brookfield viscometer, 30 revolutions/minute, spindle No. 2) and those which are particularly preferred are those products of Messrs. Union Carbide Corporation which have the trademarks "JR-125", "JR-400" and "JR-30M", which designate a polymer of the type described above having a viscosity of 125 centipoise, 400 centipoise and 30,000 centipoise respectively.

(2) Polymers which are soluble in water and have a molecular weight of 20,000 to 3,000,000, chosen from amongst the homopolymers and copolymers given below, the homopolymers containing, as the main constituent of the chain, units corresponding to formula (2) or (2'):

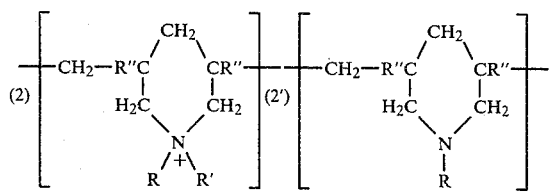

in which R" denotes hydrogen or methyl and R and R' independently of one another denote an alkyl group having 1 to 22 carbon atoms, a hydroxyalkyl group in which the alkyl group preferably has 1 to 5 carbon atoms or a lower amidoalkyl group, and wherein R and R' can denote, together with the nitrogen atom to which they are linked, heterocyclic groups such as piperidinyl or morpholinyl, associated with a cosmetically acceptable anion.

The copolymers can be copolymers of acrylamide or of diacetone-acrylamide, with monomers which provide units corresponding to the formula (2) in the copolymer obtained. These polymers are typically in the form of an acetate, borate, bromide, chloride, citrate, tartrate, bisulphate, bisulphite, sulphate, phosphate or succinate.

Amongst the quaternary ammonium polymers of the type defined above, those which are more particularly preferred are the homopolymer of dimethyldiallylammonium chloride, sold under the name MERQUAT 100 and having a molecular weight of less than 100,000, and the copolymer of dimethyldiallylammonium chloride and of acrylamide, which has a molecular weight of more than 500,000 and is sold under the name MERQUAT 550 by Messrs. MERCK.

These cyclopolymers are described in U.S. Pat. Nos. 3,912,808, 3,986,825 and 4,027,008 incorporated by reference. The homopolymers and copolymers of the formulae (2) and (2') can be prepared as described in U.S. Pat. Nos. 2,926,161, 3,288,770 or 3,412,013, the disclosure of these various patents being hereby included by reference.

(3) Homopolymers or copolymers derived from acrylic or methacrylic acid and containing, as the recurring unit:

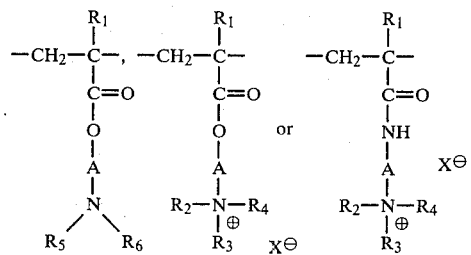

in which $R_1$ is H or $CH_3$, A is a linear or branched alkyl group having 1 to 6 carbon atoms or a hydroxyalkyl group having 1 to 4 carbon atoms, $R_2$, $R_3$ and $R_4$ are identical or different and are an alkyl group having 1 to 18 carbon atoms or benzyl, $R_5$ and $R_6$ are H or alkyl having 1 to 6 carbon atoms and X denotes halogen, such as chlorine or bromine, or methosulphate.

Suitable comonomer or comonomers which can be used include:

acrylamide, methylacrylamide, diacetone-acrylamide, acrylamide and methacrylamide substituted on the nitrogen by lower alkyls, alkyl esters of acrylic and methacrylic acids, vinylpyrrolidone and vinyl esters.

The following may be mentioned by way of example: the copolymer of acrylamide and β-methacryloyloxyethyl-trimethylammonium methosulphate sold under the names Reten 205, 210, 220 and 240 by Messrs. Hercules, the copolymers of ethyl methacrylate, oleyl methacrylate and β-methacryloyloxydiethylmethylammonium methosulphate referred to by the name Quaternium 38 in the Cosmetic Ingredient Dictionary, the copolymer of ethyl methacrylate, abietyl methacrylate and β-methacryloyloxydiethylmethylammonium methosulphate referred to by the name Quaternium 37 in the Cosmetic Ingredient Dictionary, the polymer of β-methacryloyloxyethyltrimethylammonium bromide referred to by the name Qauternium 49 in the Cosmetic Ingredient Dictionary, the copolymer of β-methacryloyloxyethyltrimethylammonium methosulphate and β-methacryloyloxystearyldimethylammonium methsulphate referred to by the name Quaternium 42 in the Cosmetic Ingredient Dictionary, and the copolymer of aminoethyl acrylate phosphate/acrylate sold under the name Catrex by Messrs. National Starch, and also the compounds described in U.S. Pat. No. 3,372,149, which is hereby included by reference, and grafted and crosslinked cationic copolymers having a molecular weight of 10,000 to 1,000,000, and preferably 15,000 to 500,000, resulting from the copolymerisation of: (a) at least one cosmetic monomer, (b) dimethylaminoethyl methacrylate, (c) polyethylene glycol and (d) a polyunsaturated crosslinking agent, which are described in U.S. Pat. No. 3,990,459 which is hereby included by reference.

The crosslinking agent is typically taken from the group comprising: ethylene glycol dimethacrylate, diallyl phthalates, divinylbenzenes, tetraallyloxyethane, and polyallyl-sucroses having 2 to 5 allyl groups per mol of sucrose.

The cosmetic monomer can be of very varied type, for example a vinyl ester of an acid having 2 to 18 carbon atoms, an allyl or methallyl ester of an acid having 2 to 18 carbon atoms, an acrylate or methacrylate of a saturated alcohol having 1 to 18 carbon atoms, an alkyl vinyl ether in which the alkyl radical has 2 to 18 carbon atoms, an olefine having 4 to 18 carbon atoms, a heterocyclic vinyl derivative, a dialkyl or N,N-dialkylaminoalkyl maleate in which the alkyl radicals have 1 to 3 carbon atoms, or an anhydride of an unsaturated acid.

The polyethylene glycol generally has a molecular weight of 200 to several million and preferably from 300 to 30,000.

These grafted and crosslinked copolymers preferably consist of: (a) 3 to 95% by weight of at least one cosmetic monomer chosen from the group comprising: vinyl acetate, vinyl propionate, methyl methacrylate, stearyl methacrylate, lauryl methacrylate, ethyl vinyl ether, cetyl, vinyl ether, stearyl vinyl ether, hex-1-ene, octadecene, N-vinylpyrrolidone and N,N-diethylaminoethyl monomaleate, maleic anhydride and diethyl maleate, (b) 3 to 95% by weight of dimethylaminoethyl methacrylate, (c) 2 to 50% by weight and preferably 5 to 30% of polyethylene glycol and (d) 0.01 to 8% by weight of a crosslinking agent such as those defined above, the percentage of crosslinking agent being expressed relative to the total weight of (a)+(b)+(c).

(4) Cationic polymers chosen from the following group:

(a) the polymers of the formula —A—Z—A—Z— (3), in which A denotes a radical having two amino functional groups and preferably

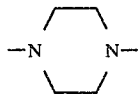

and Z denotes the symbol B or B'; B and B' are identical or different and denote a divalent radical which is a straight-chain or branched alkylene radical which has up to 7 carbon atoms in the main chain and is unsubstituted or substituted one or more by hydroxyl groups and can additionally contain chain oxygen, nitrogen or sulphur atoms and 1 to 3 aromatic and/or heterocyclic rings, the oxygen, nitrogen and sulphur atoms being present in the form of an ether or thioether, sulphoxide, sulphone, sulphonium, amino, alkylamino, alkenylamino, benzylamino, amine oxide, quaternary ammonium, amido, imido, alcohol ester and/or urethane group; this polymer and the process for the preparation thereof are described in U.S. Pat. No. 3,917,817 included by reference.

(b) the polymer of the formula —A—$Z_1$—A—$Z_1$— (4), in which A denotes a radical containing two amino functional groups and preferably

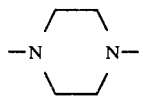

and $Z_1$ denotes the symbol $B_1$ or $B'_1$, at least one $Z_1$ representing the symbol $B'_1$; $B_1$ denotes a divalent radical which is a straight-chain or branched alkylene or hydroxyalkylene radical having up to 7 carbon atoms in the main chain and $B'_1$ is a divalent radical which is a straight-chain or branched alkylene radical which has up to 7 carbon atoms in the main chain and is unsubstituted or substituted by one or more hydroxyl radicals and interrupted by one or more chain nitrogen atoms, the nitrogen atom being substituted by an alkyl chain having optionally 1 to 4 and preferably 4 carbon atoms, which chain is optionally interrupted by an oxygen atom and substituted by one or more hydroxyl and/or carboxyl functional groups;

(c) the polymer of the formula —A'—Z'—A'—Z'— (5), in which A' denotes a mixture of the radicals

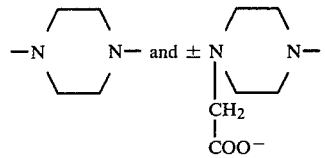

and Z' denotes $B_1$, B, B' or $B'_1$, which have the meaning indicated above; and (d) the quaternary ammonium salts and oxidation products of the polymers of the formula (3) and (4) indicated above under (a) and (b).

The polymers of the formula (4) and of the formula (5) and the process for the preparation thereof are described in U.S. Pat. No. 4,013,787 included by reference.

The polymers of the formula —A—Z—Z—Z— (3) and —A—$Z_1$—A—$Z_1$— (4) can be prepared as indicated in U.S. Pat. No. 3,917,817.

The most particularly preferred polymers are the polycondensation product of N,N'-bis-(2,3-epoxypropyl)-piperazine or of piperazine-bis-acrylamide and piperazine as described in Examples 1, 2 and 14 of U.S. Pat. No. 3,917,817 and the polycondensation products of piperazine, diglycolamine and epichlorohydrin or of piperazine, 2-amino-2-methyl-1,3-propanediol and epichlorohydrin as described in Examples 2, 3, 4, 5 and 6 of U.S. Pat. No. 4,013,787 which patents are hereby included by reference.

(5) Quaternized polymers of the formula

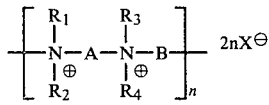

in which $R_1$, $R_2$, $R_3$ and $R_4$ are identical or different and represent aliphatic, alicyclic or araliphatic radicals containing a maximum of 20 carbon atoms, or lower hydroxyaliphatic radicals, or $R_1$ and $R_2$, and $R_3$ and $R_4$, together or separately form, together with the nitrogen atom to which they are linked, heterocyclic structures which can contain a second hetero-atom other than nitrogen, or $R_1$, $R_2$, $R_3$ and $R_4$ represent a group

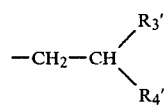

$R'_3$ denoting hydrogen or lower alkyl and $R'_4$ denoting -CN,

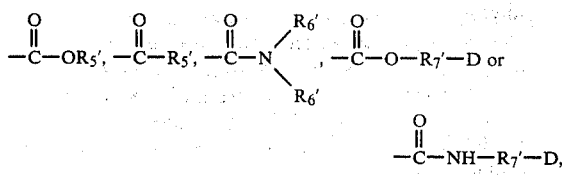

$R'_5$ denoting lower alkyl, $R'_6$ denoting hydrogen or lower alkyl, $R'_7$ denoting alkylene and D denoting a quaternary ammonium group, and A and B can represent polymethylene groups which contain 2 to 20 carbon atoms and can be linear or branched and saturated or unsaturated and can contain, interposed in the main chain, one or more aromatic rings or one or more groups —CH$_2$—Y—CH$_2$—, in which Y denotes O, S, SO, SO$_2$, —S—S—,

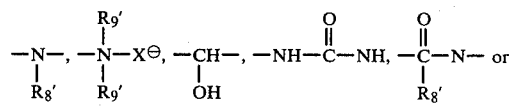

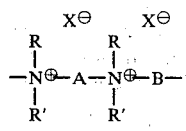

in which $R'_8$ denotes hydrogen or lower alkyl and $R'_9$ denotes lower alkyl, or A and $R_1$ and $R_3$, together with the two nitrogen atoms to which they are linked, form a piperazine ring, $X^\ominus$ is an anion derived from a mineral or organic acid, and n, is such that the polymer molecular weight, is 1,000 to 100,000.

Polymers of this type are described, in particular, in French Patent. No. 2,320,330 and U.S. Pat. Nos. 2,273,780, 2,375,853, 2,388,614, 2,454,547, 3,206,462, 2,261,002 and 2,271,378, which are hereby included by reference.

Other polymers of this type are described in U.S. Pat. Nos. 3,874,870, 4,001,432, 3,929,990, 3,966,904 and 4,005,193, which are hereby included in the present description by reference.

Amongst these polymers, those which may be mentioned are the quaternized polymers based on recurring units of the general formulae:

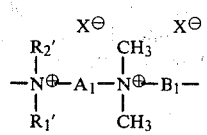

in which: $X^\ominus$ represents an anion derived from a mineral or organic acid; R is a lower alkyl group or a —CH$_2$—CH$_2$OH group; R' is an aliphatic radical, an alicyclic radical or an araliphatic radical, and R' contains at most 20 carbon atoms; $R'_2$ is an aliphatic radical having at most 20 carbon atoms and $R'_1$ is an aliphatic radical, an alicyclic radical or an araliphatic radical containing at most 20 and at least 2 carbon atoms, or the radicals R and R', or $R'_1$ and $R'_2$, linked to a single nitrogen atom form, with this atom, a ring which can contain a second hetero-atom other than nitrogen; A represents a divalent group having one of the formulae given below:

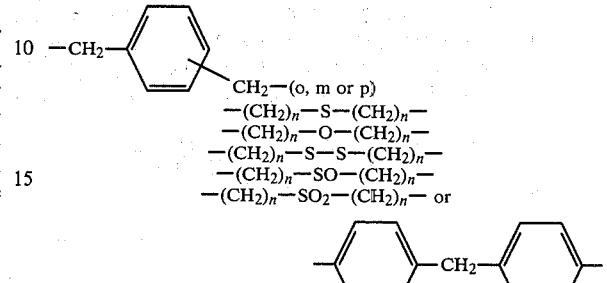

n being an integer of 2 or 3; $A_1$ and likewise A represent a divalent group of the formulae:

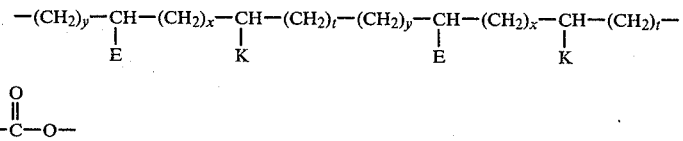

in which x, y and t are independently 0 or integers from 1 to 11 such that the sum $(x+y+t)$ is greater than or equal to 0 but less than 18, and E and K represent a hydrogen atom or an aliphatic radical having less than 18 carbon atoms, and B and $B_1$ represent a divalent group of the formula:

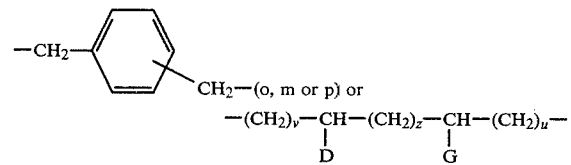

in which D and G represent a hydrogen atom or an aliphatic radical having less than 18 carbon atoms, and v, z and u are independently 0 or integers from 1 to 11 and two of which can be 0 at the same time, such that the sum $(v+z+u)$ is greater than or equal to 1 and less than 18 and such that the sum $(v+z+u)$ is greater than 1 when the sum $(x+y+t)$ is equal to 0, or represent a divalent group of the formula:

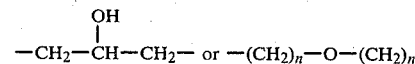

n being as defined above.

The terminal groups of the polymers of the formula (7) can be of the type

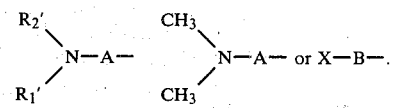

In the general formulae (6) and (7), $X^\ominus$ especially represents a halide anion (bromide, iodide or chloride)

or an anion derived from other mineral acids, such as phosphoric acid or sulphuric acid, or an anion derived from an organic sulphonic or carboxylic acid, especially an alkanoic acid having 2 to 12 carbon atoms (for example phenylacetic acid), benzoic acid, lactic acid, citric acid or para-toluenesulphonic acid.

The substituent R preferably represents an alkyl group having 1 to 6 carbon atoms. When R' or R'$_1$ and R'$_2$ represent an aliphatic radical, this is especially an alkyl or cycloalkylalkyl radical having less than 20 carbon atoms and preferably having not more than 16 carbon atoms and in particular having 1 to 8 carbon atoms.

When R' or R'$_1$ represents an alicyclic radical, this is especially a cycloalkyl radical having 5 or 6 ring members.

or p-xylylidene radical, or B$_1$ is a polymethylene radical having 3, 4, 5 or 6 carbon atoms which can be branched by one or two alkyl substituents having 1 to 12 carbon atoms, and preferably —CH$_2$—CHOH—CH$_2$—.

This invention includes the use of the polymers of the formula (6) or (7) in which the groups A, B, R or R', A$_1$, B$_1$, R'$_1$ and R'$_2$ have several different values in a single polymer 6 or 7.

Polymers of this type are described in particular in the U.S. patent applications of the Applicant Company, Ser. Nos. 577,836 and 702,924, both now abandoned, which are hereby included in the present description by reference.

The preferred polymers are those which contain the following units:

(G1)

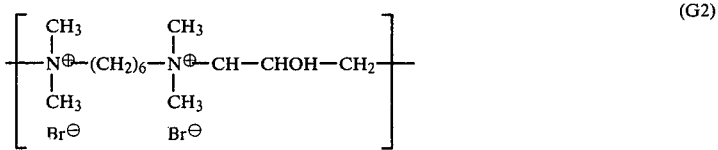

(G2)

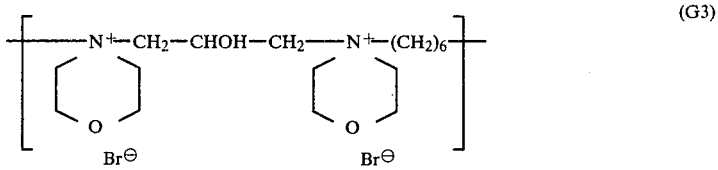

(G3)

(G4)

and

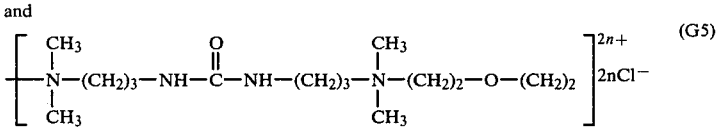

(G5)

When R' or R'$_1$ represents an araliphatic radical, this is especially an aralkyl radical such as a phenylalkyl radical in which the alkyl group preferably has 1 to 3 carbon atoms; when two radicals R and R' or R'$_1$ and R'$_2$, linked to a single nitrogen atom, form a ring together with this atom, R and R' or R'$_1$ and R'$_2$ can together represent in particular a polymethylene radical having 2 to 6 carbon atoms, and the ring can contain a second hetero-atom, for example oxygen or sulphur, and in particular can represent the radical —(CH$_2$)$_2$—O—(CH$_2$)$_2$—.

R'$_1$ is preferably an alkyl radical having 2 to 18 carbon atoms and especially 2 to 16 carbon atoms, a benzyl radical or a cyclohexyl radical.

Amongst the polymers of the formula (7) those which may be mentioned more particularly are those in which R'$_1$ is an ethyl, propyl, butyl, hexyl, octyl, decyl, dodecyl, hexadecyl, cyclohexyl or benzyl radical; A$_1$ is a polymethylene radical having 3, 5, 6, 8, 9 or 10 carbon atoms which can be substituted by one or two alkyl substituents having 1 to 12 carbon atoms; and B$_1$ is an o- or p-xylylidene radical, or B$_1$ is a polymethylene radical having 3, 4, 5 or 6 carbon atoms which can be branched by one or two alkyl substituents having 1 to 12 carbon atoms, and preferably —CH$_2$—CHOH—CH$_2$—.

n being about 6; poly-(dimethylbutenylammonium chloride)-α,ω-bis-(triethanolammonium) chloride, sold under the name ONAMER M by Messrs. ONYX Chemical Co.

Other polymers of this type which can be used in carrying out the invention are those described in French Patent Application No. 2,336,434 and in particular those which correspond to the formula mentioned above in which B denotes a group:

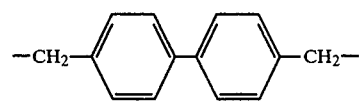

Polymers of this type are also described in U.S. Pat. Nos. 4,025,617, 4,025,627, 4,025,653, 4,026,945 and 4,027,020, which are hereby included by reference.

It is also possible to use, according to the invention, polymers of the ionic type mentioned above which correspond to the formula:

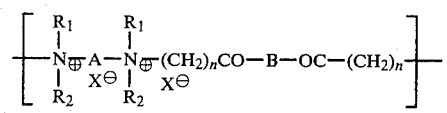

in which: A denotes a linear or branched, saturated or unsaturated alkylene or hydroxyalkylene radical; B denotes: (a) a radical of the formula —O—Z—O—, in which Z denotes a linear or branched hydrocarbon radical or a group corresponding to the formulae

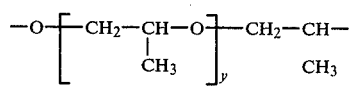

in which x and y denote an integer from 1 to 4 representing a defined and specific degree of polymerization or any number from 1 to 4 representing a mean degree of polymerization; (b) a radical of a bis-secondary diamine, such as a derivative of piperazine of the formula:

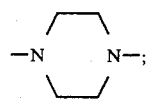

(c) a radical of a bis-primary diamine of the formula: —NH—Y—NH—, in which Y denotes a linear or branched hydrocarbon radical or the divalent radical —CH$_2$—CH$_2$—S—S—CH$_2$—CH$_2$—; or (d) a ureylene group of the formula —NH—CO—NH—; R$_1$ denotes an alkyl radical having 1 to 4 carbon atoms; R$_2$ denotes a linear or branched hydrocarbon radical having 1 to 12 carbon atoms and the radicals R$_2$ can also denote methylene groups which are linked to one another and, together with A, when A denotes an ethylene radical, and the two nitrogen atoms, form a divalent radical derived from the piperazine corresponding to the formula:

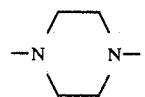

and X$^-$ denotes a halide and in particular bromide or chloride and n denotes the number 1 or an integer from 3 to 10.

These polymers can be prepared according to the processes which are in themselves known, by polycondensation of a bis-tertiary diamine of the formula:

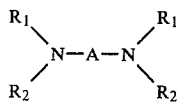

with a bis-halogenoaryl compound of the formula:

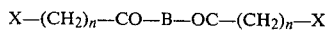

the various substituents having the same meanings as mentioned above.

Amongst these polymers, those which are most particularly preferred are those which contain the following units and which can be prepared by polycondensation:

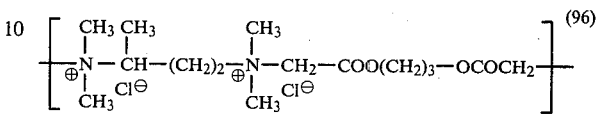

having an absolute viscosity of 0.99 cps

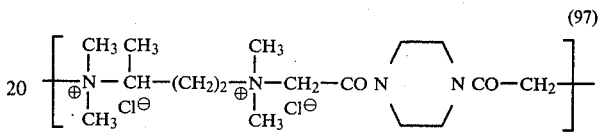

having an absolute viscosity of 1.62 cps

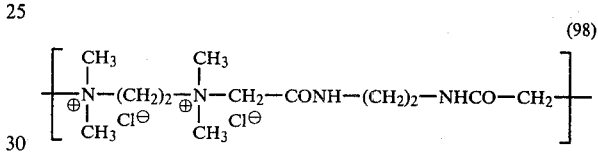

having an absolute viscosity of 1.39 cps

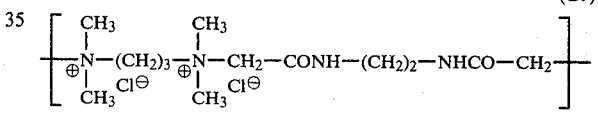

having an absolute viscosity of 1.94 cps
and

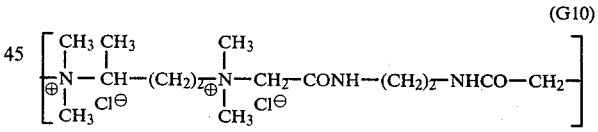

having an absolute viscosity of 1.73 cps.

(6) Copolymers of vinylpyrrolidone having recurring units of the formulae:

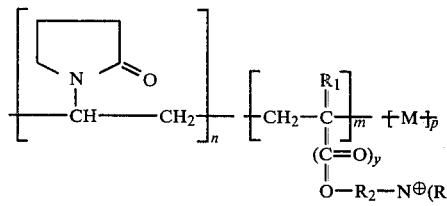

in which n represents from 20 to 99 and preferably from 40 to 90 mol %, m represents from 1 to 80 and preferably from 5 to 40 mol %; p represents 0 to 50 mol, (n+m+p=100); R$_1$ represents H or CH$_3$; y denotes 0 or 1; R$_2$ is —CH$_2$—CHOH—CH$_2$— or C$_x$H$_{2x}$ in which x is 2 to 18; R$_3$ represents CH$_3$, C$_2$H$_5$ or

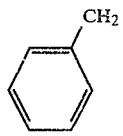

and $R_4$ denotes $CH_3$ or $C_2H_5$; $X^-$ is chosen from amongst Cl, Br, I, ½ $SO_4$, $HSO_4$ and $CH_3SO_3$; and M is a monomeric unit resulting from hetero-polymerisation using a selected copolymerisable vinyl monomer. The polymers can be prepared according to the process described in French Pat. No. 2,077,143, which is herebyy included by reference.

The preferred copolymers have molecular weights of about 100,000 to 1,000,000, such as the commercially available products "Gafquat 734" and "Gafquat 755" of the "GAF CORPORATION" of New York.

(7) The polyamino-amides (A) as described below.

(8) Crosslinked polyamino-amides, which may or may not be alkylated, which are soluble in water and obtained by crosslinking a polyamino-polyamide (A) prepared by polycondensation of an acid compound and a polyamine. The acid compound is suitably chosen from (i) organic dicarboxylic acids, (ii) aliphatic mono- and di- carboxylic acids having an ethylenic double bond, (iii) esters of the abovementioned acids, preferably with lower alkanols having 1 to 6 carbon atoms, and (iv) mixtures of these compounds. The polyamine is chosen from amongst bis-primary and mono- or di-secondary polyalkylene-polyamines. 0 to 40 or 50 mol % of this polyamine can be replaced by a bis-primary amine, preferably ethylenediamine, or by a bis-secondary amine, preferably piperazine, and 0 to 20 mol % can be replaced by hexamethylenediamine. Crosslinking is effected by means of a crosslinking agent (B) which may be epihalogenohydrins, diepoxides, dianhydrides, unsaturated anhydrides and bis-unsaturated derivatives; the crosslinking is characterised in that it is effected by means of 0.025 to 0.35 mol of crosslinking agent per amine group in the polyamino-polyamide (A), and generally of 0.025 to about 0.2 and in particular 0.025 to about 0.1 mol of crosslinking agent per amine group in the polyamino-polyamide (A).

This crosslinked polymer dissolves completely in water to give a 10% strength solution, without the formation of a gel; the viscosity of a 10% strength solution in water at 25° C. is greater than 3 centipoise and usually between 3 and 200 centipoise.

The acids which can be used to prepare the polyaminopolyamides (A) are typically: saturated organic dicarboxylic acids having 6 to 10 carbon atoms, for example adipic acid, 2,2,4- and 2,4,4-trimethyladipic acid, terephthalic acid and aliphatic monocarboxylic and dicarboxylic acids having an ethylenic double bond, for example acrylic acid, methacrylic acid and itaconic acid.

It is also possible to use the esters of the acids mentioned above or mixtures of two or more carboxylic acids or their esters.

The polyamines which can be used to prepare the polyaminopolyamides (A) are chosen from amongst the bis-primary or mono- or di-secondary polyalkylene-polyamines, for example diethylenetriamine, dipropylenetriamine, triethylenetetramine, and mixtures thereof.

Preferably, the dicarboxylic acid and the amines are used in equimolar amounts relative to the primary amine groups of the polyalkylene-polyamines.

The constitution of the preferred polyamino-amides (A) can be represented by the general formula (I)

in which R represents a divalent radical which is derived from the acid used or from the addition product of the acid with the bis-primary or bis-secondary amine, and Z represents:

(1) in proportions of 60 to 100 mol %, the radical

in which x is 2 and n is 2 or 3, or x is 3 and n is 2, this radical being derived from diethylenetriamine, triethylenetetramine or dipropylenetriamine;

(2) in proportions of 0 to 40 mol %, the above radical (II), in which x is 2 and n is 1, and which is derived from ethylenediamine, or the radical

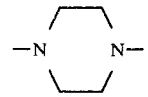

which is derived from piperazine; and (3) in proportions of 0 to 20 mol %, the radical —NH—$(CH_2)_6$—NH— which is derived from hexamethylenediamine.

The preparation of the polyamino-amides (A) is described in more detail in French Patent Application No. 2,252,840 and U.S. Pat. Application Ser. No. 762,804, now U.S. Pat. No. 4,172,887, CIP OF Ser. No. 528,577 filed on Nov. 29, 1974, now abandoned.

The polyamino-polyamides thus obtained are then cross-linked by the addition of a crosslinking agent. The cross-linking agent used is a bifunctional compound chosen from amongst (a) the epihalogenohydrins, for example epichlorohydrin; (b) the diepoxides, for example diglycidyl ether or N,N'-bis-epoxypropylpiperazine; (c) the dianhydrides, for example the dianhydride of butanetetracarboxylic acid or the dianhydride of pyromellitic acid; and (d) the bis-unsaturated derivatives, for example divinyl sulphone or methylene-bis-acrylamide.

The crosslinking reactions are suitably carried out at 20° C. to . . . , using, as the starting material, 20 to 30% strength aqueous solutions of polyamino-polyamide, to which the cross-linking agent is added in very small amounts until a significant increase in the viscosity takes place, but nevertheless without reaching the stage where a gel, which will not redissolve in water is produced. The concentration is then rapidly adjusted to 10% by adding water and the reaction mixture is cooled if necessary.

The secondary amine groups in the crosslinked polyaminoamides can be alkylated.

The alkylating agent used can be e.g. an epoxide, for example glycidol, ethylene oxide or propylene oxide, or a compound having an ethylenic double bond, for example acrylamide.

The alkylation of the crosslinked polyamino-amides is suitably carried out in aqueous solution at a concentration of 10 to 30% and at a temperature of 10° to 95° C. The degree of alkylation relative to the total basicity varies between 0 and 80%.

The crosslinked polyamino-amides, which may be alkylated, do not contain any reactive group and do not have alkylating properties and are chemically stable.

The polymers indicated below are amongst the preferred polyamino-amide polymers (A) and the crosslinked, and optionally alkylated, polyamino-amide polymers (A):

The polymer designated K I, which results from the polycondensation of equimolar amounts of adipic acid and diethylenetriamine.

The polymer designated K Ia, which results from cross-linking polymer K I with epichlorohydrin (11 mols of epichlorohydrin per 100 amine groups).

The crosslinked polymer designated K Ib, which results from crosslinking polymer K I with methylene-bis-acrylamide (12.1 mols of methylene-bis-acrylamide per 100 amine groups in the polyamino-polyamide).

The polymer designated K Ic, which results from cross-linking polymer K I with N,N'-bis-epoxy-propyl-piperazine (7.3 mols of the crosslinking agent per 100 amine groups in the polyamino-amide).

The polymer designated K Id, which results from cross-linking polymer K I by means of divinyl sulphone (13.9 mols of the crosslinking agent per 100 amine groups in the polyaminoamide).

The polymer designated K Ie, which results from cross-linking polymer K I with the bis-acrylamide of piperazine.

The polymer designated K II, which results from the polycondensation of 3 mols of adipic acid with one mol of piperazine and 2 mols of diethylenetriamine.

The polymer designated K IIa, which results from cross-linking polymer K II with epichlorohydrin (13.2 mols of the crosslinking agent per 100 amine groups in the polyamino-amide).

The polymer designated K III, which results from the polycondensation of equimolar amounts of adipic acid and triethylenetetramine.

The polymer designated K IIIa, which results from cross-linking polymer K III with epichlorohydrin (7.8 mols of the cross-linking agent per 100 amine groups in the polyamino-amide).

The polymer designated K IIIb, which results from cross-linking polymer K III with methylene-bis-acrylamide (3.4 mols of the crosslinking agent per 100 amine groups in the polyaminoamide).

The polymer designated K IV, which results from the polycondensation of the reaction product of 2 mols of methyl itaconate and 1 mol of ethylenediamine with diethylenetriamine.

The polymer designated K IVa, which results from cross-linking polymer K IV with epichlorohydrin (22 mols of epichlorohydrin per 100 amine groups in the polyamino-amide).

The polymer designated K IVb, which results from cross-linking polymer K IV with methylene-bis-acrylamide (16 mols of the crosslinking agent per 100 amine groups in the polyaminoamide).

The polymer designated K V, which results from the polycondensation of a mixtuure of 2 mols of methyl acrylate and 1 mol of ethylenediamine with diethylene-triamine.

The polymer designated K Va, which results from cross-linking polymer K V with epichlorohydrin.

The polymer designated K VI, which results from the polycondensation of a mixture of 2 mols of methyl methacrylate and 1 mol of ethylenediamine with diethylenetriamine.

The polymer designated K VIa, which results from cross-linking polymer K VI with methylene-bis-acrylamide (21.4 mols of the crosslinking agent per 100 amine groups in the polyaminoamide).

The polymer K VII, which results from the alkylation of polymer K Ia with glycidol.

The polymer designated K VIII, which results from the alkylation of polymer K Ia with acrylamide.

The preparation of all these polymers is described in French Application No. 2,252,840 or U.S. Ser. No. 762,804 of Jan. 26, 1972 which is hereby included by reference.

(9) The water-soluble crosslinked polyamino-amides obtained by crosslinking a polyamino-amide (A described above) by means of a crosslinking agent chosen from the group comprising:

(I) compounds chosen from the group comprising (1) the bis-halogenohydrins, (2) the bis-azetidinium compounds, (3) the bis-halogenoacyl dervatives of diamines and (4) the alkyl bis-halides;

(II) the oligomers obtained by reacting a compound (a) chosen from the group comprising (1) the bis-halogenohydrins, (2) the bis-azetidinium compounds, (3) the bis-halogenoacyl derivatives of diamines, (4) the alkyl bis-halides, (5) the epihalogenohydrins, (6) the diepoxides and (7) the bis-unsaturated derivatives, with a compound (b) which is a bifunctional compound reactive towards compound (a); and (III) the quaternization product of a compound chosen from the group comprising the compounds (a) and the oligomers (II) and containing one or more tertiary amine groups which can be wholly or partially alkylated by an alkylating agent (c), preferably chosen from the group comprising the methyl or ethyl chlorides, bromides, iodides, sulphates, mesylates and tosylates, benzyl chloride or bromide, ethylene oxide, propylene oxide and glycidol, crosslinking being effected by means of 0.025 to 0.35 mol, in particular 0.025 to 0.2 mol, and more particularly 0.025 to 0.1 mol of the crosslinking agent per amine group in the polyaminoamide.

The bis-halogenohydrins can be obtained by reacting an epihalogenohydrin, such as epichlorohydrin or epibromohydrin, with bifunctional compounds such as secondary bis-amines, primary amines, diols, bis-phenols or bis-mercaptans.

They can be direct intermediates for the preparation of the bis-epoxides but, conversely, they can be derived therefrom by opening the oxirane ring with a hydracid, such as hydrochloric acid or hydrobromic acid.

In both cases the halogen atom can be linked to the final or penultimate carbon atom without its position affecting the reactivity of the crosslinking agent or the properties of the end product.

The following dihalogenohydrins may be mentioned by way of example:

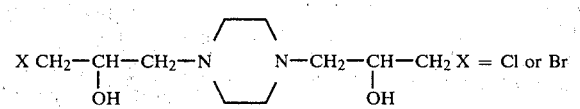

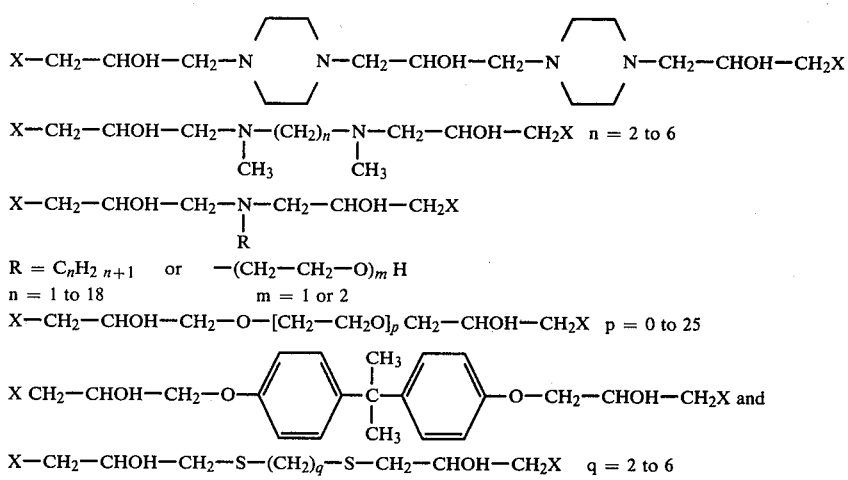

The bis-azetidinium compounds are derived from N,N-dialkylhalogenohydroxypropylamines by cyclization.

However, cyclization can be difficult for certain sterically hindered amines.

Since the reactivity of azetidinium groups is little different to that of epihalogenohydrin groups, it is possible to use, for the purposes of the invention, compounds which are derived from bis-halogenohydrins in which the halogenohydrin units are bonded to the remainder of the molecule by tertiary nitrogen groups and which contain two azetidinium groups or one azetidinium group and one halogenohydrin group.

The bis-halogenoacyl derivatives of diamines which can be used as crosslinking agents can be represented by the following formula

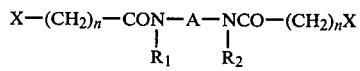

$X = Cl$ or $Br$, $A = -CH_2CH_2$, $-CH_2-CH_2-CH_2-$ or

n denotes a number from 1 to 10, and $R_1 = R_2 = H$ or $R_1$ and $R_2$ can be linked together and together denote the ethylene radical. When

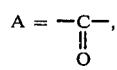

$R_1 = R_2 = H$.

Bis-chloroacetyl- or bis-bromoundecanoyl-ethylenediamine or -piperazine are particularly valuable for the purposes of the invention.

The alkyl bis-halides which can be used according to the invention can be represented by the following general formula:

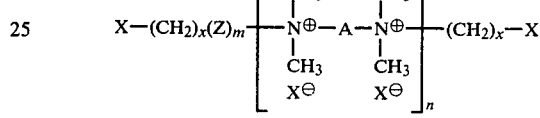

wherein $X = Cl$ or $Br$, $Z$ denotes

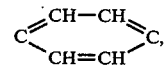

$x = 1$ to 3, $m = 0$ or 1 and $n = 0$ or 1.

m and n may not denote 1 at the same time. When $m = 1$, $x = 1$.

A denotes a divalent saturated $C_2$, $C_3$, $C_4$ or $C_6$ hydrocarbon radical or the 2-hydroxy-propylene radical.

The oligomers which can be used are usually statistical mixtures of compounds obtained by reacting a compound (a) described in groups I and II with a bifunctional compound (b) which is reactive towards these compounds (a), that is to say, in general, bis-secondary amines such as piperazine, bis-tertiary amines such as N,N,N',N'-tetramethylethylene-, -propylene-, -butylene- or -hexamethylene-diamine, bis-mercaptans such as ethane-1,2-dithiol or bis-phenols such as "Bisphenol A" or 2,2-(4,4'-dihydroxy-diphenyl)-propane.

The molar ratios of b relative to a are typically 0.1 to 0.9.

The oligomerization reactions are generally carried out at temperatures of 0° to 95° C. and preferably 0° to 50° C., in water or in a solvent such as isopropanol, t-butanol, acetone, benzene, toluene, dimethylformamide or chloroform.

The quaternization reactions which lead to a quaternization product described above under III can be carried out at 0° to 90° C. in water or in a solvent such as methanol, ethanol, isopropanol, t-butanol, alkylethanols, acetone, benzene, toluene, dimethylformamide or chloroform.

The secondary amine groups in the above crosslinked polyamino-amide polymers can be alkylated and this increases their solubility in water.

Alkylating agents which can be used are: (1) an epoxide, for example glycidol, ethylene oxide or propylene oxide, or (2) a compound having an ethylenic double bond, for example acrylamide.

The alkylation of the crosslinked polyamino-amides is suitably carried out in aqueous solution at a concentration of 10 to 30% and at a temperature of 10° to 95° C.

Amongst the preferred crosslinking agents and crosslinked polymers chosen from amongst those described above, the following may be listed:

Crosslinking agent R Ia

This crosslinking agent, of the formula

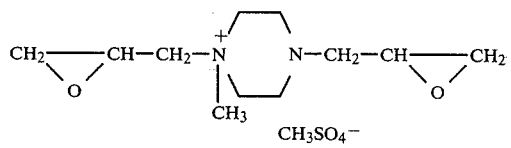

is prepared as indicated below:

36.4 g (0.289 mol) of dimethyl sulphate are added in the course of one hour to 236 g of a chloroform solution containing 57.2 g (0.289 mol) of bis-(epoxypropyl)-piperazine, whilst stirring the reaction mixture at 30° C.

The quaternized derivative is then precipitated from its solution in a large excess of ether. After drying, a highly viscous oil is collected. Its epoxide content is 5.9 milliequivalents/g.

Polymer KA Ib

This polymer is obtained by crosslinking polymer K I with crosslinking agent R Ia, as indicated below:

22 g (0.057 mol) of crosslinking agent R Ia are added, at ambient temperature, to 500 g of an aqueous solution containing 100 g (0.585 amine equivalent) of polyaminoamide K I (prepared by a condensation reaction of equimolar amounts of adipic acid and diethylentriamine) and the temperature of the reaction mixture is then raised to 90° C.

After 20 minutes gelling of the solution is observed. 698 g of water are then added rapidly. A clear solution which is yellow-green in colour and contains 10% of active material is obtained. The viscosity, measured at 25° C., is 0.68 poise at 87.93 seconds$^{-1}$.

Crosslinking agent R IIa

This crosslinking agent, of the formula

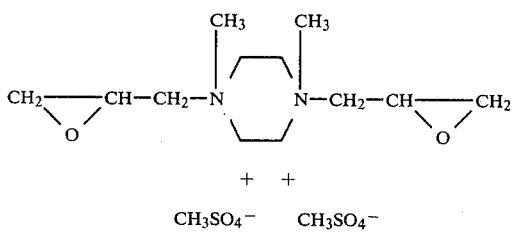

is prepared as indicated below:

70 g (0.555 mol) of dimethyl sulphate are added in the course of one hour to 187.3 g of a chloroform solution containing 54.9 g (0.277 mol) of bis-(epoxypropyl)-piperazine, whilst stirring the reaction mixture at 30° C.

The mixture thickens during the addition and becomes a mass after several hours at ambient temperature. The paste is dissolved in hot dimethylformamide. White crystals which have a melting point of 205° C. and an epoxide index of 4.25 milliequivalents/g separate out from the solution when cold.

Polymer KA IIb

This polymer is obtained by crosslinking polymer K I with a crosslinking agent R IIa, as indicated below:

20 g (0.0425 mol) of the crosslinking agent prepared above are added at ambient temperature to 476 g of an aqueous solution containing 95.2 g (0.557 amine equivalent) of polyaminoamide K I. The reaction mixture is stirred at 90° C. for 1 hour and the solution is then diluted to a content of 10% of active material by adding 656 g of water.

The solution is clear and yellow-green in colour. The viscosity, measured at 25° C., is 0.27 poise at 87.93 seconds$^{-1}$.

Crosslinking agent R IIIa

This is a bis-unsaturated oligomeric crosslinking agent obtained in the following manner starting from the bis-acrylamide of piperazine and piperazine in molar ratios of 3/2:

223 g of an aqueous solution containing 56.8 g (0.66 mol) of piperazine are added in the course of one hour, at between 10° and 15° C., to 380 g of an aqueous solution containing 194 g of bis-acrylamide (1 mol). The reaction mixture is then left at ambient temperature for 24 hours. The solution becomes cloudy and thickens. It is clearified by heating and then run drop by drop into 5 liters of acetone. The crosslinking agent precipitates. After filtering off and drying, a white solid is obtained which has a solids content of 80%.

Polymer KA IIIb

This polymer is obtained by crosslinking polymer K I with crosslinking agent R IIIa in the following manner:

50 g of the crosslinking agent prepared above are added at ambient temperature to 370 g of an aqueous solution containing 111 g (0.649 amine equivalent) of polyamino-amide K I and the temperature of the reaction mixture is then raised to 90° C. The mixture gels after 30 minutes. The solution is rapidly diluted to a 10% solids content by adding 1,050 g of water.

A clear yellow-green solution with a viscosity, measured at 25° C., of 5.8 centipoise is obtained.

Crosslinking agent R IVa

Bis-halogenohydrin oligomeric crosslinking agent prepared starting from epichlorohydrin and piperazine in molar ratios of 5/4 and having the formula:

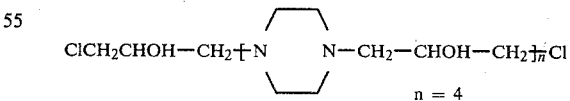

This crosslinking agent is prepared in the following manner:

92.5 g (1 mol) of epichlorohydrin are added in the course of one hour, without exceeding 20° C., to 541 g of an aqueous solution containing 69.4 g (0.806 mol) of piperazine. The reaction mixture is stirred for a further one hour at 20° C. and 60 g (0.6 mol) of 40% strength sodium carbonate are then added at the same temperature in the course of one hour.

Polymer KA IVb

This polymer is obtained by crosslinking polymer K I with crosslinking agent R IVa in the following manner:

268 g of an aqueous solution containing 54.9 g of the crosslinking agent prepared above are added at ambient temperature to 787.5 g of an aqueous solution containing 157.5 g (0.92 amine milliequivalent) of polyamino-amide K I. The temperature of the reaction mixture is kept at 90° C. for 4 hours 50 minutes. Gelling is then observed. A clear solution which contains 9.85% of active material and has a viscosity, measured at 25° C., of 73 centipoise obtained by the rapid addition of 1,100 cc of water.

Crosslinking agent R Va

The quaternized crosslinking agent of the formula:

$$\left[ ClCH_2-CHOH-CH_2-\overset{+}{\underset{CH_3SO_4^-}{N}}\underset{\diagdown}{\overset{CH_3}{\diagup}}\underset{\diagup}{\overset{\diagdown}{N}}-CH_2-CHOH-CH_2 \right]_n Cl$$

n = 4 is prepared in the following manner:

47.4 g of (0.376 mol) of dimethyl sulphate are added in the course of one hour and without exceeding 30° C. to 330 g of an aqueous solution containing 67.7 g (0.752 amine equivalent) of crosslinking agent R IVa. The reaction mixture is stirred for a further 2 hours at this temperature.

Polymer KA Vb

This polymer is obtained by crosslinking polymer K I with crosslinking agent R Va in the following manner:

155 g of an aqueous solution containing 47.25 g of the crosslinking agent prepared above are added at ambient temperature to 327.7 g of an aqueous solution containing 65.5 g (0.383 amine equivalent) of polyamino-amide K I. After heating at 85° C. for 4 hours, the reaction mixture gels.

A clear solution containing 10% of active material is obtained by the rapid addition of 645 g of water. The viscosity, measured at 25° C., is 0.47 poise at 67.18 seconds$^{-1}$.

Crosslinking agent R VIa

This bis-azetidinium crosslinking agent of the formula:

$$HO-\underset{Cl^-}{\overset{+}{N}}\diagdown N-CH_2-CHOH-CH_2-N\diagup\underset{Cl^-}{\overset{+}{N}}-OH$$

is prepared as indicated below:

43.5 g (0.47 mol) of epichlorohydrin are added, at between 0° and 5° C., to 50 g (0.212 mol) of bis-(1,3-piperazine)-2-propanol, prepared by an addition reaction of epichlorohydrin with piperazine according to Example 15 of French Application No. 72/42,279 of Nov. 29, 1972, dissolved in 100 g of absolute alcohol.

The reaction mixture is left at 0° C. for 24 hours and the crosslinking agent is then precipitated from its solution in a large excess of ether. A white solid which has a softening point of about 120° C. is isolated.

Polymer KA VIb

This polymer is obtained by crosslinking polymer K I with crosslinking agent R VIa in the following manner:

15.4 g (0.036 mol) of crosslinking agent R VIa are added at ambient temperature to 386 g of an aqueous solution containing 77.2 g (0.452 amine equivalent) of polyamino-amide K I. After heating at 90° C. for 2 hours 30 minutes, the mixture gels. A clear solution containing 10% of active material is obtained by the rapid addition of 525 g of water. The viscosity, measured at 25° C., is 0.7 poise at 67.18 seconds$^{-1}$.

Crosslinking agent R VIIa

This bis-(chloroacetyl)-piperazine crosslinking agent of the formula $$ClCH_2-CON\diagup\diagdown NCOCH_2Cl$$

is prepared by a condensation reaction of 2 molecules of chloroacetyl chloride with one molecule of piperazine in the presence of sodium hydroxide or sodium methylate.

Polymer K VIIb

This polymer is obtained by crosslinking polymer K I with crosslinking agent R VIIa in the following manner:

24 g (0.1 mol) of bis-(chloroacetyl)-piperazine are added at ambient temperature to 1,000 g of an aqueous solution containing 200 g (1.170 amine equivalents) of polyamino-amide K I and the temperature of the reaction mixture is then raised to 90° C. After heating for 30 minutes, gelling of the mixture is observed.

1,216 g of water are added rapidly and heating at 80° C. is continued for one hour. A clear solution which contains 10% of active material and has a viscosity, measured at 25° C., of 0.29 poise at 88.41 seconds$^{-1}$ is obtained.

Crosslinking agent R VIIIa

This bis-(1,1-bromoundecanoyl)-piperazine crosslinking agent of the formula:

$$Br(CH_2)_{10}CON\diagup\diagdown NCO(CH_2)_{10}Br$$

is prepared by a condensation reaction of 2 mols of bromoundecanoyl bromide with one mol of piperazine in the presence of sodium hydroxide or sodium methylate.

Polymer KA VIIIb

This polymer is obtained by a condensation reaction of polymer K I with crosslinking agent R VIIIa in the following manner:

60 g of an isopropanol solution containing 10 g (0.017 mol) of bis-(1,1-bromoundecanoyl)-piperazine are added at ambient temperature to 113.3 g of an aqueous solution containing 56.7 g (0.33 amine equivalent) of polyamino-amide K I. The reaction mixture is heated under solvent reflux for 2 hours 30 minutes. The isopropanol is then distilled whilst adding water until an aqueous resin solution containing 10% of active material is obtained. The solution is slightly opalescent and its viscosity, measured at 25° C., is 0.052 poise at 87.93 seconds$^{-1}$.

Crosslinking agent R IXa

This statistical oligomeric crosslinking agent of the formula:

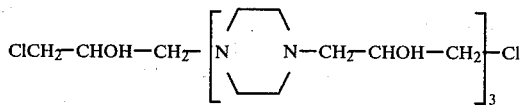

is prepared starting from epichlorohydrin, piperazine and sodium hydroxide in molar ratios of 4/3/2.

246.7 g (2.66 mols) of epichlorohydrin are added in the course of 1 hour to 1,149 g of an aqueous solution containing 172 g (2 mols) of piperazine, whilst stirring the reaction mixture at 20° C.

After stirring for a further hour at 20° C., 133 g (1.33 mols) of 40% strength sodium hydroxide solution are added at the same temperature in the course of one hour. Precipitation is observed in the course of neutralization. 638 g of water are added and the mixture is heated at 50° C. for a few minutes in order to obtain a clear solution.

Polymer KA IXb

This polymer is prepared by crosslinking polymer K I with crosslinking agent R IXa in the following manner:

584 g of an aqueous solution containing 99.8 g of crosslinking agent R IXa are added to 2,000 g of an aqueous solution containing 400 g (2.34 amine equivalents) of polyamino-amide K I and the reaction mixture is then stirred at 90° C. for 5 hours. 2,414 g of water are then added in order to obtain a clear solution which contains 10% of active material and has a viscosity, measured at 25° C., of 0.22 poise.

Crosslinking agent R Xa

This statistical oligomeric crosslinking agent of the formula:

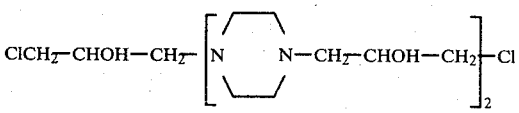

is prepared starting from epichlorohydrin, piperazine and sodium hydroxide in molar ratios of 3/2/1.

277.5 g (3 mols) of epichlorohydrin are added in the course of 1 hour and at 20° C. to 1,221 g of an aqueous solution containing 172 g (2 mols) of piperazine, whilst stirring the reaction mixture. After stirring for a further hour, 100 g (1 mol) of sodium hydroxide, as a 40% strength solution in water, are added at a temperature of 20° C.

A clear solution is obtained by adding 727.5 g of water and after heating for several minutes.

Polymer KA Xb

This polymer is obtained by crosslinking polymer K I with crosslinking agent R Xa in the following manner:

472 g of an aqueous solution containing 83.8 g of the crosslinking agent prepared in Example Xa are added to 2,000 g of an aqueous solution containing 400 g (2.34 amine equivalents) of polyamino-amide K I.

The reaction mixture is stirred at 90° C. and after heating for 4 hours gelling of the solution is observed.

The solution is rapidly diluted to a 10% active material content by adding 2,326 g of water.

A clear solution which has a viscosity, measured at 25° C., of 0.64 poise at 88.4 seconds$^{-1}$ is obtained.

These crosslinking agents and polymers indicated above are described in French Application No. 77/06,031 of 2nd March 1977, which is hereby included in the description by reference.

(10) The water-soluble polyamino-amide derivatives which result from a condensation reaction of the polyalkylene-polyamines with polycarboxylic acids, followed by alkylation by bifunctional agents.

The polyamino-amides which can be used more particularly in the present invention are the compounds which result from the reaction of polyalkylene-polyamines containing two primary amino groups, at least one secondary amino group and alkylene groups containing 2 to 4 carbon atoms, with dicarboxylic acids corresponding to the formula:

$$HOOC-C_mH_{2m}-COOH$$

in which m denotes an integer from 4 to 8, or with a derivative of such acids. The molar ratio of these reactants is preferably between 4:5 and 6:5.

The polyamide which results from this reaction is alkylated by bifunctional alkylating agents which correspond to the formula:

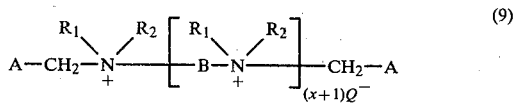

wherein x denotes 0 or an integer of from 1 to 7, A denotes a group

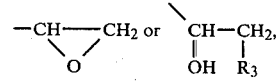

wherein $R_3$ denotes halogen and preferably chlorine or bromine, and $R_1$ and $R_2$ denote a lower alkyl or hydroxyalkyl group containing 1 to 4 carbon atoms, B represents an alkylene radical containing 2 to 6 carbon atoms or a

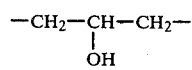

or $-(CH_2)_y-NH-CO-NH-(CH_2)_y-$ radical, wherein y is an integer from 1 to 4, and $Q^-$ denotes halogen, sulphate or methosulphate.

The more particularly preferred polymers are those in which A denotes

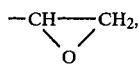

R₁ and R₂ denote a lower alkyl group and in particular methyl, and x is 0.

The amount of bifunctional alkylating agent is such that the derivatives of polyamino-amides which are formed have high molecular weights but are soluble in water.

Such polymers are described, inter alia, in U.S. Pat. No. 3,632,559 which is hereby included by reference.

Preferred polymers of this type are adipic acid/dialkylaminohydroxyalkyl-dialkylenetriamine copolymers in which the alkyl radical contains 1 to 4 carbon atoms and preferably denotes methyl, ethyl or propyl.

The compounds which enable particularly remarkable results to be obtained are adipic acid/dimethylaminohydroxypropyl-diethylenetriamine copolymers sold under the name Cartaretine F, F₄ or F₈ by Messrs. SANDOZ.

These copolymers have a nitrogen content of 17.0 to 18.0% by weight and a viscosity, measured in a 30% strength by weight aqueous solution, of 350 to 800 centipoise at 20° C. (determined by a Brookfield viscometer using a No. 3 spindle at 30 revolutions per minute).

(11) The polymers obtained by reacting a polyalkylene-polyamine containing two primary amine groups and at least one secondary amine group with a dicarboxylic acid chosen from amongst diglycollic acid and saturated aliphatic dicarboxylic acids having 3 to 8 carbon atoms, the molar ratio between the polyalkylene-polyamine and the dicarboxylic acid being between 0.8:1 and 1.4:1, and the resulting polyamide being reacted with epichlorohydrin in a molar ratio of epichlorohydrin relative to the secondary amine group in the polyamide of between 0.5:1 and 18:1, U.S. Pat. Nos. 3,227,615 and 2,916,347 which describe these polymers are hereby included by reference.

Particularly preferred polymers are those sold under the name HERCOSETT 57 by Messrs. Hercules Incorporated, which have a viscosity, at 25° C., of 30 centipoise for a 10% strength aqueous solution, and those sold under the name PD 170 or DELSETTE 101 by Messrs. Hercules, in the case of the adipic acid:epoxypropyl-diethylenetriamine copolymer.

(12) The polyalkylene-amines chosen from the group comprising: the polymerization products of ethylene-imine and its homologues, which products can optionally carry substituents and which are generally obtained in the presence of acid catalysts, as indicated especially in U.S. Pat. No. 2,182,306. The polymerization catalyst can also be an oxidizing agent or a surface-active agent, such as oxyethyleneated products. Amongst these polymers, those which may be mentioned are the polymers of ethylene-imine, propylethylene-imine, butylene-imine, phenylethylene-imine or cyclohexylethylene-imine, and also the copolymers of alkyleneimines with acrylic acid and its derivatives in the presence of amines of high molecular weight, or of ethylene oxide; the polyalkylene-imines which result from the polymerization of alkylene-imines of the formula

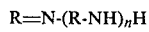 (10)

in which R is a 1,2-alkylene radical and n is an integer of less than 4, and are obtained by simple heating or in an aqueous medium in the presence of an acid, as indicated in U.S. Pat. No. 2,553,696. Amongst these polyalkylene-imines, those which may be mentioned are those which are obtained by polymerization of the following alkylene-imines: C₂H₄=NC₂H₄—NH₂; or N,N-ethylene-ethylenediamine, C₂H₄=NC₂H₄—NHC₂H₄—NH₂; or N,N-ethylene-diethylenetriamine, C₂H₄=N(C₂H₄NH)₂—C₂H₄—NH₂, or N,N-ethylene-triethylenetetramine, (CH₃)C₂H₃=NC₂H₃(CH₃)NH₂; N,N-(1,2-propylene)-1,2-propylenediamine, (CH₃)C₂H₃=NC₂H₃(CH₃)NHC₂H₃(CH₃)NH₂; or N,N-(1,2-propylene)-di-(1,2-propylene)-triamine; (CH₃)C₂H₃=N[C₂H₃(CH₃)NH]₂C₂H₃(CH₃)NH₂, N,N-(1,2-propylene)-tri-(1,2-propylene)-tetramine; (CH₃)₂C₂H₂=NCH(CH₃)CH(CH₃)NH₂ and N,N-(2,3-butylene)-2,3-butylene-diamine; the polyethylene-imines prepared according to the process of U.S. Pat. No. 2,806,839 by heating heterocyclic compounds in which the ring contains, on the one hand, a ketone group and, on the other hand, an oxygen atom and a nitrogen atom located respectively in the α-position relative to the ketone group, such as, for example, cyclic urethanes and 2-oxazolidones which are optionally substituted on the nitrogen atom, heating taking place under reduced pressure with the complete elimination of CO₂ by opening the ring, followed by polymerization; and the polymers which result from a condensation reaction of alkylene-imines such as ethylene-imine, methylethylene-imine or N-phenylethylene-imine with sulphur compounds such as carbon disulphide, carbonyl sulphide, thiophosgene or sulphur chloride, as indicated in U.S. Pat. No. 2,208,095, which is hereby included by reference.

Substances which can also be used in the present invention are the partially alkylated derivatives of the polyethylene-imines mentioned above, the degree of alkylation generally being from 10 to 50%. Polymers of this type which are more particularly preferred are those which result from alkylation with octadecyl bromide, octadecyl chloride, heptadecyl chloride, tetradecyl bromide, hexadecyl sulphate, dodecyl chloride or decyl bromide. Polymers of this type are described in French Pat. No. 2,039,151, which is hereby included by reference.

Further polymers of this type are the alkoxylated derivatives of the polyethylene-imines defined above, prepared by reaction of one part by weight of ethylene oxide or of propylene oxide with one part by weight of polyethylene-imine, such as are described in French Pat. No. 1,506,349.

Amongst the more particularly preferred polyethylene-imines and their derivatives, those which may be mentioned are the products sold under the names: PEI 6; PEI 12; PEI 18: PEI 300; PEI 600; PEI 1200; PEI 1800; and PEI 600 E, which is a polyethylene-imine alkylated with ethylene oxide in a ratio of 1:0.75; and TYDEX 14 and TYDEX 16 which have a density of about 1.06 and a viscosity at 25° C. of more than 1,000 centipoise. These polyethylene-imines are sold by Messrs. DOW CHEMICAL. The various patents mentioned above are hereby included by reference.

Further polyethylene-imines which can be used according to the invention are those sold under the name POLYMIN P, which has a density d20 of about 1.07 and a Brookfield viscosity of 10,000–20,000 centipoise for a 50% strength aqueous solution (at 10° C. and 20 revolutions/minute), POLYMIN SN, which has a density d20 of about 1.06 and a viscosity of 800–1,800 centipoise for a 20% strength aqueous solution, and POLYMIN HS, which has a density d20 of about 1.07 and a viscosity of 500–1,000 centipoise for a 20% strength aqueous solution, all sold by Messrs. BASF.

The reaction products of polyethylene-imine with ethyl formate, described in French Pat. No. 2,167,801, which is hereby included by reference, can also be used within the scope of the invention.

(13) The polymers which contain, in the chain, vinylpyridine or vinylpyridinium units, on their own or combined with one another or with other units such as acrylamide or acrylamide substituted, for example, by an alkyl or alkyl acrylate group; the nitrogen of the pyridinium can be substituted by a $C_1$ to $C_{12}$ alkyl chain and the pyridine or pyridinium nucleus can be substituted by 0 to 3 alkyl groups.

The following may be mentioned by way of example: polyvinylpyridine, poly-(1-butyl-4-vinylpyridinium) bromide, the copolymer of 1-lauryl-4-vinyl-pyridinium bromide and 1-butyl-4-vinyl-pyridinium bromide, the copolymer of 1-lauryl-4-vinyl-pyridinium bromide and 1-ethyl-4-vinyl-pyridinium bromide, the copolymer of 2-vinylpyridine and 1-benzyl-2-methyl-5-vinyl-pyridinium chloride, the copolymer of acrylamide and 1,2-dimethyl-5-vinyl-pyridinium methylsulphate, the copolymer of methacrylamide and 1-benzyl-2-vinyl-pyridinium chloride, the copolymer of methyl methacrylate and 1,2-dimethyl-5-vinyl-pyridinium methylsulphate and the copolymer of ethyl acrylate and 2-methyl-5-vinyl-pyridine and 1,2-dimethyl-5-vinyl-pyridinium chloride.

(14) Urea-formaldehyde cationic resins.

(15) The water-soluble polymers which are condensation products of polyamines and epichlorohydrin, such as, for example, the condensation product of tetraethylenepentamine and epichlorohydrin.

(16) Vinylbenzylammonium homo- or co-polymers, such as, for example vinylbenzylalkylammonium polychloride, the alkyl radical preferably being methyl.

(17) Quaternary polyureylenes of the type described in Belgian Pat. No. 77/3,892, which is hereby included by reference.

According to one variant, it is possible to use colouring polymers in combination with the anionic polymers referred to above and optionally further cationic polymers in the compositions according to the present invention. Such polymers are, inter alia: colouring polymers which consist of a mixture of water-soluble cationic polymers which have a molecular weight of 800 to about 100,000 and contain secondary or tertiary amine groups or quaternary ammonium groups and which either form part of or serve as the direct or indirect anchoring of compounds which carry chromophoric or chromogenic groups, which compounds are termed "CCCCG" in the text which follows, or aryl or araliphatic compounds, it being understood that if the main chain contains amine groups which form part of CCCCG, it necessarily also contains at least 10% of aliphatic amine groups, relative to the total number of amine groups in the chain.

The cationic polycondensation products which can be used as conditioners for hair, and in particular the cationic polymers which are used to prepare the coloring polymers mentioned above, are described in particular in French Pat. Nos. 72/42,279, 74/27,030, 74/39,242, 75/15,162 and 76/20,261 of and in Luxembourg Pat. Nos. 73,794 and 73,795 and are defined in the groups indicated above, relating to cationic polymers.

In the case of cationic polymers which have previously been described as conditioners for hair, a colored product, colorant or colorant precursor is grafted onto some of the amine groups of the starting polymer; however, in order to retain the adsorption properties on the keratin fibres, it is essential that not all of the amine groups are substituted by CCCCG radicals. The CCCCG which is grafted onto the polymer can be soluble or insoluble in water, since the solubility of the coloring cationic polymer according to the invention is a function of the solubility of the corresponding polymer before grafting of the CCCCG radicals. In one variant the polymers are linear or branched but not crosslinked; in another variant the polymer can be slightly crosslinked but in this case crosslinking is kept with restricted limits in order not to decrease the solubility of the polymer in water too greatly. These colouring polymers defined above are soluble in water; they can be used not only in aqueous solution but also in a water-solvent medium, the solubility being retained when solvents such as ethanol, alkylene glycols, glycol ethers or analogous products are added.

These coloring polymers can be obtained according to three processes defined below.

In a first process of preparation, the colouring polymers are obtained by reacting colored reactive compounds with cationic resins containing primary, secondary or tertiary amine groups which can be alkylated.

In a second process of preparation, the colouring polymers are obtained by reacting colored compounds containing amine or phenol groups which can be alkylated with cationic resins containing reactive groups.

In a third process of preparation, the coloring polymers are obtained by reacting an amine compound, or a mixture of amine compounds, which can be dialkylated, with other bifunctional derivatives which have functional groups which are able to react with an amine, one of the two reactants being a CCCCG; these functional groups can be, for example, epoxides, halides or activated double bonds.

In the first process of preparation mentioned above, it is possible to use cationic resins such as polyamines or polyamino-amides, for example those described in the paragraphs below and in French Pat. Nos. 72/42,279, 74/27,030 and 74/39,242. It is also possible to use commercially available resins, such as polyethylene-imines. All these resins contain primary, secondary or tertiary amine groups which can be alkylated and which can react with reactive CCCCG, in particular CCCCG containing mobile chlorine or bromine atoms, epoxide groups or activated double bonds.

In a first variant for carrying out this first process of preparation, the reactive molecules of the starting material, which are going to act on the cationic resin, contain one or more -NHCOCH$_2$Cl radicals. These molecules are preferably compounds which result from the chloroacetylation of colorants containing one or more aromatic amine functional groups substituted by an aminoalkyl radical or containing one or more aminoalkoxy substituents, it being understood that only the extranuclear amine functional groups are chloroacetylated. These chloroacetylated reactive compounds can belong to various large categories of colorants and can be, for example, nitrobenzene colorants, anthraquinone colorants, azo colorants, indamines, indoanilines, indophenols, 1,4-benzoquinone colorants, such as those described in French Pat. No. 73/22,562, or the colorants described in French Pat. No. 1,540,423. Amongst the nitrobenzene colorants, those which may be mentioned are the reactive colorants obtained by chloroacetylation using, as the starting materials, derivatives of ortho, meta- and para-nitroanilines, such as 3-nitro-N-β-aminoethylamino-4-anisole, 3-nitro-6-amino-phenoxyethylamine or 3-nitro-4-amino-phenoxyethylamine, or by chloroacetylation using, as the starting materials, derivatives of nitroparaphenylenediamine, such as 1-(N-β-aminoethylamino)-3-nitro-4-(N'-methylamino)-benzene or 1-(N,N-di-β-hydroxyethylamino)-3-nitro-4-(N'-β-aminoethylamino)-benzene. Amongst the chloroacetylated anthraquinone colorants which can be used, those which may be mentioned are 1-(β-chloroacetylaminoethylamino)-anthraquinone, obtained by chloroacetylation of 1-(β-aminoethylamino)-anthraquinone, or 1-(β-chloroacetylaminopropylamino)-4-(N-methylamino)-anthraquinone, obtained by chloroacetylation of the corresponding product described in British Pat. No. 1,159,557, or 1-hydroxy-4-chloroacetylaminopropylamino-anthraquinone, obtained by chloroacetylation of the product described in British Pat. No. 1,227,825, or γ-chloroacetylaminopropylamino-anthraquinone, obtained by chloroacetylation of the product described in Example 7 of British Pat. No. 1,159,557. In these examples, the chloroacetylation of the anthraquinone starting materials is preferably carried out in dioxane in the presence of sodium carbonate; in the case of the first three anthraquinone compounds mentioned above, all the amine functional groups are chloroacetylated and selective deacylation is then carried out with the aid sulphuric acid; in the case of the fourth anthraquinone compound mentioned above, the extra-nuclear amine functional group is chloroacetylated selectively. Chloroacetylated azo compounds which can be used are obtained by coupling diazonium salts with N-ethyl-N-β-chloroacetylaminoethylaniline; the azo compound of 2-amino-benzthiazole and N-ethyl-N-β-chloroacetylaminoethylaniline may be mentioned by way of example. Amongst the chloroacetylated derivatives of indamines, indoanilines and indophenols, those which may be mentioned are N-[[4-(ethyl-β-chloroacetylaminoethyl)-amino]-phenyl]-2,6-dimethyl-3-amino-benzoquinone-imine, obtained by reacting 4-nitroso-N-ethyl-N-β-chloroacetylaminoethylaniline with 2,6-dimethyl-3-amino-phenol; N-(4-amino-2,5-dimethyl)-2-phenylmethyl-5-amino-benzoquinone-imine, obtained by reacting 2,5-dimethyl-paraphenylenediamine with 2-methyl-5-chloroacetylaminophenol in an ammoniacal medium in the presence of ammonium persulphate may also be mentioned. Amongst the chloroacetylated 1,4-benzoquinone colorants, those which may be mentioned are 2-(N-β-hydroxyethylamino)-5-(N-ethyl-42-(N-β-chloroacetylamino)-anilino)-1,4-benzoquinone, obtained by reacting 4-nitroso-N-ethyl-N-β-chloroacetylaminoethylaniline with 3-(β-hydroxyethylamino)-4-methoxy-phenol in an ammoniacal medium in the presence of hydrogen peroxide. Amongst the chloroacetylated derivatives of the colorants described in French Pat. No. 1,540,423, those which may be mentioned are N-[3-nitro-4-(β-chloroacetylaminoethylamino)-phenyl]-N'-[4'-phenyl]-ethylenediamine, which results from the chloroacetylation of the compound described in Example 17 of French Pat. No. 1,540,423, or 1-methylamino-γ-[2'-nitro-N-ethyl-5-(N-β-chloroacetylaminoethylamino)-phenyl]-4-amino-propylamino-anthraquinone, which results from the chloroacetylation of the compound described in Example 19 of French Pat. No. 1,540,423.

More particularly preferred colorants according to the invention are those which result from the reaction of a polymer containing the structural unit -[NH-(CH$_2$)$_2$NH(CH$_2$)$_2$NHCO(CH$_2$)$_4$—CO+described in French Patent No. 74/39,242, with the azo derivative of 2-amino-benzthiazole and N-ethyl-N-β-chloroacetylaminoethylaniline, designated KCl below, or with 2-(γ-chloroacetylaminopropylamino)-anthraquinone, designated KC2 below.

In a second variant for carrying out the first process of preparation, the reactive colored molecules of the starting material comprise either one or more aromatic amines substituted by ω-halogenoalkyl, 3-chloro-2-hydroxy-propyl or 2,3-epoxy-propyl radicals, or halogenoalkoxy groups on an aromatic nucleus. Amongst these compounds those which may be mentioned in particular are 1-(β-chloroethylamino)-3-nitro-4-(N-methylamino)-benzene, N-ethyl-1-(N-β-chloroethylamino)-3-nitro-4-(N'-methylamino)-benzene, 1-(N-β-bromoethylamino)-3-nitro-4-(N'-dimethylamino)-4-nitrobenzene, 3-nitro-4-amino-phenyl bromoethyl ether, obtained by deacetylation of 3-nitro-4-acetylamino-phenyl bromoethyl ether described in Example 13 of French Pat. No. 74/36,651, 1-(3-chloro-2-hydroxy-propyl)-amino-anthraquinone or 1-(2,3-epoxy-propyl)-amino-anthraquinone.

In a third variant for carrying out the first process of preparation, compounds which can be used are colored reactive compounds containing chlorotriazine groups, as in the products known by the tradename "Procion" and sold by Messrs. ICI, for example those which correspond to the formulae indicated in the Colour Index under references 13,245, 13,190, 18,105 and 18,159.

In a fourth variant for carrying out the said first process of preparation, compounds which can be used are reactive colored compounds having an activated double bond, such as the products known by the tradename "Remazol" and sold by Messrs. Hoechst, for example the vinyl-sulphones of the colorants which correspond to the formula indicated in the Colour Index under the references 18,852 or 61,200.

In the second process of preparation, compounds which can advantageously be used are colored compounds containing amine or phenol groups which can be alkylated without a significant reduction in the color and, in particular, the compounds which have been mentioned for the first and second variants for carrying out the first process of preparation (it being understood that in this case the compounds are the compounds before chloroacetylation or halogenoalkylation). Cationic resins containing reactive groups which can advantageously be used are the reaction products of an epihalogenohydrin (epichlorohydrin or epibromohydrin) with polyamino-amides which result from a polycondensation reaction of a diacid and a polyamide of the type:

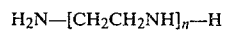

H$_2$N—[CH$_2$CH$_2$NH]$_n$—H in which formula n has a value of 2 or 3.

Amongst the polyamino-amides which are of value, those which may be cited very particularly are those mentioned in French Pat. No. 74/39,242 hereby incorporated by reference. When the epihalogenohydrin is used in proportions ranging from 0.8/1 to about 1.3/1, relative to the basic groups, a resin is obtained which can contain azetidinium, halogenohydrin or epoxide groups, all of which groups alkylate amines or phenols and thus enable colored compounds containing an amine or phenol functional group to be fixed by a covalent bond. The alkylating reactive groups of the resin, which do not react with the colored compounds, can be removed by reaction with a nucleophilic compound, such as an amine or a mercaptan for example, or can be retained in order to further increase the fixing of the coloring polymer on the substrate to be colored.

In the third process for the preparation of the compounds, colored compounds of the type Z—NH$_2$ can be used, such as derivatives which can be dialkylated in the polycondensation reactions with the bis-halogeno derivatives, bis-epoxides or bis-unsaturated derivatives containing activated double bonds. In this case, in addition to the colored compounds Z—NH$_2$, a further bis-secondary amine derivative, for example piperazine, is preferably used in order to increase the solubility in water of the product obtained and also to increase the affinity of this product for keratin fibres. It is also possible to use bis-halogenoalkane or bis-halogenohydrin derivatives of the colored compounds with secondary or tertiary bis-amines (this type of reaction is described in French Pat. No. 75/15161 hereby incorporated by reference).

Amongst the bifunctional derivatives which can be used to react with the amine compounds, those which may be mentioned are, in particular, derivatives of piperazine, such as N,N'-bis-(3-chloro-2-hydroxypropyl)-piperazine, N,N'-bis-(2,3-epoxypropyl)-piperazine and bis-acryloyl-piperazine, diglycidyl ether or the bis-acrylamide of ethylenediamine; it is also possible to use colored bis-amino derivatives with bifunctional derivatives such as those which have just been mentioned, or colored bis-halogeno derivatives with bis-secondary amines.

In the case of the first and second processes of preparation mentioned above, the reactions for the preparation of the reactive halogeno or epoxide derivatives are generally carried out in a solvent medium, in the presence or absence of water, at temperatures of 0° to 100° C. and preferably 30° to 70° C. The following may be mentioned in particular as solvents which can be used: lower alcohols, such as methanol, ethanol, isopropanol and t-butanol, alkoxyethanols, aromatic solvents such as benzene or toluene or other solvents such as dimethylformamide or acetonitrile. The reactions of the reactive colored compounds with the cationic resins are most frequently carried out in the presence of solvents such as those mentioned above at temperatures of 30° to 130° C. and preferably 50° to 90° C.; the reaction time is in general from 1 to 10 hours. These reactions can be carried out on linear or crosslinked cationic resins but it is also possible to crosslink the cationic resin with bifunctional derivatives after grafting of the colored compound. The colouring resins are then precipitated in a non-solvent, such as acetone, methyl ethyl ketone, methyl isobutyl ketone, ethyl ether or hydrocarbons, such as hexane or heptane. Taking into account the reactivity of the colored compounds which, in addition, are in the presence of a significant excess of reactive sites on the resins and taking into account that it is possible to precipitate the coloring substances, it is generally relatively simple to purify the coloring compounds obtained and, in particular, to remove the colorants or colorant precursors which may not have undergone condensation on the resin. When the coloring substances can not be precipitated, it is possible to purify the product obtained by dialysis after solubilization in water. In the cases where colored compounds containing amine or phenol groups are reacted with reactive resins, the reactions are carried out in a solvent medium or in water. When it is desired to retain the reactive resins, the said resins are acidified, for example with hydrochloric acid, before they are isolated. If, on the contrary, it is not desired to retain the reactive resins, a nucleophilic compound, such as an amine or a mercaptan, is added in order to eliminate the usual reactive sites.

The reactions of the third process of preparation can be carried out in water, in solvents or in water/solvent mixtures. These reactions are generally carried out at temperatures of 50° to 150° C. and preferably 80° to 130° C. The reaction time is suitably 1 to 10 hours.

These coloring polymers are described in more detail in French Application No. 76/24,618 of Aug. 12, 1976, which is hereby included by reference.

Amongst the anionic polymers which can be used in the composition according to the invention, those which may be mentioned are the polymers derived from a sulphonic or carboxylic acid.

Polymers which may be mentioned amongst those derived from a sulphonic acid are: salts of polystyrenesulphonic acid, such as the sodium salts sold under the name Flexan 500, which has a molecular weight of about 500,000, or under the name Flexan 130, which has a molecular weight of about 100,000, by Messrs. NATIONAL STARCH. Compounds of this type are described especially in U.S. Pat. No. 3,972,336 which is hereby included by reference. Furthermore, alkali metal or alkaline earth metal salts of the sulphonic acids derived from lignin and, more particularly, the lignosulphates of calcium or sodium, such as the product sold under the name Marasperse C-21 by Messrs. American Can Co. and the C$_{10}$C$_{14}$ products sold by Messrs. Avebene.

Polymers which may be mentioned amongst those derived from a carboxylic acid are:

1. Bipolymers such as the copolymers of vinyl acetate and crotonic acid, such as the resins sold under the designation 26.13.14 or 28.13.10 by MESSRS. NATIONAL STARCH;

2. Graft polymers prepared as described in French Pat. No. 1,222,944 using, as starting materials, compounds, such as vinyl esters or acrylic or methacrylic acid esters on their own or as a mixture copolymerized with other copolymerizable compounds such as crotonic, acrylic or methacrylic acid grafted onto polyalkylene oxides, polyalkylene glycols or appropriate derivatives of these compounds;

Graft polymers of vinyl esters or acrylic or methacrylic acid esters on their own or as a mixture with other compounds which can be copolymerized, onto polyalkylene glycols can be obtained by hot polymerisation in a homogeneous phase by introducing the polyalkylene glycols into the monomers of vinyl esters or acrylic or methacrylic acid esters in the presence of free radical activators.

Appropriate vinyl esters which may be mentioned are: vinyl acetate, vinyl propionate, vinyl butyrate and vinyl benzoate and acrylic or methacrylic acid esters which may be mentioned are those obtained with aliphatic alcohols of low molecular weight containing 1 to 8 carbon atoms.

Polyalkylene glycols which may be mentioned are, above all, polyethylene glycols having a molecular weight of 100 to several million and preferably of 1,000 to 30,000.

Polymers of vinyl acetate grafted onto polyethylene glycols and polymers of vinyl acetate and crotonic acid grafted onto polyethylene glycols may be mentioned very particularly.

Graft polymers of vinyl esters or acrylic or methacrylic acid esters onto derivatives of polyalkylene glycols in which the terminal hydroxyl groups have been etherified or esterified at the two ends by monofunctional or polyfunctional compounds such as methanol, butanol, or acetic, propionic or butyric acid;

Graft polymers of vinyl esters or acrylic or methacrylic acid esters onto nitrogen-containing oxides of polyalkylene glycols.

3. Crosslinked graft copolymers which result from the copolymerization of: (a) at least one monomer of the non-ionic type, (b) at least one monomer of the ionic type, (c) polyethylene glycol and (d) a crosslinking agent preferably taken from the group comprising: ethylene glycol dimethacrylate, diallyl phthalate, the divinylbenzenes, tetraallyloxyethane, and polyallylsucroses having 2 to 5 allyl groups per mol of sucrose.

The polyethylene glycol used generally has a molecular weight of 200 to several million and preferably 300 to 30,000.

The non-ionic monomers can be of very different types and amongst these the following may be mentioned in particular: vinyl acetate, vinyl stearate, vinyl laurate, vinyl propionate, allyl stearate, allyl laurate, diethyl maleate, allyl acetate, methyl methacrylate, cetyl vinyl ether, stearyl vinyl ether and 1-hexene.

The ionic monomers can also be of very different types and amongst these the following may be mentioned in particular: crotonic acid, allyloxyacetic acid, vinylacetic acid, maleic acid, acrylic acid and methacrylic acid.

The crosslinked graft copolymers which can be used according to the invention preferably comprise: (a) from 5 to 85% by weight of at least one non-ionic monomer; (b) from 3 to 80% by weight of at least one ionic monomer; (c) from 2 to 50% by weight, but preferably from 5 to 30%, of polyethylene glycol, and (d) from 0.01% to 8% by weight of a crosslinking agent, the percentage of the crosslinking agent being expressed relative to the total weight of (a)+(b)+(c).

The crosslinked graft copolymers such as have thus been defined generally have a molecular weight of 10,000 to 1,000,000 and preferably of 15,000 to 500,000.

When the crosslinked graft copolymers contain free carboxylic acid functional groups, these groups can be "neutralized" with the aid of a base, in a proportion of 50 to 100% of the amount corresponding to stoichiometric neutralization, such as an organic or mineral base, such as ammonia, monoethanolamine, diethanolamine, triethanolamine, the isopropylamines, isopropanolaniline, morpholine, 2-amino-2-methyl-1-propanol or 2-amino-2-methyl-1,3-propanediol.

Copolymers of this type are described in the German Application (DOS) No. 2,330,956 or U.S. Pat. No. 3,958,581 and Ser. No. 515,074, now U.S. Pat. No. 3,958,581, which is hereby included by reference.

4. The copolymers obtained by copolymerization of at least one monomer of each of the three following groups: the first group comprising the esters of unsaturated alcohols and short-chain saturated carboxylic acids and the esters of short-chain saturated alcohols and unsaturated acids, it being possible for the carbon chains of these compounds to be optionally interrupted by hetero-atoms or divalent hetero-groups, such as —O—, —S— and —NH—, and also to contain substituted hydroxyl groups in the β-position relative to the hetero-atom, the second group comprising unsaturated acids in which the carbon chains can optionally be interrupted by hetero-atoms or divalent hetero-groups, such as —O—, —S— and —NH—, and can contain substituted hydroxyl groups in the β-position relative to the hetero-atom, such as 3-butenoic acid, 4-pentenoic acid, 10-undecenoic acid, allylmalonic acid, crotonic acid, allyloxyacetic acid, crotyloxyacetic acid, methallyloxyacetic acid, 3-allyloxy-propionic acid, allylthioacetic acid, allylaminoacetic acid and vinyloxyacetic acid, and the third group comprising the esters of long-chain acids and an unsaturated alcohol, the esters of the unsaturated acids of the second group and a saturated or unsaturated linear or branched alcohol containing 8 to 18 carbon atoms or a lanolin alcohol, alkyl vinyl ethers, alkyl allyl ethers, alkyl methyallyl ethers or alkyl crotyl ethers, and the α-olefines, described, in particular, in U.S. Pat. No. 3,716,033 which is hereby included by reference.

5. The terpolymers which result from the copolymerisation of: (a) crotonic acid, (b) vinyl acetate, and (c) an allyl or methallyl ester corresponding to the following formula:

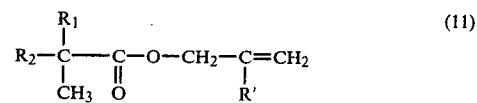

in which R' represents a hydrogen atom or a —CH$_3$ radical; R$_1$ represents a linear or branched saturated hydrocarbon chain having 1 to 6 carbon atoms and R$_2$ represents either the —CH$_3$ radical or the —HC(CH$_3$)$_2$ radical, provided that R$_1$+R$_2$ must have not more than 7 carbon atoms.

The abovementioned terpolymers result, in particular, from the copolymerization of 6–15% and preferably 7–12% of crotonic acid, 65–86% and preferably 71–83% of vinyl acetate and 8–20% and preferably 10–17% of an allyl or methallyl ester of the formula (11).

The terpolymers according to the invention have, preferably, a molecular weight of 15,000 to 30,000.

In a particular embodiment, these copolymers are crosslinked with the aid of a crosslinking agent such as diethylene glycol diallyl ether, tetraallyloxyethane, the triallyl ether of trimethylolpropane and the diacrylates or dimethacrylates of diols such as ethylene glycol, the proportion of crosslinking agent generally being 0.1 to 1.2% by weight.

According to the invention it is also possible to use the terpolymers described above in which the acid functional group has been converted to a salt with the aid of an organic base of the type mentioned in paragraph 3 above.

Terpolymers of this type are described in particular, in U.S. Pat. No. 3,966,404 and Ser. No. 674,274, now U.S. Pat. No. 4,078,533, which is hereby included by reference.

6. The tetra- and penta-polymers which comprise the copolymers which result from the copolymerization of:

(a) an unsaturated acid which is crotonic acid or allyloxyacetic acid; (b) vinyl acetate or vinyl propionate; (c) at least one branched allyl or methallyl ester corresponding to formula (11) defined above, and (d) a monomer taken from the group comprising: (i) a vinyl ether of the formula:

$$CH_2=CH-O-R_3 \qquad (12)$$

in which $R_3$ is a linear or branched alkyl radical having 1 to 12 carbon atoms, and preferably methyl, ethyl, isopropyl, t-butyl, octyl or dodecyl, (ii) a fatty chain vinyl ester of the formula:

$$R_4-\underset{\underset{O}{\|}}{C}-O-CH=CH_2 \qquad (13)$$

in which $R_4$ is a linear alkyl radical having 7 to 11 carbon atoms, and preferably octyl, decyl or dodecyl, and (iii) a linear allyl or methallyl ester of the formula:

$$R_5-\underset{\underset{O}{\|}}{C}-O-CH_2-\underset{\underset{R'}{|}}{C}=CH_2 \qquad (14)$$

in which R' is a hydrogen atom or a —CH₃ radical and $R_5$ is a linear alkyl radical having 1 to 11 carbon atoms, and preferably methyl, heptyl, nonyl or undecyl.

The abovementioned copolymers result, in particular, from the copolymerization of 2–15% and preferably 4–12% of the unsaturated acid, 55–89.5% and preferably 65–85% of the vinyl ester, 8–20% and preferably 10–17% of at least one allyl or methallyl ester of the formula (11), and 0.5–10% and preferably 1–6% of a monomer taken from the group comprising: a vinyl ether of the formula (12), a vinyl ester of the formula (13) and an allyl or methallyl ester of the formula (14).

In a particular embodiment, these copolymers are cross-linked with the aid of a crosslinking agent mentioned above, e.g. in an amount from 0.1 to 1.2% by weight.

It is also possible to use the copolymers described above in which the acid functional group has been converted to a salt with the aid of an organic base, such as has been defined in paragraph 3.

Polymers of this type are described, in particular, in French Patent Application 2,265,781, which is hereby included by reference.

7. The ter-, tetra- and penta-polymers and higher polymers chosen from:
TYPE A—which result from the copolymerisation of (a) at least one water-insoluble monomer of the formula:

$$\underset{\underset{O}{\|}}{CH_2=\underset{\underset{}{|}}{C}-\underset{\underset{}{|}}{C}-NH-\underset{\underset{R_3}{|}}{C}-(CH_2)_n-CH_3} \qquad (15)$$

with $R_1$, $R_2$ above the structure.

in which $R_1$, $R_2$ and $R_3$ represent either a hydrogen atom or a methyl radical and n is 0 or an integer from 1 to 10, inclusive, and preferably N-(tertiary butyl)-acrylamide, N-octyl-acrylamide, N-decyl-acrylamide, N-dodecyl-acrylamide, N-[1-(1,1-dimethyl)propyl]-acrylamide, N-[1-(1,1-dimethyl)-butyl]-acrylamide and N-[1-(1,1-dimethyl)-pentyl]-acrylamide, as well as the corresponding methacrylamides, and (b) at least one water-soluble monomer of the formula:

$$R_4-CH=\underset{\underset{R_5}{|}}{C}-(CH_2)_m-CO\underset{\underset{}{|}}{N}-Z-OH \qquad (16)$$

with R' above N.

in which R' represents a hydrogen atom or a methyl radical, Z represents a linear or branched alkylene radical having 1 to 6 carbon atoms, which is unsubstituted or substituted by one or two hydroxymethyl groups, and m is 0 or 1 and $R_4$ denotes H or —COR₆, $R_6$ being OH or —NH—R₇ and $R_7$ denoting H or —Z—OH, and $R_5$ denotes H or —CH₃ when m=0, and $R_4$ denotes H and $R_5$ denotes CO—R₆ when m=1, and in particular the mono-, bis- or trihydroxy-alkyl-acrylamides or -methacrylamides, in which alkyl denotes a linear or branched group containing 1 to 6 carbon atoms, such as methyl, ethyl, propyl, butyl, 1,1-dimethyl-butyl or propyl; and N-mono- or -di-hydroxyalkyl-maleamic acid, N-mono- or -di-hydroxyalkyl-itaconamic acid and the corresponding amides, in which alkyl preferably denotes methyl, and (c) at least one further monomer taken from the group comprising: acrylic acid, methacrylic acid, maleic anhydride, N-vinylpyrrolidone and the acrylates and methacrylates of the formula:

$$CH_2=\underset{\underset{R'}{|}}{C}-COO-(CH_2-CH_2-O)_l-R'' \qquad (17)$$

in which R' represents a hydrogen atom or a methyl radical, l is 3 or 4 and R'' is a methyl or ethyl radical, amongst which compounds the acrylates or methacrylates of ω-methyl- or -ethylpolyethylene glycol may be mentioned.

According to a further embodiment, the copolymers are tetrapolymers, pentapolymers or higher polymers which result from the copolymerization of more than one monomer of the formula (15) and/or more than one monomer of the formula (16) and/or more than one monomer from the third group (c) above.

According to another variant of the invention, the copolymers result from the copolymerization of a monomer of the formula (15), a monomer of the formula (16), a monomer of group (c) and at least one further monomer, taken from the group comprising: styrene and a monomer corresponding to one of the formulae (18) to (22) which follow:

$$(1)\ CH_2=\underset{\underset{R_8}{|}}{C}-CN \qquad (18)$$

in which $R_8$ represents a hydrogen atom or a methyl radical, i.e. acrylonitrile or methacrylonitrile.

$$(2)\ CH_2=\underset{\underset{R_9}{|}}{C}-\underset{\underset{O}{\|}}{C}-OR_{10} \qquad (19)$$

in which $R_9$ represents a hydrogen atom or a methyl radical and $R_{10}$ represents a linear or branched alkyl radical having 1 to 18 carbon atoms, a —(CH₂)₂N(CH₃)₂ radical or a —CH₂—CH₂OH or

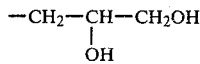

radical, and preferably methyl acrylate and methacrylate, ethyl acrylate and methacrylate, propyl acrylate and methacrylate, isopropyl acrylate and methacrylate, butyl acrylate and methacrylate, tertiary butyl acrylate and methacrylate, hexyl acrylate and methacrylate, decyl acrylate and methacrylate, dodecyl acrylate and methacrylate, octadecyl acrylate and methacrylate, 2-hydroxyethyl acrylate and methacrylate, and N,N-dimethyl-2-amino-ethyl acrylate and methacrylate, (3) $R_{11}-\underset{\underset{O}{\|}}{C}-O-CH=CH_2$ (20)

in which $R_{11}$ represents a linear or branched alkyl radical having 1 to 16 carbon atoms or a phenyl radical, and preferably vinyl acetate, vinyl propionate, vinyl butyrate, vinyl laurate, vinyl stearate, vinyl pivolate, vinyl neoheptanoate, vinyl neooctanoate, vinyl neodecanoate, vinyl 2,2,4,4-tetramethyl-valerate, vinyl 2-isopropyl-2,3-dimethyl-butyrate and vinyl benzoate.

(4) $R_{12}-CH=\underset{\underset{R_{13}}{|}}{C}-(CH_2)_s-COOR'$ (21)

in which R′ is an alkyl radical having 1 to 3 carbon atoms and s is 0 or 1, and preferably dimethyl maleate or diethyl maleate, dimethyl itaconate or diethyl itaconate, and (5)
$CH_2=CH-O-R_{14}$ (22)

in which $R_{14}$ represents a saturated linear or branched alkyl radical having 1 to 17 carbon atoms, and preferably methyl vinyl ether, butyl vinyl ether, isopropyl vinyl ether, octyl vinyl ether, dodecyl vinyl ether and octadecyl vinyl ether.

According to a third preferred embodiment, these copolymers can also be tetrapolymers, pentapolymers or higher copolymers which result from the copolymerisation of more than one monomer of the formula (15) and (16) and more than one monomer of group (c) in the presence of styrene or of another monomer, such as those of the formula (18) to (22) above.

TYPE B: The polymers of this type which result from the copolymerisation of (a) at least one monomer of the formula (15), (b) at least one monomer of the formula (23)

$R_{15}-CH=\underset{\underset{R_{16}}{|}}{C}-(CH_2)_p-CONH_2$ (23)

in which p is 0 or 1 and $R_{15}$ denotes H or COOH and $R_{16}$ denotes H or $CH_3$ when p is 0, and $R_{15}$ denotes H and $R_{16}$ denotes COOH when p=1, in particular acrylamide, methacrylamide, maleamic acid and itaconamic acid, and (c) at least one monomer taken from the group comprising maleic anhydride and the monomers of the formulae (16) and (17).

According to a further variant, the copolymers of type B result from the copolymerization of a monomer (15), a monomer (23), a monomer of group (c) and a monomer chosen from amongst styrene, N-vinylpyrrolidone and the monomers of the formulae (18), (19), (20) and (22), defined above, and (24).

$\underset{\underset{CH-COOR_{17}}{\|}}{CH-COOR_{17}}$ (24)

in which $R_{17}$ represents an alkyl radical having 1 to 3 carbon atoms.

These copolymers have, preferably, a molecular weight of 1,000 to 500,000 and, more particularly, a molecular weight of 2,000 to 200,000.

In a particular embodiment, these copolymers are crosslinked with a crosslinking agent of the type defined in paragraph 3, in a proportion of 0.01 to 2% by weight, relative to the total weight of the monomers reacted.

Free carboxylic acid functional groups can be neutralized with at least one organic base, as is indicated in paragraph 3.

Neutralisation is generally carried out in a molar proportion of between 10 and 150%.

These copolymers can be prepared by copolymerization in solution in an organic solvent such as alcohols, esters, ketones or hydrocarbons.

Amongst these solvents, those which may be mentioned are, in particular: methanol, isopropanol, ethanol, ethyl acetate, ethyl methyl ketone and benzene.

The copolymerization can also take place in suspension or in emulsion in an inert solvent, such as water.

The copolymerization can also take place in bulk.

These polymerizations can be carried out in the presence of a polymerization catalyst which provides free radicals, such as benzoyl peroxide, lauroyl peroxide, azo-bis-isobutyronitrile, hydrogen peroxide and various redox couples such as- $(NH_4)_4S_2O_8$, $FeCl_2$.

The catalyst concentration is generally from 0.2 to 10% by weight, relative to the monomers reacted and as a function of the molecular weight of the copolymers which it is desired to obtain.

Polymers of this type are described in U.S. Pat. Applications 783,631 and 783,632, now abandoned, both filed Apr. 1, 1977 which are hereby included by reference.

8. The non-crosslinked water-soluble polymers of acrylic acid or methacrylic acid or crotonic acid and copolymers of these monomers with a monoethylenically unsaturated monomer, such as ethylene, vinylbenzene, vinyl acetate, vinyl methyl ether and acrylamide and their water-soluble salts.

9. The terpolymers of vinyl acetate, crotonic acid and the vinyl ester of a saturated aliphatic monocarboxylic acid which is branched in the alpha-position and has at least 5 carbon atoms in the carboxylic radical.

These branched esters are derived, in particular, from an acid of the formula:

$R_3-\underset{\underset{R_2}{|}}{\overset{\overset{R_1}{|}}{C}}-\overset{\overset{O}{\|}}{C}-OH$ in which $R_1$ and $R_2$ are an alkyl radical and $R_3$ denotes H or an alkyl, alkaryl, aralkyl or aryl radical.

Polymers of this type are described in French Pat. No. 1,564,110, which is hereby included by reference.

Amongst these polymers, the polymer sold under the designation 28-29-30 by Messrs. National Starch may be mentioned.

10. The tetrapolymers of the type described in French Pat. No. 2,062,801, which comprise about 70 to 80% of N-t-butylacrylamide or N-isopropylacrylamide, about 5 to 15% of acrylamide or methacrylamide, about 5 to 15% of N-vinylpyrrolidone and about 1 to 10% of acrylic acid or methacrylic acid, the percentages being by weight relative to the total weight of the composition. A particularly preferred polymer is that which is sold under the name Quadramer 5 by Messrs. American Cyanamid and which is a N-t-butylacrylamide/acrylamide/acrylic acid and N-vinylpyrrolidone copolymer.

11. The homopolymers of acrylic acid crosslinked with the aid of a polyfunctional agent, such as the products sold under the name CARBOPOL 934, 934P, 940, 941, 960 and 961 by Messrs. Goodrich Chemicals.

12. The copolymers of acrylic acid or methacrylic acid, optionally mixed with homopolymers of the type 11., such as the products sold under the name VERSICOL E or K by Messrs. ALLIED COLLOID, ULTRAHOLD 8 proposed by Messrs. CIBA-GEIGY and the copolymers of the sodium salt of acrylic acid and acrylamide, sold under the name RETEN 421, 423 or 425 by Messrs. HERCULES.

13. The polymers containing an ethylene-α,β-dicarboxylic acid unit, which is optionally monoesterified, such as the copolymers which result from the copolymerization of a compound which can be copolymerized and which contains a >C=CH$_2$ group with a compound of the formula:

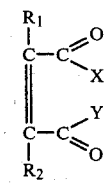

in which R$_1$ and R$_2$ independently of one another denote hydrogen, halogen, a sulphonic acid group, alkyl, aryl or aralkyl and X and Y denote OH, O-alkyl, O-aryl or halogen, or X and Y together denote O.

Compounds of this type which can be used are, for example, the ethylene-α,β-dicarboxylic acids such as maleic acid fumaric acid, itaconic acid, citraconic acid or phenylmaleic acid, or the formula:

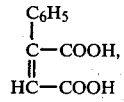

and also benzylmaleic acid, dibenzylmaleic acid and ethylmaleic acid, or an anhydride of such an acid such as maleic anhydride, as well as further derivatives such as the esters or the acid chlorides.

Examples of compounds which can be polymerized and which contain a >C=CH$_2$ group which may be mentioned are vinyl esters, vinyl ethers, vinyl halides, phenylvinyl derivatives such as styrene, acrylic acid and its esters and the esters of cinnamic acid.

These polymers are described in U.S. Pat. No. 2,047,398, which is hereby included by reference.

These copolymers can be optionally esterified. Particularly valuable compounds are cited in U.S. Pat. No. 2,723,248 and U.S. Pat. No. 2,102,113, which are hereby included by reference, and contain the structural unit:

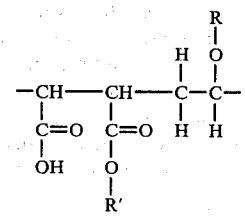

wherein R represents an alkyl group having 1 to 4 carbon atoms, such as, for example, methyl, ethyl, propyl, isopropyl, butyl and isobutyl; and R' represents an alkyl group having 1 to 8 carbon atoms, for example methyl, ethyl, propyl, butyl, isobutyl, pentyl, hexyl, heptyl, octyl and isooctyl.

Further polymers of this type, which can be used according to the invention, are copolymers of maleic anhydride and an olefine having 2 to 4 carbon atoms, which are partially esterified (50-70%) by an alcohol having 1 to 4 carbon atoms, such as those described in British Pat. No. 839,805, which is hereby included by reference.

The copolymers which result from the copolymerisation of: (a) an unsaturated acid anhydride, such as maleic anhydride, citraconic anhydride or itaconic anhydride, and (b) an allyl or methallyl ester, such as allyl or methallyl acetate, propionate, butyrate, hexanoate, octanoate, dodecanoate, octadecanoate, pivalate, neoheptanoate, neooctanoate, neodecanoate, 2-ethylhexanoate, 2,2,4,4-tetramethyl-valerate and 2-isopropyl-2,3-dimethyl-butrate. The anhydride groups are either monoesterified with the aid of an aliphatic alcohol, such as methanol, ethanol, propanol, isopropanol and n-butanol, or amidated with the aid of an aliphatic, cyclic or heterocyclic amine, such as propylamine, isopropylamine, butylamine, dibutylamine, hexylamine, dodecylamine, morpholine, piperidine, pyrrolidine and N-methylpiperazine. Furthermore, the terpolymers which result from the copolymerization of the monomers of paragraphs (a) and (b) above with an acrylamide or methacrylamide, such as N-(tertiary butyl)-acrylamide, N-octyl-acrylamide, N-decyl-acrylamide, N-dodecyl-acrylamide, N-[1-(1,1-dimethyl)-propyl]-acrylamide, N-[1-(1,1-dimethyl)-butyl]-acrylamide, N-[1-(1,1-dimethyl)-pentyl]-acrylamide and also the corresponding methacrylamides, the anhydride groups being esterified or amidated as indicated above. The copolymer can optionally also be copolymerised with α-olefines, such as 1-propene, 1-butene, 1-hexene, 1-dodecene, 1-hexadecene and 1-octadecene; vinyl ethers, such as methyl vinyl ether, ethyl vinyl ether, propyl vinyl ether, isopropyl vinyl ether, butyl vinyl ether, hexyl vinyl ether, dodecyl vinyl ether, hexadecyl vinyl ether and octadecyl vinyl ether; acrylic or methacrylic acid esters, such as methyl acrylate and methacrylate, ethyl acrylate and methacrylate, propyl acrylate and methacrylate, isopropyl acrylate and methacrylate, butyl acrylate and methacrylate, tertiary butyl acrylate and methacrylate, hexyl acrylate and methacrylate, octyl acrylate and methacrylate, decyl acrylate and methacrylate, dodecyl acrylate and methacrylate, octadecyl acrylate and methacrylate and N,N-dimethylamino-2-ethyl acrylate and methacrylate; 2,3-dihydroxypropyl- and ω-methyl- or -ethyl-polyethylene glycol, and optionally acrylic acid or methacrylic acid or N-vinylpyrrolidone for the terpolymers. Polymers of this type are described in French Patent Applications 76/13,929 and 76/20,917, which are hereby included by reference.

Further polymers which may be mentioned are those derived from the maleic and itaconic acids or anhydrides mentioned above, and copolymers of these monomers with a monoethylenically unsaturated monomer, such as ethylene, vinylbenzene, vinyl acetate, vinyl methyl ether or acrylamide, which are optionally hydrolyzed.

Amongst these polymers, those which are more particularly preferred are the products sold under the names Gantrez AN 119, 139, 149 and 169, which are copolymers of maleic anhydride and methyl vinyl ether (1:1), and Gantrez ES 225, 335, 425 and 435, which are, respectively, the monoethyl ester, monoisopropyl ester and monobutyl ester of poly(methyl vinyl ether/maleic acid), sold by Messrs. General Anilin, and EMA 1325 which is sold by Messrs. MONSANTO and is n-butyl-(poly)ethylene maleate.

Further anionic polymers which can be used according to the invention are:

14. The polyacrylamides which contain carboxylate groups, such as the product sold under the name Cyanamer A 370, by Messrs. American Cyanamid.

15. The copolymers of acrylic or methacrylic acid in the form of an alkali metal salt thereof, such as the sodium salt thereof, and vinyl alcohol, such as the product sold under the name Hydagen F by Messrs. Henkel.

16. The copolymers of vinyl acetate/crotonic acid with acrylic or methacrylic acid esters or an alkyl vinyl ether, such as described in French Pat. No. 1,472,926.

17. The copolymers of vinyl acetate/crotonic acid and at least one further monomer chosen from amongst long carbon chain vinyl, allyl and methallyl esters, such as are described in French Pat. No. 1,517,743.

18. The copolymers which consist of 40 to 90% of vinylpyrrolidone, 40 to 5% of a monomer of a vinyl ester and 20 to 30% of an unsaturated carboxylic acid, such as are described in French Pat. No. 2,042,522.

19. The colored polymers based on maleic anhydride, such as are described especially in French Pat. Nos. 1,498,464 and 1,517,862.

Amongst the anionic polymers derived from a carboxylic acid, those which are preferred are, on the one hand, the derivatives of crotonic acid and, in particular, the polymers containing at least one monomer other than vinyl acetate and optionally crosslinked graft polymers and, on the other hand, the derivatives of acrylic or methacrylic acid.

A further category of anionic polymers gives particularly advantageous results and comprises the polymers defined in paragraph 13.

In one embodiment of the invention, it is possible in certain cases to fix the anionic polymer onto the hair by first forming a complex with the cationic polymer. Thus, it is possible to use either complexes formed at the moment of mixing or complexes which have previously been prepared and which, in some cases, are sold in this form.

Complexes which may be mentioned by way of example are those which are also called polysels and result from the complexing of one of the cationic polymers with any one of the anionic polymers defined above. Preferred complexes are those which result from complexing a strongly cationic polymer, such as the cyclopolymers defined in paragraph 2 or the quaternary polymers of paragraph 5, and an anionic polymer of the type defined above in stoichiometric proportions.

Particularly preferred complexes are those which result from complexing cationic polymers containing $G_1$, $G_2$, $G_3$, $G_4$, $G_5$, $G_6$, $G_7$, $G_8$, $G_9$ or $G_{10}$ structural units or the structural unit:

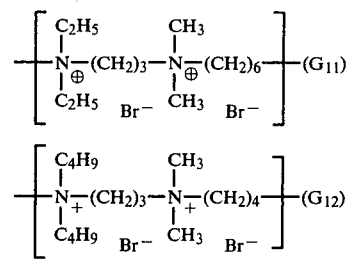

with anionic polymers, such as the salts of polystyrenesulphonic acids, such as the products sold under the name Flexan defined above, the polymers derived from crotonic acid, such as the terpolymer of crotonic acid/vinyl acetate and polyethylene glycol defined in paragraph 2, the terpolymers of vinyl acetate, crotonic acid and a vinyl ester defined in paragraph 8, such as the polymer designated 28-29-30, and the sodium salt of carboxymethylcellulose.

Further polysel complexes which can be used according to the invention are those described in French Pat. Nos. 2,251,843 and 2,198,976, the disclosure of which is hereby incorporated by reference.

The complexes which have been prepared in advance are used for the purposes of the invention by preparing a solution thereof, generally with the aid of a surface-active agent, such as those mentioned further below.

The compositions of the present invention may contain as well as the combination of cationic polymer and anionic polymer, a non-ionic or amphoteric polymer.

Amongst the amphoteric polymers, those which may be more particularly mentioned are the polymers which result from the alkylation of the crosslinked polyaminoamides defined in paragraph 8 and 9 of the description of the cationic polymers, and the alkylating agent can be acrylic acid, chloroacetic acid or an alkanesultone, such as propanesultone or butanesultone. Examples which may be mentioned are polymer K IX, which results from the alkylation of polymer K Ia with sodium chloroacetate, and K X, which results from the alkylation of polymer K Ia with propanesultone.

The compositions according to the present invention can be prepared in a conventional manner in order to obtain a mixture comprising at least one cationic polymer and at least one anionic polymer in an aqueous medium.

Neutralization of polymers which are not readily soluble as such in an aqueous medium can be carried out, especially before mixing, in order to obtain the combination according to the present invention.

As mentioned above, it will be necessary in certain cases, when the combination according to the present invention results in a precipitate, to add a solubilizing agent, preferably chosen from amongst surface-active agents and cosmetically acceptable solvents.

Accordingly, the present invention also provides a cosmetic composition which is essentially characterized in that it contains at least one cationic polymer, at least one anionic polymer, such as those defined above, and at least one solubilizing agent.

The solubilizing agents used according to the present invention can be anionic, cationic, non-ionic or ampho- teric surface-active agents, used on their own or as a mixture.

Amongst the anionic surface-active agents, those which may be mentioned in particular are the following, as well as mixtures thereof: the alkali metal salts, magnesium salts, ammonium salts, amine salts or aminoalcohol salts of the following compounds: alkyl sulphates, alkyl ether-sulphates in which the alkyl radical is a linear chain containing 12 to 18 carbon atoms, alkylamide sulphates and ether-sulphates containing linear chains having 12 to 18 carbon atoms, alkaryl polyether-sulphates and monoglyceride sulphates, alkylsulphonates in which the alkyl radical is a linear chain containing 12 to 18 carbon atoms, alkarylsulphonates, and α-olefine-sulphonates containing linear chains having 12 to 18 carbon atoms, secondary n-alkanesulphonates, mono- or di-alkylsulphosuccinates, alkyl ether-sulphosuccinates, and alkylamide-sulphosuccinates in which the alkyl radical consists of a linear chain having, preferably, 12 to 18 carbon atoms, alkyl sulphosuccinamates in which the alkyl radical has a linear chain containing 12 to 18 carbon atoms, alkyl sulphoacetates in which the alkyl radical contains a linear chain having 12 to 18 carbon atoms, alkylpolyglycerol carboxylates, alkyl phosphates, and alkyl ethyl-phosphates in which the alkyl radical has a chain of 12 to 18 carbon atoms, alkyl sarcosinates, alkyl polypeptides, alkylamidopolypeptides, alkyl isothionates, alkyl taurates in which the alkyl radical has a chain of 12 to 18 carbon atoms, and fatty acids such as oleic acid, ricinoleic acid, palmitic acid, stearic acid, capric acid, lauric acid, myristic acid, arachic acid, behenic acid and isostearic acid, lauroyl-keratinic acid, copra fatty acid or hydrogenated copra fatty acid and carboxylic acids of polyglycol ethers corresponding to the formula:

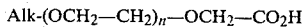
Alk-(OCH$_2$—CH$_2$)$_n$—OCH$_2$—CO$_2$H wherein the substituent Alk corresponds to a linear chain having 12 to 18 carbon atoms and wherein n is an integer of 5 to 15, these compounds being in the form of the free acid or of the salts thereof mentioned above.

The more particularly preferred surface-active agents are sodium lauryl-sulphate, ammonium lauryl-sulphate, sodium cetyl stearyl-sulphate, triethanolamine cetyl stearyl-sulphate, monoethanolamine lauryl-sulphate, triethanolamine lauryl-sulphate, the sodium salt of a sulphate half-ester of an ether (containing 2.2 mols of ethylene oxide for example) obtained by oxyethyleneation of lauryl alcohol and the monoethanolamine salt of a sulphate half-ester of an ether (containing 2.4 mols of ethylene oxide for example) obtained by oxyethyleneation of lauryl alcohol, tridecyl-heptaoxyethylene-carboxylic acid or its sodium salt, and the compound of the formula:

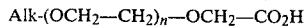
Alk-(OCH$_2$—CH$_2$)$_n$—OCH$_2$—CO$_2$H wherein Alk signifies a mixture of lauric and myristic acid radicals and n is 10, the triethanolamide salt of lauroyl-keratinic acid, sodium lauryl-monoethanolamine-sulphosuccinate, the hydroxyethylamide of sulphated copra fatty acid, sodium lauroylsarcosinate, the sodium hemisulphosuccinate of oxyethyleneated lauryl alcohol, the sodium salt of an olefine-sulphonate, the triethanolamine salt of the condensation product of copra acids with a hydrolysis product of animal proteins, a C$_{12}$-C$_{14}$ alcohol oxyethyleneated with 10 mols of carboxymethylated ethylene oxide, and the n-alkanesulphonates.

Amongst the cationic surface-active agents which can be used, in their own or as a mixture, those which may be mentioned in particular are fatty amine salts such as acetates of alkylamines, quaternary ammonium salts such as alkyldimethylbenzylammonium chlorides or bromides, alkyltrimethylammonium chlorides or bromides, alkyldimethylhydroxyethylammonium chlorides or bromides, dimethyldistearylammonium chloride or bromide, dimethyldilaurylammonium chloride or bromide, acetyldimethyldodecylammonium chloride and alkylamidoethyltrimethylammonium methosulphates, the lactates of N,N-dimethylamino-(or N,N-diethylamino)-polyoxyethylcarboxylates containing 4 mols of ethylene oxide, alkylpyridinium salts such as 1-(2-hydroxyethyl)-carbamoylmethylpyridinium chloride and N-[lauryl-colamino-formylmethyl]pyridinium chloride, imidazoline derivatives such as the alkyl imidazolines, and cationic compounds corresponding to the formula:

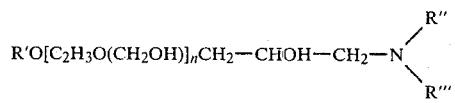
$$R'O[C_2H_3O(CH_2OH)]_n CH_2—CHOH—CH_2—N\begin{matrix}R''\\R'''\end{matrix}$$

in which R' denotes a saturated or unsaturated linear or branched alkyl radical or an alkaryl radical having a linear or branched alkyl chain containing 8 to 22 carbon atoms and R" and R''' denote independently lower hydroxyalkyl radicals or alkylene radicals which are linked together to form a heterocyclic structure; and n is a number from 0.5 to 10.

Amongst the preferred compounds corresponding to the above formula, those which may be mentioned are those in which (a) R'=C$_{12}$H$_{25}$, n=1 and R"=R'''=β-hydroxyethyl or (b) R'=C$_{12}$H$_{25}$, n=1 and R"=R'''=2-hydroxypropyl.

The alkyl radicals in these compounds preferably have 1 to 22 carbon atoms. Compounds of cationic character may also be mentioned, such as the amine oxides, such as alkyldimethylamine oxides and alkylaminoethyl-dimethylamine oxides.

Amongst the non-ionic surface-active agents which can optionally be used in admixture with the anionic surface-active agents mentioned above, those which may be mentioned are the condensation products of a monoalcohol, an α-diol, an alkylphenol, an amide or a diglycolamide with glycidol, such as, for example, the compounds corresponding to the formula:

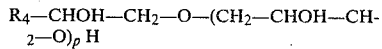
R$_4$—CHOH—CH$_2$—O—(CH$_2$—CHOH—CH$_2$—O)$_p$ H in which R$_4$ denotes an aliphatic, cycloaliphatic or araliphatic radical having, preferably, 7 to 21 carbon atoms, and mixtures thereof, it being possible for the aliphatic chains to contain ether, thioether or hydroxymethylene groups, and wherein p is 1 to 10 inclusive; such as the compounds described in French Pat. No. 2,091,516; or U.S. Pat. Nos. 3,928,224, 3,966,398 and Application Ser. No. 678,030 now U.S. Pat. No. 4,087,466, filed Apr. 19, 1976 the compounds which correspond to the formula:

$$R_5O[C_2H_3O(CH_2OH)]_q H$$

in which $R_5$ denotes an alkyl, alkenyl or alkaryl radical and q has a statistical value of 1 to 10 inclusive; and the compounds which correspond to the formula:

$$R_6CONH-CH_2-CH_2-O-CH_2-CH_2-O[CH_2-CHOH-CH_2-O]_r H$$

in which $R_6$ denotes a linear or branched, saturated or unsaturated aliphatic radical, or a mixture of such radicals, which can optionally contain one or more hydroxyl groups, have 8 to 30 carbon atoms and are of natural or synthetic origin, and r represents an integer or decimal number from 1 to 5 and denotes the mean degree of condensation.

Further compounds of this type are alcohols, alkylphenols and the polyoxyethyleneated or polyglycerolated fatty acids having a linear or branched fatty chain and containing 8 to 18 carbon atoms and most frequently containing 2 to 30 mols of ethylene oxide. The copolymers of ethylene oxide and propylene oxide, the condensation products of ethylene oxide and propylene oxide with fatty alcohols, polyoxyethyleneated fatty amides, polyethoxylated fatty amines, ethanolamides, fatty acid esters of glycol, fatty acid esters of sorbitol and fatty acid esters of sucrose may also be mentioned.

Amongst these non-ionic surface-active agents, those which are more particularly preferred correspond to the formula:

$$R_4-CHOH-CH_2-O-(CH_2-CHOH-CH_2-O)_{\overline{p}}H$$

wherein $R_4$ denotes a mixture of alkyl radicals having 9 to 12 carbon atoms and p has a statistical value of 3.5;

$$R_5-O[C_2H_3O(CH_2OH)]_q H$$

wherein R denotes $C_{12}H_{25}$ and q has a statistical value of 4 to 5; and $$R_6-CONH-CH_2-CH_2-O-CH_2-CH_2O-[CH_2CHOH-CH_2O]_{\overline{r}}H$$

wherein $R_6$ denotes a mixture of radicals derived from lauric acid, myristic acid, oleic acid and copra fatty acid and r has a statistical value of 3 to 4.

The preferred oxyethyleneated or polyglycerolated fatty alcohols are polyoxyethyleneated oleyl alcohol containing 10 mols of ethylene oxide, oxyethyleneated lauryl alcohol containing 12 mols of ethylene oxide, oxyethyleneated cetyl alcohol containing 6 to 10 mols of ethylene oxide, oxyethyleneated cetylstearyl alcohol containing 3 to 10 mols of ethylene oxide, oxyethyleneated stearyl alcohol containing 2,10,15 or 20 mols of ethylene oxide, oxyethyleneated nonylphenol containing 9 mols of ethylene oxide, oxyethyleneated octylphenol containing 5.5 mols of ethylene oxide, polyglycerolated oleyl alcohol containing 4 mols of glycerol and polyoxyethyleneated $C_9$-$C_{15}$ synthetic fatty alcohols containing 3 to 12 mols of ethylene oxide, polyoxyethylene stearyl alcohol containing 50 mols of ethylene oxide, the monolaurate of polyoxyethyleneated sorbitane containing 20 mols of ethylene oxide and the polycondensation products of ethylene oxide and propylene glycol.

Amongst the amphoteric surface-active agents which can be used, those which may be mentioned more particularly are alkylamino mono- and di-propionates, the betaines, such as the N-alkylbetaines, the N-alkylsulphobetaines and the N-alkylamidobetaines, cycloimidinium compounds, such as the alkylimidazolines, and the derivatives of asparagine, such as the N,N-dialkylaminoalkyl-N-2-alkyl (fatty) asparagines. The alkyl group in these surface-active agents preferably denotes a group having 1 to 22 carbon atoms.

Further solubilizing agents used for the purposes of the present invention are cosmetically acceptable solvents, such as monoalcohols, polyalcohols, glycol ethers, glycol esters, esters of fatty acids, and methylene chloride, which can be used on their own or as a mixture.

Amongst the monoalcohols, those which may be mentioned are the lower alkanols having 1 to 4 carbon atoms, such as ethanol, n-propanol, isopropanol, n-butanol, 2-butanol and tertiary butanol; n-amyl alcohol; isoamyl alcohol and hexadecyl alcohol; 1-octyldecan-1-ol; 1-octyldodecan-1-ol; 2-dodecylcetyl alcohol; oleyl alcohol; benzyl alcohol, cyclohexanol, methylcyclohexanol, furfuryl alcohol and phenylethyl alcohol.

Amongst the polyalcohols, those which may be mentioned are the alkylene glycols, such as ethylene glycol, diethylene glycol, propylene glycol, dipropylene glycol, polypropylene glycol, butylene glycol and hexylene glycol; ricinoleyl alcohol and glycerol.

Amongst the glycol ethers, those which are more particularly preferred are the mono-, di- and tri-ethylene glycol monoalkyl ethers, such as, for example, ethylene glycol monomethyl ether, ethylene glycol monoethyl ether, ethylene glycol monobutyl ether, diethylene glycol monomethyl ether and diethylene glycol monoethyl ether; the mono-, di- and tri-propylene glycol monoalkyl ethers, such as propylene glycol monomethyl ether; the butylene glycol monoalkyl ethers and the polyethylene glycol monoalkyl ethers.

Amongst the esters, those which can be used more particularly for the purposes of the invention are: the acetate of ethylene glycol monomethyl ether, the acetate of ethylene glycol monoethyl ether and the esters of fatty acids and lower alcohols, such as isopropyl myristate or isopropyl palmitate.

It is self-evident that the surface-active agents mentioned above can be used not only as solubilizing agents which hinder the formation of a precipitate resulting from the interaction of the cationic polymer and the anionic polymer in the aqueous medium, but also to take advantage, either at the same time as, or independently of, this effect, of their foaming, wetting, detergent, dispersing or emulsifying properties.

The cationic polymers, on their own or in combination with other polymers of this type, are generally present in an amount of 0.01 to 10% and preferably of 0.05 to 5% by weight relative to the total weight of the composition.

The anionic polymers, on their own or in combination with other polymers of this type, are generally present in an amount of 0.01 to 10% and preferably of 0.02 to 5% relative to the total weight of the composition.

The ratio by weight of the cationic polymer to the anionic polymer generally varies from 0.1 to 60, advantageously from 0.4 to 50 and preferably from 0.4 to 20.

When the composition also includes a solubilizing agent (surface-active agent or the cosmetically acceptable solvent), this agent, which can be a single substance or a mixture of two or more such substances, is generally present in an amount of 0.1 to 70% and preferably of 0.5 to 50% of the total weight of the composition.

The ratio of the solubilizing agent to the cationic and anionic polymers varies, preferably, from 0.5 to 200 and more particularly from 0.5 to 50.

The compositions according to the present invention can be used as such in order to treat the hair or the skin or can serve "as a base or carrier" which is included in cosmetic formulations which also contain a suitable proportion of the active product and are intended to be applied to the skin, the hair or the nails in order to protect these against attack by atmospheric agents and actinic rays as well as to promote the action of any other active product intended for the skin, the hair or the nails.

They can contain, in addition to the cationic polymer or polymers and the anionic polymer or polymers, adjuvants customarily used in cosmetics, such as perfumes, colorants, which can serve to colour either the composition itself or the hair or the skin, preservatives, sequestering agents, thickeners, emulsifiers, softening agents, synergistic agents, anionic, cationic, nonionic or amphoteric surface-active agents, non-ionic or amphoteric polymers or foam stabilizers, depending on the intended use.

When the cosmetic compositions are used for the treatment of the hair, they can be, more particularly, in the form of treatment creams which can be applied before or after coloring or bleaching, before or after shampooing or before or after permanent waving, and can also be in the form of coloring products, shampoos, rinsing lotions, to be applied before or after shampooing, before or after colouring or bleaching or before or after permanent waving, or wavesetting lotions, lotions for brushing or restructuring lotions.

When the compositions according to the present invention consist of treatment creams or milks to be applied before or after coloring or bleaching, before or after shampooing or before or after permanent waving, they are essentially formulated on the basis of soaps or fatty alcohols, in the presence of emulsifiers, or on the basis of polyoxyethyleneated or polyglycerolated fatty alcohols.

The soaps can be, for example, naturally occurring or synthetic fatty acids having 12 to 22 carbon atoms, such as lauric acid, myristic acid, palmitic acid, oleic acid, ricinoleic acid, stearic acid and isostearic acid, arachic acid or behenic acid, present at concentrations of, preferably, 10 to 30% by weight, optionally with alkalizing agents, such as sodium hydroxide, potassium hydroxide, ammonia, monoethanolamine, diethanolamine or triethanolamine, singly or as a mixture.

The fatty alcohols which can be used in the creams are naturally occurring or synthetic alcohols generally having 12 to 18 carbon atoms. Amongst these fatty alcohols, those which may be mentioned are, in particular, the alcohols derived from copra fatty acids, tetradecyl alcohol, cetyl alcohol, stearyl alcohol, isostearyl alcohol and hydroxy-stearyl alcohol, generally present at concentrations of 0.5 to 25% in the composition.

The emulsifiers which can be used in the compositions according to the present invention can be the anionic and nonionic surface-active agents mentioned above. The non-ionic emulsifiers are suitably present in amounts of 0.5 to 25% by weight and the oxyethyleneated or polyoxyethyleneated fatty alcohols defined above are preferably used.

The anionic emulsifiers are suitably present in concentrations of 0.5 to 15% by weight. The optionally oxyethyleneated alkyl sulphates defined above are preferably used.

The polyoxyethyleneated or polyglycerolated fatty alcohols consist of fatty alcohols having a linear or branched fatty chain containing, say, 8 to 18 carbon atoms and most frequently containing 2 to 30 mols of ethylene oxide or preferably 2 to 10 or 1 to 10, and preferably 1 to 6, mols of glycerol.

The preferred polyglycerolated fatty alcohols are polyglycerolated stearyl alcohol or cetyl alcohol containing 2 mols of glycerol.

The polyoxyethyleneated or polyglycerolated fatty alcohols are generally present in concentrations of 0.5 to 25% by weight.

These creams can contain, in addition to the polymers, adjuvants customarily used in such compositions, such as fatty amides and fatty alcohols when these are based on soaps.

Amongst the fatty amides, those preferably used are the mono- or di-ethanolamides of acids derived from copra, or of lauric acid, oleic acid or stearic acid, at concentrations of up to 10% by weight, and preferably of 1 to 4% by weight.

The pH of these creams and milks is generally 3 to 9 and preferably 5 to 9.

When the compositions according to the present invention are in the form of coloring creams, they contain, in addition to the cationic polymer or polymers and the anionic polymer or polymers, various other ingredients such as an alkalizing agent and colorants and the adjuvants customarily used, such as antioxidants, and sequestering agents may be added.

The pH of these compositions is, in general, from 9 to 11 and can be adjusted by the addition of an appropriate alkalizing agent to the colour base, such as ammonia, alkylamines, alkanolamines, such as mono-, di- or triethanolamines, triisopropanolamine or mixtures thereof, alkylalkanolamines such as aminomethylpropanol or aminomethylpropanediol, sodium hydroxide or potassium hydroxide, ammonium carbonate, sodium carbonate or potassium carbonate. All these compounds can be used on their own or as a mixture.

The colorants may be oxidation dyestuffs to which direct dyestuffs, such as azo dyestuffs, anthraquinone dyestuffs, nitrobenzene dyestuffs, indamines, indoanilines, indophenols and/or other oxidation dyestuffs, such as the leuco derivatives of these compounds, can be added.

The oxidation dyestuffs are aromatic compounds of the diamine, aminophenol or phenol type. These compounds are not generally dyestuffs in themselves but are converted into dyestuffs by a condensation reaction in the presence of an oxidizing medium such as hydrogen peroxide. Amongst these oxidation dyestuffs, a distinction is made between, on the one hand the bases which are the para- or orthodiamines and aminophenols and, on the other hand, compounds which are termed modifiers or couplers and are meta-derivatives, namely meta-diamines, m-aminophenols, m-diphenols and phenols.

The oxidation bases which are more particularly used are the p-phenylenediamines, which are optionally substituted on the nitrogen atom or on the aromatic nucleus by groups such as alkyl groups having preferably 1 to 4 carbon atoms, hydroxyalkyl groups having preferably 1 to 4 carbon atoms, halogen or alkoxy groups having preferably 2 to 4 carbon atoms. Amongst these compounds, those which may be mentioned more particularly are p-phenylenediamine, p-toluylenediamine, chloro-p-phenylenediamine, p-aminodiphenylamine, o-phenylenediamine, o-toluylenediamine, 2,5-diaminoanisole, o-aminophenol and p-aminophenol and 1-amino-4-(2-methoxyethyl)-amino-benzene.

The couplers which are more particularly used are especially m-phenylenediamine, m-toluylenediamine, 2,4-diaminoanisole, m-aminophenol, pyrocatechol, resorcinol, hydroquinone, α-naphthol, 1,5-dihydroxynaphthalene, 2,6-diaminopyridine and 1-(2-hydroxyethoxy)-2,4-diaminobenzene.

When the compositions according to the present invention constitute shampoos, they contain, in addition to the cationic polymer or polymers and the anionic polymer or polymers, at least one anionic, cationic, non-ionic or amphoteric surface-active agent, such as those defined above.

In these shampoos, the concentration of detergent or surface-active agents is generally from 3 to 50% by weight, relative to the total weight of the composition, and preferably from 3 to 20%; the pH is generally from 3 to 10.

The more particularly preferred shampoos have a pH of 5 to 9.

The compositions according to the invention can also be in the form of lotions which can be hairstyling lotions or setting lotions, which are also termed lotions for brushing, lotions which are not rinsed out and aid wave-setting and lotions which are rinsed out and are also termed rinses.

Setting lotions or lotions for brushing are understood to mean lotions which are applied after shampooing and which aid setting of the head of hair, this setting being carried out on wet hair with the aid of a brush whilst the hair is being dried with the aid of a hand drier.

Lotions which are not rinsed out and aid wave-setting are understood to mean a lotion which is applied after shampooing and before wave-setting; this lotion, which is not removed on rinsing, facilitates the subsequent wave-setting and makes the wave-set last longer.

These lotions comprise, generally in aqueous, alcoholic or aqueous-alcoholic solution, at least one cationic polymer and at least one anionic polymer, such as those defined above. They can also generally contain non-ionic or amphoteric polymers and/or anti-foaming agents.

The lotions which are rinsed out are solutions which are applied before or after coloring, before or after bleaching, before or after permanent waving or before or after shampooing, or between two shampooing stages, in order to produce a conditioning effect on the hair, and which are rinsed out after remaining on the hair for some time.

These compositions can be aqueous or aqueous-alcoholic solutions which optionally contain surface-active agents, or emulsions or gels. These compositions can also be pressurized as an aerosol.

The surface-active agents which can be used in the solutions are essentially the non-ionic or cationic surface-active agents of the type described above for shampoo compositions and are in particular the condensation products of a monoalcohol, an α-diol, an alkylphenol, an amide or a diglycolamide with glycidol, such as, for example, the compounds of the formula:

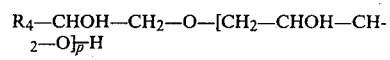

in which $R_4$ denotes an aliphatic, cycloaliphatic or araliphatic radical having 7 to 21 carbon atoms, and mixtures thereof, the aliphatic chains optionally containing ether, thioether or hydroxymethylene groups and p a statistical value ranging from 1 to 10 inclusive; compounds of the formula:

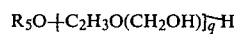

in which $R_5$ denotes an alkyl, alkenyl or alkaryl radical and q denotes a statistical value ranging from 1 to 10 inclusive; and the compounds of the formula:

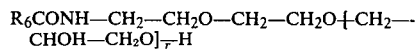

in which $R_6$ is an aliphatic radical which can optionally contain one or more OH groups and has 8 to 30 carbon atoms and r represents an integral or decimal number of 1 to 5.

Amongst these compositions, those which are more particularly preferred for the purposes of the invention contain a non-ionic surface-active agent of the formula:

wherein $R_4$ denotes a mixture of alkyl radicals having 9 to 12 carbon atoms and p has a statistical value of 3.5.

It is also possible to use alcohols, alkylphenols and polyoxyethyleneated or polyglycerolated fatty acids containing a linear fatty chain having 8 to 18 carbon atoms and most frequently containing 2 to 15 mols of ethylene oxide. The concentration of surface-active agents can vary up to, say, 10% and preferably from 0.5 to 7% by weight.

Anionic or amphoteric surface-active agents can be added to these compositions.

When the compositions are in the form of an emulsion, they can be non-ionic or anionic. The non-ionic emulsions consist in the main of a mixture of oils and/or fatty alcohols and polyoxyethyleneated fatty alcohols such as polyoxyethyleneated stearyl or cetyl/stearyl alcohols. Cationic compounds, such as, for example, those defined above, can be added to these compositions.

The anionic emulsions are made up on the basis of soaps. Thus, emulsions which may be mentioned are the emulsion consisting of self-emulsifying glycerol stearate, which is sold under the name IMWITOR 960 K by Messrs. DYNAMIT NOBEL, and the emulsions which consist of a combination of glycerol monostearate with esters of citric acid or with fatty alcohols and lipopeptides or with alkali metal stearates, which are sold under the names LAMEFORM ZEM, PLM and NSM respectively by Messrs. GRUNAU.

When the compositions are in the form of gels, they contain thickeners, in the presence or absence of solvents. The thickeners which can be used include sodium alginate or gum arabic or cellulose derivatives, such as methylcellulose, hydroxymethylcellulose, hydroxyethylcellulose, hydroxypropylcellulose and hydroxypropylmethylcellulose. Thus, it is also possible to achieve thickening of the lotions by means of a mixture of polyethylene glycol and the stearate or distearate of polyethylene glycol or by means of a mixture of phosphoric acid esters and amides.

The concentration of thickeners is generally from 0.5 to 30%, and preferably from 0.5 to 15%, by weight. The pH of the lotions which are rinsed out and are also called rinses is generally from 2 to 9.5.

When the abovementioned compositions are pressurized as an aerosol, propellant gases which can be used include carbon dioxide, nitrogen, nitrous oxide, volatile hydrocarbons, such as butane, isobutane or propane, or preferably chlorinated or fluorinated hydrocarbons, in particular fluorochlorohydrocarbons, such as dichlorodifluoromethane or Freon 12, dichlorotetrafluoroethane, or Freon 114, and trichloromonofluoromethane, or Freon 11. These propellants can be used on their own or in combination; in particular it is possible to employ a mixture of Freon 114-12 in proportions which vary between 40:60 and 80:20. A chlorinated hydrocarbon which may be mentioned is methylene chloride.

The compositions according to the present invention can consist of restructuring lotions and contain products which strengthen the keratin chain of the hair. Products used for this purpose are those belonging to the category of methylolated derivatives and especially those of the type described in French Pat. Nos. 1,527,085 and 1,519,979.

The combination according to the invention can, finally, be used in compositions which are intended to straighten or wave the hair and which contain, in addition to the polymers, reducing agents such as sulphites and thioglycollates used conjointly with the neutralizing compositions.

The perfumes which can be used in these compositions are the cosmetically acceptable perfumes and they are present in amounts which preferably vary from 0.1 to 0.5% by weight.

The colorants which are intended to confer a color to the compositions according to the invention are generally present in an amount from 0.001 to 0.5% by weight.

When the compositions according to the present invention are prepared for application to the skin, they can be in the form of aftershave lotions or toilet water or shaving foams.

The aftershave lotions and toilet waters are in the form of an aqueous-alcoholic solution which contain, preferably, a lower alkanol (i.e.a having 1 to 4 carbon atoms), preferably ethanol or isopropanol, and comprise the adjuvants customarily used, such as softening agents, cicatrizing agents and perfumes.

In the case of toilet waters, the perfumes are usually present in amounts which are greater than those mentioned above and can be up to, say, 3% by weight, depending on their nature.

When the composition is in the form of a shaving foam, it generally contains soaps, optionally admixed with fatty acids, foam stabilizers and softeners, such as glycerol.

It can be packed in an aerosol device in the presence of propellant gases, in accordance with well-known techniques.

As mentioned above, the compositions defined above can also serve as a carrier or base in the form of an aqueous or aqueous-alcoholic solution or a cream, gel, dispersion or emulsion, for cosmetic formulations for treatment of the skin.

These compositions can also be used in the treatment of the nails, in which case the combination according to the invention not only enables the anionic polymers to be fixed to the nails but, above, enables the nails to be strengthened and rendered more glossy; the compositions are used in the presence of solvents and other ingredients customarily used.

These compositions can, finally, be used in the treatment of other keratin materials, such as wool.

The various adjuvants which can be used in these compositions are well-known in the state of the art and are similar to those more particularly described for the compositions for the treatment of the hair.

The compositions according to the invention can be packed and stored in different ways, as indicated above. One advantageous embodiment consists, however, in packing in the form of a lyophilized product since this has the advantage of ensuring that the compositions according to the invention keep better.

This mode of procedure, moreover, enables the combination according to the invention to be prepared under conditions different to that customarily used for good anchoring on keratin materials, such as at a different pH, these conditions preventing undesired precipitation. This procedure also enables the deterioration of certain combinations by ageing (such as yellowing) to be prevented.

Remarkable results can be obtained for compositions which are to be rinsed out and contain a cationic polymer chosen from amongst the optionally crosslinked polyamino-amides, such as are defined in paragraphs 7, 8, 9, 10 and 11, combined with the various anionic polymers; the more particularly preferred combinations are those with the polymer containing a maleic anhydride unit, of paragraph 13, the polymers containing a crotonic acid unit which are grafted and optionally crosslinked or contain more than one other monomer different from vinyl acetate, the polymers containing an acrylic acid or methacrylic acid unit and the sulphonic acid derivatives.

A further preferred embodiment of the invention is the combination of a cationic polymer chosen from amongst the polyalkylene-amines defined in paragraph 12 with any one of the anionic polymers and preferably those indicated above.

Particularly advantageous results can be obtained by combining the preferred combinations defined above with weakly anionic or non-ionic surface-active agents, or a mixture of the two. "Weakly anionic surface-active agents" are understood as meaning the carboxylic derivatives such as alkyl polypeptidates, the salts of lipoaminoacids, the alkyl-polyglycerylcarboxylates and the carboxylic acids derived from polyglycol ether. The more particularly preferred non-ionic surface-active agents are the compounds of the formula:

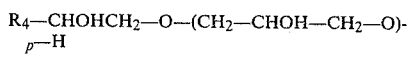

defined above.

An advantageous embodiment of the invention comprises the combination of a strongly substantive cationic polymer, for example a cyclopolymer defined in paragraph 2 or a quaternary polymer of paragraph 5, with any anionic polymer and preferably with the preferred anionic polymers indicated above.

A valuable means of carrying out this embodiment comprises the combination, with the polymers defined above, of an anionic surface-active agent and, preferably, the sulphates, sulphonates, succinates, succinamates, acetates, phosphates and sarcosinates defined above.

The combination according to the invention also enables valuable results to be obtained with cationic polymers of low substantivity, such as the cellulose ether polymers of paragraph 1, the polymers containing acrylic or methacrylic acid structural units, described in French Pat. No. 2,189,434, of paragraph 3, or the derivatives of vinylpyrrolidone, of paragraph 6 and of paragraph 13, with any one of the anionic polymers and preferably with those containing, in their chain, sulphonic acid, crotonic acid or acrylic or methacrylic acid structural units and structural units of maleic anhydride derivatives. These combinations are of value in particular for reducing the electrostatic charge on the hair.

The cationic polymers of the type described in paragraph 4, which contain, in their chains, a radical possessing two amine functional groups, such as piperazinyl, enable valuable holding properties of the hair to be obtained when the polymer is used in combination with an anionic polymer, in a composition intended to be rinsed out.

The anionic linear, non-crosslinked polymers preferred for use in this invention are those which contain an acrylic or methacrylic acid structural unit, an optionally monoesterified or hydrolyzed maleic anhydride structural unit or a grafted and optionally crosslinked crotonic acid structural unit or contain units derived from more than one monomer other than vinyl acetate, with any one of the cationic polymers mentioned above. The results are particularly significant in respect of the softness to the touch and volume of the head of hair.

Amongst the compositions intended to be rinsed out, those which are of particular value and which give surprising results are the shampoos which necessarily contain a non-ionic or weakly anionic surface-active agent, or a mixture thereof, these surface-active agents being present in the proportions indicated above.

A further valuable embodiment is the formulation as compositions intended to be rinsed out, which preferably contain a non-ionic or weakly anionic surface-active agent.

When the anionic polymer is used in compositions which are not intended to be rinsed out, such as a setting lotion, a waveset-promoting lotion, an aftershave lotion, a toilet water or a composition for treatment of the nails, particularly surprising results are obtained with the compositions which contain, as the anionic polymer, the polymers defined in paragraph 13 or acrylic or methacrylic acid derivatives in combination with any cationic polymer and preferably the crosslinked polyamino-amides, the polyalkyleneamines, the cyclopolymers and quaternized ionic polymers.

Valuable results are also obtained with the copolymers of crotonic acid containing units derived from at least one monomer other than vinyl acetate, or the grafted and/or crosslinked derivatives, thereof or allyloxyacetic or vinylacetic acid, with any one of the cationic polymers and preferably those mentioned above.

Further valuable combinations according to the invention are those consisting of the use of a vinyl acetate/crotonic acid bipolymer, as the anionic polymer, with cationic polymers chosen from amongst the cellulose ether derivatives of paragraph 1, the cyclopolymers, of paragraph 2, the homo- or co-polymers of paragraph 3, the vinylpyrrolidone derivatives of paragraph 6, the polyalkyleneamines of paragraph 12, the polymers which contain vinylpyridine or vinylpyridinium units in their chain, ureaformaldehyde resins, the condensation products of a polyamine and epichlorohydrin, the vinyl-benzylammonium homopolymers or copolymers, the quaternary polyureylene compounds and the colouring polymers.

The compositions according to the invention which are intended, especially, for treatment of the hair, can be applied by a two-stage process.

This process is essentially characterized in that a first composition which contains an anionic polymer and a cationic polymer of the type defined above and has been adjusted to a pH such as to prevent precipitation of the combination of the anionic polymer and the cationic polymer is applied in a first stage, and in that a second composition which has a pH such that the two polymers precipitate on the hair when the second composition is applied to the fibres is applied in a second stage and without intermediate rinsing.

According to a preferred embodiment, the first composition has a pH of 8 to 12 and the second composition has a pH chosen such that the pH will be less than 8 after mixing with the first composition on the hair.

This embodiment of the process according to the invention in particular makes it possible to use combinations of cationic and anionic polymers which precipitate under pH conditions which give rise to maximum deposition. In this case, it is possible to apply these combinations at a different pH which prevents precipitation and to bring about precipitation on the hair in order to obtain optimum deposition of the anionic polymers, which is the desired object of the invention.

The alkalizing agents which can be used in the first composition are organic or inorganic bases of the type mentioned above. The acidifying agents which can be used in the second composition are organic or inorganic acids, such as hydrochloric acid, citric acid, lactic acid, tartaric acid and phosphoric acid.

It is also possible to apply the first composition to the hair at an acid pH and then to adjust the pH, by means of a second composition containing a base, on the hair in order to bring about precipitation of the polymers on the hair.

Particularly valuable results are obtained with, in the first case, crosslinked polyamino-amides of the type described in paragraphs 7, 8, 9, 10 and 11 as cationic polymers, and crotonic acid derivatives as anionic polymers and with, in the second case, the crosslinked polyamino-amides defined above, combined with maleic anhydride derivatives.

The fixing of the anionic polymers to the keratin materials by means of a cationic polymer according to the invention can be effected according to a two-stage process which consists in applying, preferably onto the keratin fibres, a first composition containing a cationic polymer of the type defined above and then, after rinsing or without rinsing, applying a composition containing an anionic polymer, this treatment preferably being followed by rinsing. In this case the cationic polymer/anionic polymer combination is formed on the fibres.

This process has, in particular, certain advantages in the processes for washing hair. Thus, it is possible first of all to apply an aqueous solution of a cationic polymer and then a shampoo containing the anionic polymer. Significant results have been obtained using a crosslinked polyamino-amide in the first composition and a derivative of maleic anhydride or a derivative of polystyrenesulphonic acid, defined above, combined with anionic or non-ionic surface-active agents, in the second composition.

According to another embodiment, two shampoos can be applied successively, the first containing the cationic polymer and the second containing the anionic polymer. Cationic polymers which give advantageous results are, preferably, cross-linked polyamino-amides of the type defined in paragraphs 8, 9, 10 and 11, the quaternary polymers defined in paragraph 5 and the cyclopolymers defined in paragraph 2, with anionic polymers chosen from amongst the derivatives of maleic anhydride and the terpolymers based on crotonic acid and the copolymers of acrylic or methacrylic acid, such as those defined in paragraphs 2, 8, 11 and 12.

Further combinations which give advantageous results in a two-stage process are those which consist in using, in a first composition, a cationic polymer, derived from acrylic or methacrylic acid, of the type defined in paragraph 3, and, as the anionic polymer, derivatives of acrylic or methacrylic acid defined in paragraph 11, and in particular, the polymers sold under the names Reten or Catrex, or those which consist in using, in the first composition, as the cationic polymer, a derivative of a cellulose ether, such as defined in paragraph 1, the polymers defined in paragraph 4, the polyethyleneamines of the type cited in paragraph 12 or polymers which contain, in their chain, vinylpyridine or vinylpiperidinium units and are defined in paragraph 13, with the anionic polymers mentioned above.

This application gives good results when anionic or non-ionic surface-active agents are used in the compositions.

It is possible, according to an advantageous embodiment of this process, to vary the pH of the different compositions in order to give the best conditions for the deposition of each polymer and to bring about anchoring of the anionic polymer on the fibres by means of the cationic polymer.

A further embodiment of the invention consists in the application, in a first stage, of a composition containing a cationic polymer and a reducing agent and, in a second stage, the application of a neutralizing composition containing an anionic polymer, in order to straighten or wave the hair.

The present invention accordingly also provides a process for fixing anionic polymers on keratin material by combining the latter with a cationic polymer.

This fixing is remarkable in processes which include a rinsing stage after the treatment by the polymers.

A particularly valuable variant of the invention is, thus, the use of the compositions according to the invention in a process for the treatment of keratin fibres, such as hair, which process consists in applying this composition and then carrying out rinsing.

When the composition is in a lyophilized form, the process according to the invention consists in introducing the lyophilized product, just before use, into the cosmetic carrier, which can contain the various adjuvants mentioned above, and applying the composition thus prepared to the keratin material. This mode of procedure is of value in particular when the polymers have a tendency to yellow on storage in solution and when it is desired to apply them to a keratin material where such a phenomenon is undesirable, such as the skin or the nails.

The examples which follow are intended to illustrate the invention, without restricting it in any way.

In the Examples which follow and which further illustrate the present invention, all the polymers are expressed as active material i.e. the amounts indicated relate to polymers containing 100% of active material. The amounts of surface-active agent are expressed as a percentage of active material.

The anionic polymers used must in certain cases be neutralised. This is so if the following polymers are used: resin 26:13.14. resin TV 242, $P_1$, $P_2$ and $P_3$, Quadramer 5, Gantrez ES225, Gantrez 425, resin 28.29.30 and EMA 1325; it is to be understood that they have been neutralized to an extent which can range up to 100% (in order to render them soluble in the aqueous medium) by means of alkalizing agents such as ammonia, alkylamines, alkanolamines, such as monoethanolamine, diethanolamine, triethanolamine or triisopropanolamine, or mixtures, alkylalkanolamines such as aminomethylpropanol and aminomethylpropanediol, sodium hydroxide or potassium hydroxide or sodium carbonate or potassium carbonate. The bases which were used, by way of example, for neutralizing the abovementioned polymers were 2-amino-2-methylpropanol, 2-amino-1,3-propanediol, triethanolamine, triisopropanolamine and sodium hydroxide. Neutralization is taken to a pH value of from 7 to 10 and most frequently of from 7 to 9.

The anionic polymers can also be solubilized beforehand in an anionic surface-active agent or a solvent of the type mentioned above, in that case, neutralisation is superfluous.

The polymers can also be used together with plasticizing agents such as methylcellosolve, methyl, dimethyl, diethyl, dibutyl and dioctyl phthalate, propylene, hexylene, polyethylene and other polyalkylene glycols, propylene glycol dipelargonate, glycolpolysiloxanes, glycerol triacetate, lauryl lactate, diethylene glycol monooleate, decyl oleate, octyl sebacate, acetyl tributyl citrate, isopropyl myristate, ethyl phthalyl-ethyl glycollate and methyl phthalyl-ethyl glycollate.

EXAMPLE 1

A shampoo having the following composition is prepared:

| | | |
|---|---|---|
| anionic polymer called Flexan 500 | 0.4 | g |
| cationic polymer containing K IIIa units | 0.6 | g |
| surface-active agent called AST 1214 | 10 | g |
| copra diethanolamide | 3 | g |
| The pH is adjusted to 7.5 with lactic acid: | | |
| water, q.s.p. | 100 | g |

This composition, when applied to dirty and wet hair, produces, after impregnation, a soft foam.

The wet hair is light, with an impression of more abundant hair. This impression persists after washing.

When dry, the hair is bulky, springy and disciplined, with little electrostatic charge. The hair has more body and a wave-set carried out on such hair lasts well.

Similar results are obtained with the compositions illustrated in Table I below, when these are applied in a similar manner to that indicated above. For a better understanding, Example 1 has been reproduced in this table.

Table II relates to rinsing compositions.

These compositions are applied to the hair and are left in position for a few minutes, after which the hair is rinsed.

It is found that the hair combs out more easily and that it exhibits improved softness and improved springiness.

After drying, the hairstyle is very springy, the hair has body and the waveset lasts very well.

Table III relates to wavesetting lotions.

It is found, after applying these lotions to dyed hair that the dry hair is bulky, springy, free from electrostatic charge and easy to style.

Water in sufficient amount to give 100 cm³ (in the case of Table III) or 100 g (in the case of Table I and II) is added to the various ingredients mentioned in Tables I, II and III.

In general, perfumes and dyestuffs intended to improve the presentation of the said compositions are added to the various compositions mentioned above.

By way of example, about 0.1 g of dyestuff and about 0.2 g of perfume are introduced into compositions 1 to 4, 10 to 15 and 20 to 40.

The meanings of the abbreviations as well as the meaning of the tradenames of the various products used in the examples are indicated in the preceding description, and below.

Numerous polymers used according to the invention are also described in more detail in the "COSMETIC INGREDIENT DICTIONARY" published by "THE COSMETIC TOILETRY AND FRAGRANCE ASSOCIATION INC.".

| SURFACE-ACTIVE AGENTS AND ADJUVANTS | |
|---|---|
| ACSPO | A mixture of cetyl/stearyl alcohol and of cetyl/stearyl alcohol oxyethyleneated with 15 mols of ethylene oxide. |
| AES | The sodium salt of the sulphate half-ester of an alkyl ($C_{12}$–$C_{14}$) ether obtained by oxyethyleneation with 2.2 mols of ethylene oxide. |
| ALE 12 | Lauryl alcohol polyoxyethyleneated with 12 mols of ethylene oxide. |
| AST 12 14 | Triethanolamine alkyl($C_{12}$–$C_{14}$)-sulphate. |
| LANETTE WAX E | Cetyl/stearyl alcohol sulphated to the extent of 10%, sold by Messrs. HENKEL. |
| DEHYTON AB 30 | $C_{12}$–$C_{18}$-alkyl-dimethyl-carboxymethyl-ammonium hydroxide sold by Messrs. HENKEL. |
| EMPICOL STT | Cetyl/stearyl alcohol sulphosuccinate sold by Messrs. MARCHON. |
| IMWITOR 960 K | Self-emulsifiable glycerol stearate sold by Messrs. DYNAMIT NOBEL |
| MIRANOL C2M | 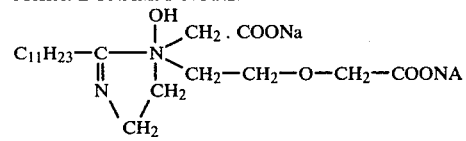 |
| TA-1 | $RCHOH-CH_2O+CH_2-CHOH-CH_2O)_nH$<br>R:$C_9$–$C_{12}$-alkyl, n = 3.5. |
| TA-2 | Non-ionic surface-active agent based on lauryl alcohol polyglycerolated (with 4.2 mols of glycerol), as a solution containing about 60% of active material.<br>Statistical formula:<br>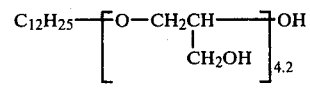 |
| TA-3 | Polyglycerolated fatty diglycolamide.<br>$R-CO-NH-CH_2-CH_2-O-CH_2-CH_2-(-O-CH_2-CHOH-CH_2)_{3.5}-OH$<br>R = amides of natural $C_{12}$–$C_{18}$ fatty acids. |
| DIVALIN SO | Acid phosphoric ester of ethoxylated oleyl alcohol. |
| ACS 15 OE | Cetyl/stearyl alcohol oxyethyleneated with 15 mols of ethylene oxide. |
| LCC | Lactate of copra N,N-diethylamino-polyoxyethyl-carboxylate, containing 4 mols of ethylene oxide. |
| SIMULSOL 1951 D | Cetyl/stearyl alcohol oxyethyleneated with 10 mols of ethylene oxide, sold by SEPPIC MONTANOIR. |
| AKYPO RLM 100 | Weak anionic surface-active agent of the formula $R-(OCH_2R-(OCH_2CH_2)_xOCH_2COOH$, R being a mixture of $C_{12}$–$C_{14}$ alkyl radicals and x being 10, sold by Messrs. CHEMY. |
| SANDOPAN DTC AC | Tridecyl-heptaoxyethylene-carboxylic acid of the formula:<br>$CH_3(CH_2)_{11}-CH_2(OCH_2-CH_2)_6OCH_2-COOH$<br>sold by Messrs. SANDOZ. |
| SANDOPAN DTC | Sodium salt of tridecyl-heptaoxyethylene-carboxylic acid. |
| MAYPON 4 CT | Triethanolamine salt of a condensation product of copra acid with an animal protein hydrolysis product, sold by Messrs. STEPAN. |
| ELFAN OS 46 | Olefine sulphonate<br>$CH_3-(CH_2)_{10-12}-CH=CH-CH_2SO_3Na$ |

-continued

SURFACE-ACTIVE AGENTS AND ADJUVANTS

| | |
|---|---|
| | $+ \text{CH}_3-(\text{CH}_2)_{10-12}\text{CH}_2-\underset{\underset{\text{OH}}{\mid}}{\text{CH}_2\text{SO}_3\text{Na}}$ |
| | sold by Messrs. AKZO CHEMIE GmbH. |
| SETACIN 103 Spezial | The sodium salt of the hemi-sulphosuccinate of a polyoxyethyleneated lauryl alcohol, sold by Messrs. ZSCHIMMER und SCHWARZ CHEMISCHE FABRIKEN. |
| SURFARON A 72 12 N 30 | An aqueous solution of sodium lauroyl sarcosinate of density about 1.035 at 20° C., sold by Messrs. PROTEX. |
| HOSTAPUR SAS-30 | n-Alkanesulphonates obtained by sulphoxidation of $C_{13}$ to $C_{18}$ n-paraffins, of mean molecular weight 328, sold by Messrs. HOECHST. |
| LIPOPROTEOL LK | Triethanolamine salt of lauroyl-keratinic acid, sold by Messrs. RHONE POULENC. |
| REMCOPAL 306 | Octylphenol oxyethyleneated with 5.5 mols of ethylene oxide, sold by Messrs. GERLAND. |
| REMCOPAL 349 | Nonylphenol oxyethyleneated with 9 mols of ethylene oxide, sold by Messrs. GERLAND. |
| MYRJ 53 | Polyoxyethylene stearate, containing 50 mols of ethylene oxide, sold by Messrs. Atlas, or sold under the name PEG-50 stearate by Messrs. ICI U.S.A. |
| SOMEPON 20 | Hydroxyethylamide of a sulphated copra fatty acid, sold by Messrs. MONTANOIR. |
| NORANIUM M 2 C | Dimethyl-dilauryl-ammonium chloride sold by Messrs. CECA PROCHINOR. |
| EMCOL E 607 L | N-lauryl-colamino-formylmethyl-pyridinium chloride sold by Messrs. Witco; also referred to, in the CTFA dictionary, as lapyrium chloride. |
| TWEEN 20 | Polysorbate 20, or the monolaurate of sorbitan polyoxyethyleneated with 20 mols of ethylene oxide, sold by Messrs. Atlas. |
| EMPICOL 0091 | Sodium lauryl-monoethanolamine-sulphosuccinate sold by Messrs. MARCHON. |
| AROMOX DMCD | Coconut alkyl-dimethylamine oxide sold by Messrs. AKZO CHEMIE. |
| PLURONIC L 62 | Polycondensate of ethylene oxide and of polypropylene glycol, of the formula: $\text{HO}(\text{CH}_2-\text{CH}_2-\text{O})_8-(\underset{\underset{\text{CH}_3}{\mid}}{\text{CH}}-\text{CH}_2\text{O})_{30}-(\text{CH}_2-\text{CH}_2\text{O})_8\text{H}$ sold by Messrs. UGINE KUHLMANN. |
| AMPHOTERE 1 | Surface-active agent of the formula: $\underset{\underset{\text{R}-\text{NH}-\text{CH}-\text{COONa}}{\mid}}{\text{CH}_2-\text{CONH}(\text{CH}_2)_3-\text{N}\begin{array}{c}\diagup \text{C}_2\text{H}_5 \\ \diagdown \text{C}_2\text{H}_5\end{array}}$ where R represents a mixture of alkyl groups derived from copra fatty acids. |
| AMPHOTENSID GB 2047 | An alkylimidazoline sold by Messrs. ZSCHIMMER und SCHWARZ. |
| AMPHOSOL DMC/MCA | Acetyl-dimethyl-dodecyl-ammonium chloride sold by Messrs. ICEVE VOREPPE. |
| AROMOX DM 14 DW | The compound of the formula: $\underset{\underset{\text{O}}{\downarrow}}{\text{C}_{14}\text{H}_{29}\text{N}(\text{CH}_3)_2}$ sold by Messrs. AKZO CHEMIE. |
| DERIPHAT 160 | Disodium N-lauryl-$\beta$-iminopropionate sold by Messrs. GENERAL MILLS. |
| STEINAPON AM B.13 | A betaine alkylamide of the formula: $\text{R}-\text{CO}-\text{NH}-(\text{CH}_2)_3-\overset{+}{\text{N}}-(\text{CH}_3)_2-\text{CH}_2-\text{COO}^-$ sold by Messrs. REWO. |

ANIONIC POLYMERS

| | |
|---|---|
| 28.29.30 | A terpolymer of vinyl acetate, crotonic acid/vinyl neo-decanoate sold under the name Resin 28.29.30 by Messrs. NATIONAL STARCH. |
| FLEXAN 500 | A sodium salt of polystyrene-sulphonic acid, of molecular weight about 500,000, sold under the name Flexan 500 by Messrs. NATIONAL STARCH. |
| FLEXAN 130 | A sodium salt of a polystyrene-sulphonic acid |

ANIONIC POLYMERS -continued

| | |
|---|---|
| | of molecular weight of the order of 100,000, sold under the name Flexan 130 by Messrs. NATIONAL STARCH. |
| QUADRAMER 5 | A copolymer of N-tertiary butyl acrylamide, acrylamide, acrylic acid and N-vinylpyrrolidone, sold under the name Quadramer 5 by Messrs. AMERICAN CYANAMID. |
| GANTREZ ES 425 | The monobutyl ester of a methyl vinyl ether/ maleic acid copolymer, sold under the name Gantrez ES 425 by Messrs. GENERAL ANILINE. |
| EMA 1325 | A copolymer of ethylene and monobutyl maleate sold under the name EMA 1325 by Messrs. MONSANTO. |
| P I | A terpolymer of vinyl acetate, crotonic acid and allyl dimethylpropanoate (77/8/15). |
| P 2 | A copolymer of vinyl acetate, crotonic acid, allyl dimethylpropanoate and vinyl laurate (77/8/14/1). |
| P 3 | A copolymer of vinyl acetate, allyl stearate and allyloxyacetic acid (80.5/15/4.5). |
| RESIN TV 242 or ARISTOFLEX A | A terpolymer of vinyl acetate, crotonic acid and polyethylene glycol, sold by Messrs. HOECHST. |
| VERSICOL K 11 | A polymer of methacrylic acid, of molecular weight 10,000 and viscosity 1,000 cps, in the form of a 25% strength solution, sold by Messrs. ALLIED COLLOIDS. |
| VERSICOL E 5 | A mixture of a homopolymer and a copolymer of acrylic acid, of molecular weight about 3,500, in the form of a 25% strength solution of viscosity 16 cps, sold by Messrs. ALLIED COLLOIDS. |
| CARBOPOL 940 CARBOPOL 941 | A carboxyvinyl polymer, of high molecualr weight, derived from acrylic acid, and sold by GOODRICH CHEMICALS. |
| PA-4 | A copolymer of allyl acetate and maleic anhydride, monoesterified with ethanol (50/50). |
| PA-5 | A copolymer of isobutyl vinyl ether and maleic anhydride monoesterified with ethanol (50/50). |
| PA-6 | A copolymer of butyl vinyl ether and maleic anhydride monoesterified with ethanol (50/50). |
| PA-7 | A copolymer of allyl acetate and maleic anhydride amidified with dodecylamine and dibutylamine (50/50). |
| PA-8 | A terpolymer of allyl acetate, 2 ethyl hexyl acrylate and maleic anhydride, monoesterified with ethanol (47.4/2.6/50). |
| PA-9 | A copolymer of isobutyl vinyl ether, allyl neoheptanoate and maleic anhydride monoesterified with ethanol (18.2/31.8/50). |
| LIGNOSULPHONATE C 10 | Calcium lignosulphonate, of apparent density 0.48, having a pH, in 5% strength solution, of about 5.8. |
| LIGNOSULPHONATE C 14 | Calcium lignosulphonate, of apparent density 0.48, having a pH, in 5% strength solution, of about 8, both sold by Messrs. L'AVEBENE. |
| HYDAGEN F | The sodium salt of a polyhydroxycarboxylic acid, sold by Messrs. HENKEL. |
| RETEN 423 | An acrylic polyelectrolyte of high molecular weight, having a Brookfield LVF viscosity, at 60 rpm, of 3,000-4,000 cps, sold by Messrs. HERCULES. |
| ULTRAHOLD 8 | An acrylic copolymer of flash point 104° F. (TAG open cup) offered by Messrs. CIBA GEIGY. |
| CYANAMER A 370 | A modified polyacrylamide having a molecular weight of about 200,000 and a specific viscosity of 3.7 ± 0.5, sold by MESSRS. AMERICAN CYANAMID. |
| P-COL | A colored polymer, consisting of the product sold under the name GANTREZ ES 425, of which some of the carboxyl groups have been amidified by the primary amine group of the dyestuff: 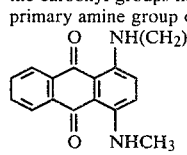 |
| RESIN 26.13.14 | Vinyl acetate - crotonic acid copolymer of viscosity 800 cps at 22° C. as a 40% solution and acidity 1.16 meq/g. of dry resin. |
| PA-10 | Copolymer allyl pivalate/maleic anhydride monoesterified with ethanol 50/50. |
| RETEN 421 | Acrylic polyelectrolyte having a high molecular weight, |

ANIONIC POLYMERS a Brookfield viscosity LVF 60 cpm of 1000–1500 cps sold by Messrs. HERCULES.

CATIONIC POLYMERS

| | |
|---|---|
| MERQUAT 100 | A homopolymer of dimethyl-diallyl-ammonium chloride, of molecular weight <100,000, sold under the name Merquat 100 by Messrs. MERCK. |
| MERQUAT 550 | A copolymer of dimethyl-diallyl-ammonium chloride and acrylamide, of molecular weight >500,000, sold under the name Merquat 550 by Messrs. MERCK. |
| CARTARETINE F 4 | A copolymer of adipic acid and dimethylamino-hydroxypropyl-diethylenetriamine, sold under the name Cartaretine F 4 by Messrs. SANDOZ. |
| GAFQUAT 755 | A quaternary copolymer of vinylpyrrolidone having a molecular weight of 1,000,000, marketed by Messrs. GENERAL ANILINE. |
| GAFQUAT 734 | A quaternary copolymer of vinylpyrrolidone having a molecular weight of 100,000, marketed by Messrs. GENERAL ANILINE. |
| AZA-1 | A cationic polycondensate of piperazine, diglycolamine and epichlorohydrin in the molar ratios of 4/1/5, described in Example 2 of French Patent 2,280,361. |
| AZA-2 | A cationic polycondensate of piperazine, diglycolamine and epichlorohydrin in the molar ratios of 1/1/2, described in Example 3 of French Patent 2,280,361. |
| AZA-3 | A cationic polycondensate of piperazine, diglycolamine and epichlorohydrin in the molar ratios of 2/1/3, described in Example 4 of French Patent 2,280,361. |
| AZA-4 | A cationic polycondensate of piperazine, diglycolamine and epichlorohydrin in the molar ratios of 4/1/5, described in Example 5 of French Patent 2,280,361. |
| AZA-5 | A cationic polycondensate of piperazine, 2-amino-2-methyl-1,3-propanediol and epichlorohydrin in the molar ratios of 1.07/0.45/1.5, described in Example 6 of French Patent 2,280,361. |
| AZA-6 | A cationic polycondensate of piperazine and epichlorohydrin in the molar ratio of 1/1, described in Example 1 of French Patent 2,162,025. |
| AZA-7 | A cationic polycondensate of piperazine and piperazine bis-acrylamide in the molar ratio of 1/1, described in Example 14 of French Patent 2,162,025. |
| PGR-1 | A grafted and crosslinked copolymer of N-vinyl-pyrrolidone/dimethylaminoethyl methacrylate/polyethylene glycol/tetraallyloxyethane, in the ratios of 62/28/10/0.02, quaternised with dimethyl sulphate; described in Example 2 of French Patent 2,189,434. Polymers PGR-2 to PGR-16 are the polymers described respectively in Examples 1 and 3 to 17 of French Patent 2,189,434. |
| G-14 | A polymer of unit structure: |

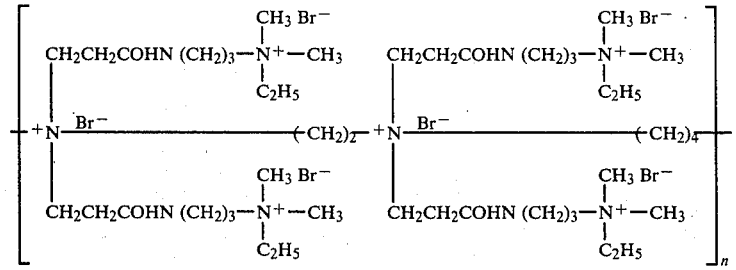

TABLE I

| Example No. | POLYMER ANIONIC | % g | CATIONIC | SHAMPOOS SURFACE-ACTIVE AGENT | % g | SOLVENTS and/or ADJUVANTS | % g | pH | Acidifying or alkalizing agent |
|---|---|---|---|---|---|---|---|---|---|
| 1 | FLEXAN 500 | 0.4 | K III a | 0.6 AST 1214 | 10 | copra diethanolamide | 3 | 7.5 | lactic acid |
| 2 | FLEXAN 130 | 0.5 | K IV b | 0.4 ammonium lauryl- | 9 | lauric acid diethanolamide | 3 | 4.5 | lactic acid |

TABLE I-continued

| Example No. | POLYMER ANIONIC | % g | POLYMER CATIONIC | % g | SHAMPOOS SURFACE-ACTIVE AGENT | % g | SOLVENTS and/or ADJUVANTS | % g | pH | Acidifying or alkalizing agent |
|---|---|---|---|---|---|---|---|---|---|---|
| | | | | | sulphate | | hydroxypropyl-methylcellulose | 0.2 | | |
| 3 | P 2 | 0.4 | KA V b | 0.6 | TA-1 | 8 | lauric acid diethanolamide | 3 | 7.8 | triethanol-amine |
| 4 | FLEXAN 500 | 0.4 | KA V b | 0.6 | AST 1214 | 8 | lauric acid diethanolamide | 3 | | |
| | | | | | | | DIVALIN SO | 0.5 | 7.2 | |
| | | | | | | | hydroxypropyl-methylcellulose | 0.2 | | |
| 5 | 28.29.30 | 0.6 | KA VI b | 0.6 | AST 1214 | 10 | | | 7.5 | |
| | | | | | TA-1 | 5 | | | | |
| 6 | 28.29.30 | 1.5 | K I b | 0.6 | AST 1214 | 15 | copra diethanolamide | 3 | 7.5 | lactic acid |
| | | | | | | | hydroxypropyl-methylcellulose | 0.2 | | lactic acid |
| 7 | 28.29.30 | 0.4 | K I | 1.5 | AST 1214 | 15 | copra diethanolamide | 3 | 7.5 | lactic acid |
| 8 | 28.29.30 | 0.6 | CARTARETINE F4 | 0.7 | AST 1214 | 12.5 | lauric acid diethanolamide | 2 | 7.6 | |
| | | | | | TA-1 | 5 | | | | |
| 9 | FLEXAN 500 | 0.6 | CARTARETINE F4 | 0.4 | AST 1214 | 25 | hydroxypropyl-methylcellulose | 0.2 | 5 | |
| 10 | FLEXAN 500 | 0.6 | CARTARETINE F4 | 0.4 | AES | 25 | | | 7.2 | |
| 11 | FLEXAN 500 | 0.5 | G4 | 0.4 | AST 1214 | 25 | lauric acid diethanolamide | 2 | 6.8 | |
| 12 | QUADRAMER 5 | 0.4 | CARTARETINE F4 | 0.6 | AST 1214 | 10 | hydroxypropyl-methylcellulose | 0.2 | 7.5 | |
| 13 | FLEXAN 130 | 0.4 | G2 | 0.4 | AST 1214 | 15 | lauric acid diethanolamide | 3 | 7.6 | |
| 14 | GANTREZ ES 425 | 0.2 | KA I b | 0.5 | AST 1214 | 15 | lauric acid diethanolamide | 2 | 7.2 | lactic acid |
| | | | | | | | hydroxypropyl-methylcellulose | 0.2 | | |
| 15 | QUADRAMER 5 | 0.3 | CARTARETINE F4 | 0.6 | TA-I | 8 | hydroxypropyl-methylcellulose | 0.2 | 7.5 | triethanol-amine |
| | 28.29.30 | 0.2 | | | AST 1214 | 5 | | | | |
| 16 | P I | 0.3 | CARTARETINE F4 | 0.6 | AST 1214 | 15 | | | 7.35 | lactic acid |
| 17 | EMA 1325 | 0.3 | KA VII b | 0.5 | AST 1214 | 15 | copra diethanolamide | 2 | 6.2 | lactic acid |
| 18 | 28.29.30 | 0.2 | TYDEX 16 | 0.5 | TA-1 | 10 | | | 8.2 | |
| 19 | 28.29.30 | 0.2 | PD 170 | 0.8 | AST 1214 | 12 | lauric acid diethanolamide | 3 | 7.7 | |
| | | | | | TA-I | 8 | | | | |
| 20 | VERSICOL K 11 | 0.4 | KA V b | 0.6 | AST 1214 | 25 | lauric acid diethanolamide | 3 | 8.2 | triethanol-amine |
| 21 | FLEXAN 500 | 0.4 | K V a | 0.6 | AST 1214 | 15 | lauric acid diethanolamide | | 7.5 | triethanol-amine |
| 22 | 28.29.30 | 0.8 | K I c | 0.6 | AES | 6 | lauric acid diethanolamide | 3 | 8.9 | triethanol-amine |
| | | | | | Dehyton AB 30 | 8 | | | | |
| 23 | FLEXAN 130 | 0.5 | K IV b | 0.4 | ammonium lauryl-sulphate | 9 | lauric acid diethanolamide | 3 | | |
| | | | | | | | hydroxypropyl-methylcellulose | 0.2 | 7.4 | lactic acid |
| 24 | 28.29.30 | 0.4 | K VI a | 0.5 | AES | 8 | lauric acid diethanolamide | 3 | 7.5 | lactic acid |
| 25 | FLEXAN 500 | 0.6 | CARTARETINE F4 | 0.4 | AST 1214 | 25 | hydroxypropyl-methylcellulose | 0.2 | 8 | |
| 26 | RESIN TV 242 | 0.3 | K Ia | 0.8 | TA-1 | 8 | lauric acid diethanolamide | 3 | 7.5 | triethanol-amine |
| | | | | | AST 1214 | 8 | | | | |
| 27 | 28.29.30 | 0.6 | K I e | 0.9 | AST 1214 | 10 | lauric acid deithanolamide | 3 | | |
| | | | | | | | hydroxypropyl-methylcellulose | 0.2 | 7.5 | |
| 28 | FLEXAN 500 | 0.4 | GAFQUAT 755 | 0.6 | TA-1 | 10 | | | 7.6 | |
| 29 | 28.29.30 | 0.4 | JR 400 | 0.6 | TA-1 | 10 | copra diethanolamide | 3 | 6.8 | lactic acid |
| 30 | 28.29.30 | 0.6 | KA IX b | 0.4 | TA-1 | 6 | | | 7.6 | |
| | | | | | AST 1214 | 3.5 | | | | |
| 31 | 28.29.30 | 1 | CARTARETINE F4 | 0.6 | TA-1 | 6 | | | 7.7 | |
| | | | | | AST 1214 | 4 | | | | |
| 32 | 28.29.30 | 0.6 | CARTARETINE F4 | 0.4 | TA-1 | 6 | | | | |
| | | | | | AES | 4 | | | 8.5 | |

TABLE I-continued

SHAMPOOS

| Example No. | POLYMER ANIONIC | % g | CATIONIC | % g | SURFACE-ACTIVE AGENT | % g | SOLVENTS and/or ADJUVANTS | % g | pH | Acidifying or alkalizing agent |
|---|---|---|---|---|---|---|---|---|---|---|
| 33 | 28.29.30 | 0.6 | KA X b | 0.4 | TA-1 | 6 | | | | |
| | | | | | AST 1214 | 3.5 | | | 7.8 | |
| 34 | 28.29.30 | 0.6 | KA IX b | 0.5 | AST 1214 | 12 | copra diethaolamide | 3 | 7.9 | lactic acid |
| 35 | FLEXAN 130 | 0.4 | KA X b | 0.6 | AES | 12 | copra diethanolamide | 3 | 9.3 | |
| 36 | FLEXAN 130 | 0.4 | KA X b | 0.6 | AST 1214 | 12 | copra diethanolamide | 3 | 7 | lactic acid |
| 37 | 28.29.30 | 0.4 | PD 170 | 0.1 | ALE 12 | 7 | lauric acid diethanolamide | 3 | 7.2 | lactic acid |
| | | | | | MIRANOL C2M | 10 | | | | |
| 38 | 28.29.30 | 0.2 | PD 170 | 0.2 | AST 1214 | 12 | | | | |
| | | | CARTARETINE F4 | 0.3 | TA-1 | 8 | | | 8.8 | |
| 39 | 28.29.30 | 0.4 | MERQUAT 550 | 0.6 | AST 1214 | 12 | copra diethanolamide | 3 | 7.5 | lactic acid |
| | | | | | TA-1 | 8 | | | | |
| 40 | 28.29.30 | 0.2 | K I a | 0.6 | AST 1214 | 25 | copra diethanolamide | 3 | 7.3 | lactic acid |
| | | | K VIII | 0.4 | | | | | | |
| 41 | 28.29.30 | 0.3 | K I a | 0.8 | TA-1 | 10 | | | 5 | |
| 42 | 28.29.30 | 0.3 | CARTARETINE F4 | 0.5 | TA-1 | 10 | | | 6 | |
| 43 | 28.29.30 | 0.4 | G 3 | 0.6 | AST 1214 | 10 | copra diethanolamide | 2 | 7 | triethanolamine |

TABLE II

RINSING TREATMENT

| Example No. | POLYMER ANIONIC | % g | CATIONIC | % g | SURFACE-ACTIVE AGENT | % g | SOLVENTS and/or ADJUVANTS | % g | pH | Acidifying or alkalizing agent |
|---|---|---|---|---|---|---|---|---|---|---|
| 44 | 28.29.30 | 0.6 | K I a | 0.6 | ACSPO | 5 | | | 7.5 | |
| 45 | FLEXAN 500 | 0.03 | G 4 | 0.5 | TA-1 | 0.5 | | | 9.1 | |
| 46 | 28.29.30 | 0.5 | CARTARETINE F4 | 0.7 | ACS 15 0E | 5.6 | vaseline oil | 2.5 | 5.5 | |
| 47 | QUADRAMER 5 | 0.05 | KA VI b | 0.3 | SIMULSOL 1951 RD | 2.5 | stearyl alcohol | 1.8 | 8.9 | |
| | | | | | | | vaseline oil | 15 | | |
| | | | | | | | cetyl/stearyl alcohol | 2.5 | | |
| 48 | FLEXAN 500 | 0.5 | K I a | 0.8 | EMPICOL STT | 5 | | | 9.5 | triethanolamine |
| 49 | FLEXAN 500 | 0.02 | CARTARETINE F4 | 1 | ACS 15 OE | 5.6 | vaseline oil | 2.5 | 4.8 | |
| | | | | | | | stearyl alcohol | 1.8 | | |
| 50 | 28.29.30 | 0.05 | KA IV b | 0.7 | SIMULSOL 1951 RD | 2.5 | vaseline oil | 15 | 9.1 | |
| | | | | | | | cetyl/stearyl alcohol | 2.5 | | |
| 51 | FLEXAN 500 | 0.3 | K I a | 0.6 | ACSPO | 5 | | | 10 | |
| 52 | 28.29.30 | 0.6 | K I a | 0.6 | ACSPO | 5 | | | 8.7 | |
| | | | GAFQUAT 755 | 0.6 | | | | | | |
| 53 | 28.29.30 | 0.3 | GAFQUAT 755 | 0.5 | | | IMWITOR 960K | 5 | 8.5 | |

TABLE III

WAVESETTING LOTIONS

| Example No. | POLYMER ANIONIC | % g | CATIONIC | % g | SURFACE-ACTIVE AGENT | % g | SOLVENTS and/or ADJUVANTS | alcohol strength | pH | Acidifying or alkalizing agent |
|---|---|---|---|---|---|---|---|---|---|---|
| 54 | 28.29.30 | 0.5 | CARTARETINE F4 | 0.5 | TA-I | 0.5 | ethyl alcohol q.s.p. | 50° | 9.5 | 2-amino-2-methyl-1-propanol |
| 55 | 28.29.30 | 0.5 | CARTARETINE F4 | 0.5 | | | ethyl alcohol q.s.p. | 50° | 9.5 | 2-amino-2-methyl-1-propanol |
| 56 | P 3 | 0.25 | CARTARETINE F4 | 0.5 | | | ethyl alcohol q.s.p. | 50° | 9.5 | 2-amino-2-methyl-1-propanol |
| 57 | Resin TV 242 | 0.5 | CARTARETINE F8 | 0.5 | | | ethyl alcohol q.s.p. | 50° | 8.6 | 2-amino-2-methyl-1-propanol |
| 58 | 28.29.30 | 0.5 | K I a | 0.5 | | | ethyl alcohol | 50° | 7.5 | 2-amino-2-methyl-1- |

TABLE III-continued

| | | WAVESETTING LOTIONS | | | | |
|---|---|---|---|---|---|---|
| Example No. | POLYMER ANIONIC % g CATIONIC % g | SURFACE- ACTIVE AGENT % g | SOLVENTS and/or ADJUVANTS | alcohol strength | pH | Acidifying or alkalizing agent |
| | | | q.s.p. | | | propanol |

EXAMPLE 59

The following dyeing composition is prepared:

| | |
|---|---|
| 1-γ-aminopropylamino-4-methylamino-anthraquinone hydrochloride | 0.3 g |
| polymer of formula K I a | 2.5 g |
| Flexan 500 | 2.5 g |
| butylglycol | 10 g |
| tartaric acid q.s.p. | pH 9 |
| water q.s.p. | 100 g |

40 g of the gel thus obtained are applied for 15 minutes to hair dyed light chestnut.

After rinsing, shampooing and drying, the head of hair exhibits an attractive ashen sheen.

EXAMPLE 60

The following dyeing composition is prepared:

| | |
|---|---|
| 1-methoxy-2-β-hydroxyethylamino-5-nitro-benzene | 0.2 g |
| nitro-paraphenylenediamine | 0.08 g |
| Cartaretine F4 | 2.5 g |
| Flexan 500 | 2.5 g |
| butylglycol | 8 g |
| monoethanolamine q.s.p. | pH 9.5 |
| water q.s.p. | 100 g |

40 g of the gel thus obtained are readily applied to a naturally dark blond head of hair.

After 15 minutes, the hair is rinsed; after shampooing and drying, the hair is uniformly colored Venetian blond.

EXAMPLE 61

The following dyeing composition is prepared:

| | |
|---|---|
| coloring polymer of formula KC-2 | 1.7 g |
| polymer of formula KA VIII b | 5 g |
| Flexan 500 | 5 g |
| sodium carbonate q.s.p. | pH 10 |
| water, q.s.p. | 100 g |

40 g of the gel thus produced are applied for 15 minutes to moderately bleached hair.

After rinsing and drying, the head of hair combs out very easily and exhibits an aesthetically particularly attractive rosewood sheen.

EXAMPLE 62

The following dyeing composition is prepared:

| | |
|---|---|
| coloring polymer of formula KC-1 | 0.97 g |
| Gafquat 755 | 0.5 g |
| Flexan 500 | 0.5 g |
| tartaric acid, q.s.p. | pH 7 |
| water, q.s.p. | 100 g |

A very attractive gel is obtained, of which 40 g are applied to a head of hair which was initially dyed blond.

After 15 minutes, the head of hair is rinsed; it combs out very easily and is colored pearlescent blond.

EXAMPLE 63

The following dyeing composition is prepared:

| | |
|---|---|
| 1-amino-4-(2-methoxyethyl)-amino-benzene dihydrochloride | 1.6 g |
| para-aminophenol | 0.3 g |
| resorcinol | 0.2 g |
| meta-aminophenol | 0.25 g |
| 1-(2-hydroxy-ethoxy)-2,4-diamino-benzene dihydrochloride | 0.02 g |
| 1-methoxy-3-nitro-4-β-hydroxyethylamino-benzene | 0.1 g |
| 1-β-hydroxyethoxy-3-nitro-4-amino-benzene | 0.5 g |
| Flexan 500 | 5 g |
| butylglycol | 9 g |
| ammonium thiolactate containing 50% of thio-lactic acid | 0.8 g |
| hydroquinone | 0.1 g |
| 1-phenyl-3-methyl-5-pyrazolone | 0.1 g |
| sodium salt of diethylenetriamine-pentaacetic acid | 2.4 g |
| ammonia of 22° Be strength | 10 cc |
| water, q.s.p. | 100 g |

Before use, 20 g of this limpid liquid are thoroughly mixed with the same amount of the following colorless solution:

| | |
|---|---|
| Gafquat 755 | 5 g |
| hydrogen peroxide of 200 volumes strength | 10 cc |
| orthophosphoric acid q.s.p. | pH 4 |
| water, q.s.p. | 100 g |

An attractive transluscent gel is obtained, which is applied to an initially blond head of hair.

The coloration appears gradually and uniformly and after 30 minutes the hair is rinsed and shampooed.

After drying, the hair combs out easily and is coloured a very natural light chestnut.

EXAMPLE 64

The dyeing cream composition of the following formula is prepared:

| | |
|---|---|
| Cartaretine F4 | 2 g |
| Flexan 500 | 1.6 g |
| cetyl alcohol | 15 g |
| sodium salt of cetyl/stearyl alcohol-sulphate | 4 g |
| cetyl/stearyl alcohol oxyethyleneated with 15 mols of ethylene oxide | 3 g |
| lauryl alcohol | 5 g |
| ammonia of 22° Be strength | 10 cc |
| p-toluylene-diamine | 0.28 g |
| p-aminophenol | 0.090 g |
| m-diaminoanisole sulphate | 0.05 g |
| resorcinol | 0.250 g |
| m-aminophenol | 0.070 g |
| ethylenediamine-tetraacetic acid | 1 g |
| sodium bisulphite, d = 1.32 | 1.2 g |
| water, q.s.p. | 100 g |

This composition is used as a coloring cream.

20 g of this cream are mixed with 30 g of hydrogen peroxide of 20 volumes strength. A cream is obtained, which is applied to chestnut hair.

After leaving the cream on the hair for 30 to 45 minutes, the hair is rinsed and dried.

An ashen light chestnut shade is obtained. The hair is springy and easy to style, and the waveset holds well.

EXAMPLE 65

The following composition is prepared:

| | | |
|---|---|---|
| Gafquat 755 | 0.02 | g |
| carboxyvinyl polymer sold under the name CARBOPOL 941 by Messrs. GOODRICH CHEMICALS | 0.03 | g |
| ethyl alcohol, q.s.p. | 65° | |
| perfume | 1.5 | g |
| water, q.s.p. | 100 | cc |

This composition can be used as a softening toilet water.

When applied to the skin, this lotion softens, and pleasantly perfumes, the skin.

EXAMPLE 66

The following composition is prepared:

| | | |
|---|---|---|
| Gafquat 755 | 0.04 | g |
| carboxyvinyl polymer sold under the name CARBOPOL 940 by Messrs. GOODRICH CHEMICALS | 0.04 | g |
| ethyl alcohol, q.s.p. | 55° | |
| perfume | 0.8 | g |
| ethylene oxide polymer sold under the name POLYETHYLENE GLYCOL 400 by Messrs. HOECHST HO—(CH$_2$—CH$_2$—O)$_n$—H n = 9 | 1 | g |
| allantoin | 0.1 | g |
| water, q.s.p. | 100 | cc |

This composition is used as an after-shave lotion, This composition soothes the skin after shaving and leaves it soft and perfumed.

EXAMPLE 67

The following composition is prepared:

| | | |
|---|---|---|
| Gafquat 755 | 0.1 | g |
| polymer 28.29.30 | 0.1 | g |
| ethyl alcohol, q.s.p. | 60° | |
| perfume | 0.05 | g |
| water, q.s.p. | 100 | cc |

This composition is used as an after-shave lotion.

When applied to the skin after shaving, this lotion softens the skin.

EXAMPLE 68

The following composition is prepared:

| | | |
|---|---|---|
| Gafquat 755 | 0.5 | g |
| polymer 28.29.30 | 0.5 | g |
| sodium salt of cetyl/stearyl alcohol-sulphate | 2.6 | g |
| cetyl alcohol | 7.5 | g |
| cetyl/stearyl alcohol oxyethyleneated with 15 mols of ethylene oxide | 1.5 | g |
| lauryl alcohol | 2.5 | g |
| water, q.s.p. | 100 | g |

This composition is used as a hair treatment cream.

30 to 50 g of this cream are applied to clean, moist and towel-dried hair, taking care to impregnate the head of hair thoroughly.

The composition is left on the hair for 15 minutes and the hair is then rinsed. The wet hair combs out easily and is soft to the touch.

The hair is set in waves and dried under a hood.

The dry hair is silky to the touch. It is glossy and easy to style, and the waveset holds well.

EXAMPLE 69

The following composition is prepared:

| | | |
|---|---|---|
| Cartaretine F4 | 1.8 | g |
| Flexan 500 | 1.2 | g |
| lauryl alcohol | 2 | g |
| stearyl alcohol oxyethyleneated with 2 mols of ethylene oxide, sold under the name BRIJ 72 by Messrs. ATLAS | 15 | g |
| water, q.s.p. | 100 | g |
| pH 9 | | |

This composition is used as a hair treatment cream.

20 to 40 g of this cream are applied to dirty and moist hair. After impregnating the head of hair, the composition is left on the hair for 15 to 30 minutes and the hair is then shampooed.

After wavesetting and drying, the hair is springy and easy to style. The waveset holds better.

EXAMPLE 70

A shampoo having the following composition is prepared:

| | | |
|---|---|---|
| anionic polymer referred to as 28.29.30 | 0.4 | g |
| cationic polymer referred to as K 1 | 0.5 | g |
| non-ionic surface-active agent coded TA-1 | 10 | g |
| The pH is adjusted to 8 with lactic acid water, q.s.p. | 100 | g |

This composition is applied to wet and dirty hair, which is thoroughly impregnated therewith. After leaving the composition on the hair for a few minutes, the hair is rinsed.

It is found that the wet hair combs out easily and has volume.

The dry hair is springy, has body, is free from electrostatic charge and is glossy.

If the hair is waveset, the set holds well.

On replacing the cationic polymer defined above by the the polymer 28-29-30 being present in an amount of 0,2 g cationic polymer referred to as ONAMER M,/and the non-ionic surface-active agent by 25 g of a slightly anionic surface-active agent sold under the name AKYPO RLM 100, the pH being adjusted to 7.25 with hydrochloric acid, results similar to those indicated above are obtained.

The same is true if, in the composition defined in this example, the various polymers and other ingredients are replaced by those mentioned to Table III below.

It is found, in particular, that the dry hair is free from static electricity and that it holds well.

It is preferably possible to foresee a second application of the shampoo according to the invention. After rinsing, the hair combs out easily and the dried hair has body and the set holds well.

TABLE IV
SHAMPOOS

| Example No. | POLYMER ANIONIC | % | CATIONIC | % | SURFACE-ACTIVE AGENT | % | SOLVENTS and/or ADJUVANTS | % | pH | Acidifying or alkalizing agent |
|---|---|---|---|---|---|---|---|---|---|---|
| 71 | GANTREZ ES 425 | 0.4 | Cartaretine | 0.8 | TA-1 | 15 | | | 8.5 | NaOH |
| 72 | GANTREZ ES 425 | 0.5 | G 4 | 0.3 | AST 12-14 | 20 | lauric acid diethanolamide | 2 | 5 | HCl |
| 73 | GANTREZ ES 425 | 1 | KA Xb | 0.25 | AKYPO RLM 100 | 10 | | | 9.6 | NaOH |
| 74 | GANTREZ ES 425 | 0.5 | AZA-1 | 0.5 | TA-1 | 10 | | | 8 | HCl |
| 75 | GANTREZ ES 425 | 0.5 | PGR-1 | 0.75 | TA-1 | 15 | | | 7 | HCl |
| 76 | GANTREZ ES 425 | 0.5 | Merquat 550 KA Xb | 0.2 1 | monoethanol-amine lauryl ether-sulphate | 12 | | | 7.5 | HCl |
| 77 | GANTREZ ES 425 | 0.4 | KA Xb | 0.60 | Setacin 103 Spezial | 10 | | | 9 | NaOH |
| 78 | GANTREZ ES 425 | 0.6 | KA Xb | 0.6 | Sandopan DTC | 10 | | | 8.6 | NaOH |
| 79 | GANTREZ ES 425 | 0.4 | KA Xb | 0.9 | TA-2 | 15 | | | 9.8 | NaOH |
| 80 | 28.29.30 | 0.7 | KA Xb | 0.6 | TA-1 Miranol C2 M | 10 5 | | | 8.7 | NaOH |
| 81 | 28.29.30 | 0.8 | KA Xb | 0.6 | TA-1 | 10 | | | 8 | NaOH |
| 82 | GANTREZ ES 425 | 0.6 | KA Xb | 0.6 | TA-1 TA-3 | 7.5 2.5 | | | 8.8 | NaOH |
| 83 | VERSICOL E. 5 | 0.1 | KA Xb | 0.6 | Maypon 4 CT | 15 | | | 8 | NaOH |
| 84 | 28.29.30 | 0.4 | K Ia | 0.7 | Surfaron A 7212 N 30 | 10 | lauric acid diethanolamide | 2 | 8.1 | HCl |
| 85 | FLEXAN 130 | 0.8 | Cartaretine F4 | 0.6 | Elfan 05 46 | 15 | | | 6.5 | HCl |
| 86 | ARISTOFLEX A | 0.5 | KA Xb | 0.8 | Hostapur SAS 30 | 10 | | | 7.5 | HCl |
| 87 | Gantrez ES 425 | 0.5 | K Va | 0.75 | TA-1 | 12 | | | 8 | NaOH |
| 88 | Versicol E 5 | 0.25 | Cartaretine F4 | 0.75 | TA-1 | 15 | | | 3 | HCl |
| 89 | Gantrez ES 425 | 0.6 | KA Xb | 0.9 | TA-1 | 12 | Divalin SO | 0.1 | 8.6 | NaOH |
| 90 | Gantrez ES 425 | 0.4 | KA Xb | 0.6 | AST 12-14 | 10 | lauric acid diethanolamide | 0.2 | 7.5 | HCl |
| 91 | Flexan 130 | 0.4 | Hercosett 57 | 0.6 | AST 1214 | 10 | | | 7 | HCl |
| 92 | Ultrahold 8 | 0.6 | JR 125 | 0.25 | AST 1214 | 25 | | | 7.6 | NaOH |
| 93 | Resin TV 242 | 0.6 | JR 125 | 0.25 | Akypo RLM 100 | 8 | | | 8.3 | HCl |
| 94 | Versicol E. 5 | 0.6 | JR 125 | 0.2 | TA-2 | 10 | | | 4 | lactic acid |
| 95 | 28.29.30 | 0.6 | JR 125 | 0.25 | trimethyl-cetyl-ammonium bromide | 6 | | | 5.7 | |
| 96 | Cyanamer A.370 | 0.6 | JR 400 | 0.25 | Setacin 103 | 10 | | | 8.7 | NaOH |
| 97 | Gantrez ES 425 | 0.6 | JR 400 | 0.2 | trimethyl-cetyl-ammonium bromide TA-1 | 5 5 | | | 3.2 | lactic acid |
| 98 | Ultrahold 8 | 0.5 | JR 30 M | 0.4 | Akypo RLM 100 | 10 | | | 7 | |
| 99 | Versicol E.5 | 0.5 | JR 30 M | 0.5 | LCC | 10 | | | 6 | |
| 100 | 28.29.30 | 0.5 | Gafquat 734 | 1 | Empicol 0091 | 10 | | | 8.9 | |
| 101 | Versicol E.5 | 0.4 | Gafquat 734 | 0.5 | Sandopan DTC AC | 10 | | | 8.6 | NaOH |
| 102 | P. 3 | 0.5 | Gafquat 734 | 0.75 | TA-3 | 15 | | | 8.6 | NaOH |
| 103 | EMA 1325 | 0.5 | AZA-I | 0.6 | Maypon 4 CT | 12 | | | 7.5 | NaOH |
| 104 | Gantrez ES 225 | 0.4 | AZA-2 | 1 | Sandopan DTCAC | 12 | | | 7.2 | NaOH |
| 105 | Hydagen F | 0.3 | AZA-3 | 0.8 | Setacin 103 Spezial | 12 | | | 8.3 | |
| 106 | Resin TV 242 | 0.5 | AZA-3 | 0.5 | TA-1 Aromox DMCD | 5 5 | | | 8 | HCl |
| 107 | Reten 423 | 0.2 | AZA-4 | 0.5 | LCC | 15 | | | 8.9 | |
| 108 | Flexan 130 | 0.5 | AZA-5 | 0.5 | Tween 20 TA-2 | 5 | | | 9.5 | HCl |
| 109 | 28.29.30 | 0.4 | ONAMER M | 0.2 | Setacin 103 Spezial | 25 | | | 5.5 | HCl |
| 110 | PA-4 | 0.3 | K. I | 0.5 | Surfaron A 7212 N 30 | 12 | | | 7.5 | HCl |
| 111 | Gantrez ES 425 | 0.4 | K. I | 0.6 | Lipoproteol LK | 10 | | | 7 | HCl |
| 112 | Cyanamer A 370 | 0.4 | K. I | 0.6 | LCC TA-1 | 4 5 | | | 9.2 | NaOH |
| 113 | Gantrez ES 425 | 0.4 | Merquat 550 | 0.3 | TA-1 | 10 | | | 7 | HCl |
| 114 | Flexan 130 | 0.4 | K. IV | 0.6 | Elfan OS 46 | 8 | | | 7.8 | HCl |
| 115 | EMA 1325 | 0.4 | K. IV | 0.6 | Tween 20 | 10 | | | 9 | NaOH |
| 116 | PA-5 | 0.3 | K. IV | 0.7 | LCC | 8 | | | 4.5 | NaOH |
| 117 | Reten 423 | 0.2 | K. Ia | 0.6 | Elfan OS 46 | 10 | | | 7 | HCl |
| 118 | 28.29.30 | 0.4 | G - 4 | 0.6 | Akypo RLM 100 | 8 | | | 8.1 | HCl |
| 119 | Hydagen F | 0.3 | K. IIIb | 0.6 | Akypo RLM 100 | 12 | | | 3.2 | HCl |
| 120 | PA-6 | 0.2 | K. IIIb | 0.5 | Remcopal 349 | 10 | | | 9 | HCl |
| 121 | PA-7 | 0.35 | K. IIIb | 0.5 | Noranium M 2C | 10 | | | 5 | NaOH |
| 122 | Gantrez ES 425 | 1 | G-4 | 0.2 | TA-I | 10 | | | 7.5 | NaOH |
| 123 | Cyanamer A 370 | 0.3 | K. IVa | 0.5 | Sandopan DTCAC | 10 | | | 7 | NaOH |
| 124 | 28.29.30 | 0.2 | Cartaretine F4 | 0.6 | Amphotensid | 8 | | | 8 | NaOH |

TABLE IV-continued
SHAMPOOS

| Example No. | POLYMER ANIONIC | % | CATIONIC | % | SURFACE-ACTIVE AGENT | % | SOLVENTS and/or ADJUVANTS | % | pH | Acidifying or alkalizing agent |
|---|---|---|---|---|---|---|---|---|---|---|
| 125 | Versicol E.5 | 0.35 | K. Va | 0.7 | G-B 2047 Akypo RLM 100 | 14 | | | 8 | NaOH |
| 126 | PA-8 | 0.4 | K.A. IIb | 0.6 | Somepon ML 20 | 8 | | | 8.5 | HCl |
| 127 | PA-8 | 0.4 | K.A. IIb | 0.6 | Akypo RLM 100 | 8 | | | 3.7 | HCl |
| 128 | Gantrez ES 225 | 0.4 | K. IV b | 0.7 | Sandopan DTCAC | 10 | | | 9.2 | NaOH |
| 129 | 28.13.10 | 0.3 | K. IV b | 0.7 | Emcol E. 607 TA-2 | 3 5 | | | 5 | HCl |
| 130 | Cyanamer A 370 | 0.3 | K.A.VII b | 0.6 | Elfan OS 46 | 12 | | | 7 | HCl |
| 131 | PA-9 | 0.3 | K.A VII b | 0.6 | Remcopal 349 | 10 | | | 4.5 | NaOH |
| 132 | Hydagen F | 0.35 | K.A IXb | 0.9 | Maypon 4 CT | 10 | | | 6.8 | HCl |
| 133 | 28.13.10 | 0.5 | PD 170 | 0.5 | Tween 20 | 8 | | | 3 | HCl |
| 134 | 28.29.30 | 0.5 | AZA-6 | 0.5 | TA-I | 10 | | | 7.3 | HCl |
| 135 | Versicol K. 11 | 0.6 | AZA-7 | 0.6 | Akypo RLM 100 | 10 | | | 7 | HCl |
| 136 | Versicol E.5 | 0.4 | PEI 18 | 0.6 | trimethyl-cetyl-ammonium bromide | 5 | | | 4 | HCl |
| 137 | Gantrez ES 425 | 0.4 | Reten 210 | 0.6 | Setacin 103 Spezial | 12 | | | 7.8 | NaOH |
| 138 | 28.29.30 | 0.4 | Reten 220 | 0.6 | Setacin 103 Spezial | 12 | | | 9.1 | NaOH |
| 139 | 28.29.30 | 0.4 | Reten 220 | 0.6 | trimethyl-cetyl-ammonium bromide | 5 | | | 5.5 | HCl |
| 140 | 28.29.30 | 0.6 | Merquat 100 | 0.1 | Sandopan DTC AC | 10 | | | 8 | HCl |
| 141 | Versicol E.5 | 0.2 | Catrex | 0.5 | Hostapur SAS 30 | 12 | | | 7 | |
| 142 | Resin TV 242 | 0.4 | PD 170 | 0.15 | Pluronic L 62 | 8 | | | 9.4 | NaOH |
| 143 | Versicol E. 5 | 0.4 | Polymer G 9 | 0.6 | AST 1214 | 15 | | | 8 | NaOH |
| 144 | Flexan 500 | 0.4 | Polymer G 8 | 0.6 | AST 1214 | 15 | copra diethanolamide | 2 | 7 | NaOH |
| 145 | Flexan 130 | 0.4 | Polymer G 5 | 0.6 | AST 1214 | 15 | | | 7.5 | NaOH |
| 146 | 28.29.30 | 0.4 | Polymer G 7 | 1 | ACE | 15 | | | 6.5 | HCl |
| 147 | Gantrez ES 425 | 0.5 | Polymer G 6 | 0.5 | AES | 15 | | | 7 | NaOH |
| 148 | Gantrez ES 425 | 0.3 | Polymer G 10 | 0.3 | AST 1214 | 15 | | | 6.5 | HCl |
| 149 | lignosulphonate C. 10 | 0.4 | K I.a | 0.6 | TA-I | 10 | | | 3 | HCl |
| 150 | lignosulphonate C.14 | 0.4 | Cartaretine F4 | 0.6 | AST 1214 | 15 | | | 8 | triethanolamine |

EXAMPLE 151

A shampoo is prepared by mixing the following compounds, in a manner which is in itself known:

| | | |
|---|---|---|
| grafted and crosslinked cationic polymer PGR 1 | 0.6 | g |
| Gantrez ES 425 | 0.4 | g |
| Setacin 103 Spezial | 15 | g |
| The pH is adjusted to 8.5 with sodium hydroxide | | |
| water, q.s.p. | 100 | g |

This shampoo is applied to hair and the hair is rinsed after . . . minutes. It is found, as with compositions 1 to 43 and 70 to 151, that the wet hair combs out easily and the dry hair is glossy and free from electrostatic charge and holds well.

EXAMPLE 152

A shampoo having the following composition is prepared:

| | | |
|---|---|---|
| cationic polymer PGR 1 | 0.5 | g |
| anionic polymer P3 | 0.5 | g |
| amphoteric agent 1 | 5 | g |
| T.A-1 | 5 | g |
| pH 8.5 | | |
| water, q.s.p. | 100 | g |

After shampooing and rinsing the hair, it is found that the hair is free from electrostatic charge and holds well after drying.

On replacing the abovementioned polymer PGR 1 in the compositions of Examples 151 and 152 by the polymers PGR-2, PGR-3 and PGR-4 to PGR-17, similar results are obtained.

EXAMPLES 153 to 158

The following rinsing compositions, also referred to as "rinses", are prepared, the water being added in sufficient amount to give 100 g.

| Ex. | Anionic polymer | % | Cationic polymer | % | Surface-active agent | % | pH | Acidifying or alkalizing agent |
|---|---|---|---|---|---|---|---|---|
| 153 | Gantrez ES 425 | 0.5 | K.Ia | 1.5 | TA-1 | 0.5 | 3 | tartaric acid |
| 154 | Gantrez ES 425 | 0.2 | K Va | 0.6 | TA-1 | 1 | 7 | HCl |
| 155 | 28.29.30 | 0.6 | K.Ia | 0.5 | | | 8.6 | triethanolamine |
| 156 | Gantrez ES 425 | 0.4 | Cartaretine F4 | 1 | | | 7.5 | HCl |

-continued

| Ex. | Anionic polymer | % | Cationic polymer | % | Surface-active agent | % | pH | Acidifying or alkalizing agent |
|---|---|---|---|---|---|---|---|---|
| 157 | 28.29.30 | 0.4 | Merquat 550 | 0.4 | | | 8.2 | HCl |
| 158 | Versicol E 5 | 0.4 | Gafquat 755 | 0.6 | | | 8.3 | HCl |

On applying 20 g of each of these compositions to clean, moist and towel-dried hair, and rinsing the hair after a few minutes, it is found that the wet hair combs out easily, that the dry hair is springy and easy to style, and that the waveset holds well.

EXAMPLE 159

The following composition is prepared:

| | | |
|---|---|---|
| polymer K.Ia | 0.5 | g |
| Versicol K.11 | 0.4 | g |
| pH adjusted to 8.4 with hydrochloric acid | | |
| water, q.s.p. | 100 | cc |

This composition is used as a wavesetting lotion.

After impregnating the hair with this lotion, the hair is wound up on rollers of diameter from 15 to 30 mm and is then dried by external application of heat. After removing the rollers, a waveset which holds well is obtained, and the hair is furthermore free from electrostatic charge, and supple.

EXAMPLE 160

The following dyeing composition is prepared:

| | | |
|---|---|---|
| cetyl alcohol | 15 | g |
| sodium cetyl/stearyl-sulphate | 4 | g |
| oxyethyleneated stearyl alcohol (15 mols of ethylene oxide) | 3 | g |
| lauryl alcohol | 5 | g |
| polymer G 4 | 3 | g |
| ammonia of 22° Be strength | 10 | ml |
| meta-diaminoanisole sulphate | 0.048 | g |
| resorcinol | 0.420 | g |
| meta-aminophenol base | 0.150 | g |
| nitro-para-phenylenediamine | 0.085 | g |
| para-toluylenediamine | 0.004 | g |
| ethylenediaminetetraacetic acid sold under the name Trilon B | 1.000 | g |
| water, q.s.p. | 100 | g |

30 g of this formulation are mixed with 45 g of hydrogen peroxide of 20 volumes strength, containing 0.7% of Flexan 500.

A smooth, thick cream is obtained, which is pleasant to apply and which adheres well to the hair.

After leaving the composition on the hair for 30 minutes, the hair is rinsed, set in waves and dried. The hair is glossy and springy, and possesses body, volume and . . . (?) On 100% white hair, a blond shade is obtained.

EXAMPLES 161 to 164

The following compositions intended to be used as coloring shampoos are prepared:

TABLE V

| Ex. | Anionic polymer | % g | Cationic polymer | % g | Surface-active agent | % g | pH | Acidifying or alkalizing agent |
|---|---|---|---|---|---|---|---|---|
| 161 | P-COL | 1 | G-4 | 0.2 | TA-1 | 10 | 7 | |
| 162 | P-COL | 0.4 | Polymer Ka Xb | 0.6 | TA-2 | 10 | 8.7 | NaOH |
| 163 | P-COL | 0.5 | Cartaretine F4 | 0.5 | TA-1 | 10 | 9 | NaOH |
| 164 | P-COL | 0.6 | Merquat 550 | 0.4 | TA-1 | 10 | 9 | |

Water is added in sufficient amount to give 100 g, and 20 g of each of these compositions are then applied to the hair; after leaving the composition on the hair for 20 minutes, rinsing and drying, the following are found:

for composition 161, applied to bleached hair, a coloration with an ashen sheen;

for composition 162, applied to light blond hair, a coloration with an ashen sheen;

for composition 163, applied to light blond hair, a coloration with an ashen sheen;

for composition 164, applied to bleached hair, a coloration with an ashen sheen.

EXAMPLE 165

Treatment cream

The following composition is prepared:

| | | |
|---|---|---|
| polymer K.Ia | 0.5 | g |
| polymer 28.29.30 | 0.5 | g |
| Neutralised to pH 8 with triethanolamine stearyl alcohol oxyethyleneated with 2 mols of ethylene oxide, sold under the name Brij 72 by Messrs. Atlas | 15 | g |
| triethanolamine, q.s.p. | pH 8 | |
| water, q.s.p. | 100 | g |

20 to 40 g of this cream are applied to clean, moist and towel-dried hair. The composition is left on the hair for 5 minutes and the hair is then rinsed. The wet hair combs out easily. The dry hair is springy and easy to style, and the waveset holds well.

EXAMPLE 166

Treatment cream

The following composition is prepared:

| | | |
|---|---|---|
| Cartaretine F.8 | 1 | g |
| Gantrez ES 425 | 1 | g |
| neutralised to pH 5.5 with triethanolamine Brij 72 | 18 | g |
| tartaric acid, q.s.p. | pH 3 | |
| water, q.s.p. | 100 | g |

20 to 40 g of this cream are applied to clean, moist and towel-dried hair. The composition is left on the hair for 5 minutes and the hair is then rinsed. The wet hair combs out easily. The dry hair is springy and easy to style, and the waveset holds well.

EXAMPLE 167

Milk

The following composition is prepared:

| | | |
|---|---|---|
| polymer K. Ia | 1.5 | g |
| Gantrez ES 425 | 0.5 | g |
| Neutralised to pH 5.5 with triisopropanolamine | | |
| TA-1 | 0.5 | g |
| ACSPO | 4 | g |
| copra monoethanolamide | 1 | g |
| tartaric acid, q.s.p. | pH 3 | |
| water, q.s.p. | 100 | g |

20 to 40 g of this milk are applied to clean, moist and towel-dried hair. The composition is left on the hair for 5 minutes and the hair is then rinsed. The wet hair combs out easily. The dry hair is springy and easy to style, and the waveset holds well.

EXAMPLE 168

The following composition is prepared:

| | | |
|---|---|---|
| Cartaretine F4 | 0.5 | g |
| Versicol E.5 | 0.2 | g |
| stearic acid | 9 | g |
| coconut fatty acids | 0.8 | g |
| triethanolamine | 4.5 | g |
| pure glycerine | 5 | g |
| perfume | | |
| pH 8.5 | | |
| water, q.s.p. | 100 | g |

This composition, used as a shaving foam, is introduced into an aerosol device containing 10% by volume of the said composition and 90% by volume of a propellant gas which is a mixture of Freon F 114 and Freon 12 in the ratio of 60/40.

EXAMPLE 169

The following composition is prepared:

| | | |
|---|---|---|
| Merquat 550 | 0.1 | g |
| Hydagen F | 0.2 | g |
| stearic acid | 9 | g |
| coconut fatty acids | 0.8 | g |
| triethanolamine | 4.5 | g |
| pure glycerine | 5 | g |
| perfume | | |
| pH 8.5 | | |
| water, q.s.p. | 100 | g |

This composition constitutes a shaving foam.

The composition thus prepared is introduced into an aerosol device in the ratio of 10% by volume of the composition and 90% of a propellant gas identical to that of Example 168.

After rinsing and shaving it is found that the skin is soft and smooth to the touch.

The examples which follow are intended to illustrate one of the variants of the invention which consists of combining a cationic polymer with an anionic polymer on the hair.

EXAMPLE 170

The following two compositions are prepared:

| Composition $S_1$: | | |
|---|---|---|
| polymer Ka Xb | 1 | g |
| pH adjusted to 5 with HCl | | |
| water, q.s.p. | 100 | g |

This composition can contain a colorant intended to color the solution.

| Composition $S_2$: | | |
|---|---|---|
| neutralised Gantrez ES 425 | 0.6 | g |
| the sodium salt of a sulphuric acid half-ester of an ether obtained by oxyethyleneating a $C_{12}$—$C_{14}$-alcohol with 2.2 mols of ethylene oxide; pH adjusted to 7.5 with sodium hydroxide | 15 | g |
| water, q.s.p. | 100 | g |

This composition can contain a perfume and colorants intended to color the composition.

The first composition $S_1$, which constitutes a pre-shampoo, is applied to the hair; a few minutes after the application, the hair is rinsed with water and is shampooed with composition $S_2$. After rinsing and drying, the hair has a supple appearance, is free from electrostatic charge and lasts well.

EXAMPLE 171

The procedure indicated in Example 170 is followed, but using the following compositions $S_1$ and $S_2$:

| Composition $S_1$: | | |
|---|---|---|
| polymer IV b | 0.5 | g |
| water, q.s.p. | 100 | g |

| Composition $S_2$: | | |
|---|---|---|
| Flexan 500 | 0.5 | g |
| AST 1214 | 10 | g |
| pH 7 | | |
| water, q.s.p. | 100 | g |

Results similar to those indicated in Example 170 are found.

EXAMPLES 172 to 177

Table VI below is intended to illustrate other compositions which can be used in a two-stage process. The parts of the compositions shown below in Table No. VI are prepared separately.

20 g of part I are applied. This is left on the hair for a few minutes. 20 g of part II are then applied, without rinsing.

The hair is massaged thoroughly to ensure the homogeneity of the mixture, and is then rinsed. The wet hair combs out easily. The dry hair is springy and easy to style, and the waveset holds well.

EXAMPLES 178 to 184

The parts of the compositions shown below in Table No. VII are prepared. 20 g of part I corresponding to Examples 179 to 185 are applied and left on the hair for a few minutes. 20 g of part II corresponding to Examples 178 to 184 of Table No. VII are then applied without rinsing.

The hair is massaged thoroughly to ensure the homogeneity of the mixture, and is then rinsed. The wet hair combs out easily. The dry hair is springy and easy to style, and the waveset holds well.

TABLE VI
PROCESS FOR THE TWO-STAGE TREATMENT OF HAIR

|  | Example 172 | Example 173 | Example 174 | Example 175 | Example 176 | Example 177 |
|---|---|---|---|---|---|---|
| Part I |  |  |  |  |  |  |
| Polymer K.Ia | 0.8 g | — | — | 3 g | — | — |
| Cartaretine F. 8 | — | 0.8 g | — | — | 4 g | — |
| G. 4 | — | — | 0.8 g | — | — | 3 g |
| T.A. 1 | 10 g | 10 g | 10 g | — | — | — |
| tartaric acid, q.s.p. | pH 5.7 | pH 5.2 | pH 5.8 | pH 7.4 | pH 6.5 | — |
| water, q.s.p. | 100 g | 100 g | 100 g | 100 g | 100 g | 100 g pH 5.1 |
| Part II |  |  |  |  |  |  |
| 28.29.30 neutralized to pH 8 with triethanolamine | 0.8 g | 0.8 g | 0.8 g | — | — | — |
| Gantrez ES 425 neutralized to pH 5.5 with triethanolamine | — | — | — | 1 g | 2 g | 1 g |
| T.A. - 1 | — | — | — | 1 g | 1 g | 1 g |
| triethanolamine, q.s.p. | pH 8 | pH 8 | pH 8 | — | — | — |
| tartaric acid, q.s.p. | — | — | — | pH 5.1 | pH 5 | pH 5.1 |
| water, q.s.p. | 100 g | 100 g | 100 g | 100 g | 100 g | 100 g |

TABLE VII
TWO-STAGE TREATMENT OF HAIR

|  | Example 178 | Example 179 | Example 180 | Example 181 | Example 182 | Example 183 | Example 184 |
|---|---|---|---|---|---|---|---|
| Part I: |  |  |  |  |  |  |  |
| Merquat 100 | 1 g | 1 g |  |  |  |  |  |
| polymer G. 5 |  |  | 1 g | 1 g |  |  |  |
| Onamer M |  |  |  |  | 1 g | 1 g |  |
| G-12 |  |  |  |  |  |  | 1 g |
| spontaneous pH | 5.8 | 5.8 | 6.7 | 6.7 | 7.3 | 7.3 | 6.3 |
| water, q.s.p. | 100 g | 100 g | 100 g | 100 g | 100 g | 100 g | 100 g |
| Part II: |  |  |  |  |  |  |  |
| Gantrez ES 425 100% neutralized with sodium hydroxide | 1 g |  | 1 g |  | 1 g |  |  |
| Flexan 500 |  | 1 g |  |  |  |  |  |
| polymer 28.29.30 100% neutralized with triethanolamine |  |  |  | 1 g |  | 1 g |  |
| Versicol E. 5 |  |  |  |  |  |  | 1 g |
| spontaneous pH | 7.3 | 7.2 | 7.3 | 7.7 | 7.3 | 7.7 | 3 |
| water, q.s.p. | 100 g | 100 g | 100 g | 100 g | 100 g | 100 g | 100 g |

EXAMPLE 185

The following compositions are prepared in the same manner as for Examples 172 to 184:

| Composition S₃: | |
|---|---|
| G 14 | 1 g |
| monoethanolamine, q.s.p. | pH 6.3 |
| water, q.s.p. | 100 g |

| Composition S₄: | |
|---|---|
| Resin TV 242, 100% neutralized pH adjusted to 6.4 with sodium hydroxide | 1 g |
| water, q.s.p. | 100 g |

On successively applying these two compositions to the hair, similar results are those mentioned for Examples 172 to 184 are observed.

EXAMPLE 186

The same procedure as that indicated in Example 185 is followed, using successively, in the order shown below, the following compositions:

| Composition S₅: | |
|---|---|
| Reten 220 | 1.25 g |
| pH 7 |  |
| water, q.s.p. | 100 g |

| Composition S₆: | |
|---|---|
| Reten 421 | 1 g |
| pH 3 |  |
| water, q.s.p. | 100 g |

As before, it is found that the hair holds better and is easy to comb.

EXAMPLES 187 to 193

The examples which follow are intended to illustrate shampooing procedures which consist of applying successively, and in the order indicated, parts I and II shown in the table which follows.

First of all, the wet hair is impregnated with part I and after waiting for a few minutes, the hair is rinsed and then part II is applied, impregnating the hair thoroughly. After waiting for a few minutes (about 10 minutes) the hair is rinsed and dried.

The wet treated hair is easy to comb out and the dry hair is springy and free from electrostatic charge and holds well.

TABLE VIII

EXAMPLES OF SHAMPOOS

| Ex. No. | PART I Polymer | % g | Surface active agent | % g | pH | Acid or base | PART II Polymer | % g | Surface-active agent | % g | pH | Acid or base |
|---|---|---|---|---|---|---|---|---|---|---|---|---|
| 187 | JR 400 | 0.5 | AST 1214 | 15 | 8.1 | | Resin TV 242 | 0.5 | TA-1 | 10 | 5 | |
| 188 | AZA-1 | 1 | TA-2 | 10 | 7 | | Gantrez ES 425 | 0.5 | Akypo RLM 100 | 10 | 7 | |
| 189 | KI | 1 | TA-1 | 10 | 6 | | Gantrez ES 425 | 0.5 | Akypo RLM 100 | 10 | 7.5 | |
| 190 | Polymin P | 1 | TA-1 | 10 | 7 | HCl | Gantrez ES 425 | 0.5 | AST 1214 | 10 | 7 | HCl |
| 191 | Onamer M | 0.5 | TA-1 | 10 | 7.5 | NaOH | 28.29.30 | 0.5 | AST 1214 | 10 | 7 | HCl |
| 192 | poly-(1-butyl-4-vinyl-pyridinium bromide) | 0.6 | TA-1 | 10 | 6 | NaOH | 28.29.30 | 0.5 | AST 1214 | 15 | 7 | NaOH |
| 193 | Catrex | 0.6 | Myrj 53 | 10 | 7.5 | | Gantrez ES 225 | 0.3 | Sandopan DTC | 8 | 7 | |

EXAMPLE 194

The following compositions are prepared:

| Composition S$_7$: | | |
|---|---|---|
| adipic acid/dimethylaminohydroxypropyl/diethylenetriamine copolymer sold under the name Cartaretine F.4 by Messrs. Sandoz | 0.8 | g |
| vinyl acetate/crotonic acid/vinyl neodecanoate terpolymer sold under the name Resin 28.29.30 by Messrs. National Starch (pH 8 with triethanolamine) | 0.8 | g |
| TA-1 | 10.0 | g |
| monoethanolamine, q.s.p. | pH | 9.5 |
| water, q.s.p. | 100 | ml |

The pH of composition S$_7$ is chosen to prevent the precipitation of the two polymers.

| Composition S$_8$: | | |
|---|---|---|
| tartaric acid, q.s.p. | pH | 2.5 |
| water, q.s.p. | 100 | ml |

20 ml of composition S$_7$ are applied to soft and fine hair.

After waiting for a few minutes, composition S$_8$ is applied, whilst massaging the hair so as to mix the two parts well. This gives a pH of 7, at which the two polymers present precipitate on the hair.

The composition is left on the hair for 10 minutes, and the hair is then rinsed with water, set in waves and dried.

The dried hair proves strengthened; it is springy and glossy, and has body and volume.

EXAMPLE 195

The same procedure as that indicated in Example 194 is followed, but replacing the Cartaretine F. 4 by polymer K. Ia. The same results are obtained.

EXAMPLE 196

The following compositions are prepared:

| Composition S$_9$: | |
|---|---|
| Cartaretine F. 8 | 3 g |
| Gantrez ES 425 | 1 g |
| neutralized to pH 5.5 with triethanolamine | |
| tartaric acid, q.s.p. | pH 3 |
| TA-1 | 1 g |
| water, q.s.p. | 100 g |

| Composition S$_{10}$: | |
|---|---|
| 5% strength monoethanolamine | 22 g |
| pH 10.8 | |
| water, q.s.p. | 100 g |
| pH S$_9$ + S$_{10}$ : 5.6 | |

The same results as with compositions S$_7$ and S$_8$ of Example 194 are obtained.

EXAMPLE 197

The following compositions intended for permanent waving are prepared:

| Composition S$_{11}$: | |
|---|---|
| Reducing liquid | |
| thioglycollic acid | 3 g |
| thiolactic acid | 2 g |
| ammonia of 22° Be strength | 4 g |
| triethanolamine | 3.5 g |
| Cartaretine F.8 | 1 g |
| perfume | |
| colorant | |
| water, q.s.p. | 100 g |

| Composition S$_{12}$: | |
|---|---|
| Fixative liquid: | |
| potassium bromate | 9.5 g |
| Flexan 130 | 1 g |
| tartaric acid | pH 6.5 |
| perfume | |
| colorant | |
| water, q.s.p. | 100 g |

The reducing liquid can be applied very easily to sensitised hair and penetrates deeply into the hair.

After rinsing, and applying the fixative liquid, very pronounced and very regular curls are observed.

After drying, the hairstyle holds particularly well.

EXAMPLES 198 to 200

The following compositions are prepared:

|  | Example 198 | Example 199 | Example 200 |
|---|---|---|---|
| Cartaretine F.8 | 1.5 g | 6 g | 1.5 g |
| Gantrez ES 425 neutralized to pH 7.5 with triisopropanolamine | 0.5 g | 3 g | 0.5 g |
| TA-1 | 0.5 g | 3 g | — |
| tartaric acid, q.s.p. | pH 3 | pH 3 | pH 3 |
| water, q.s.p. | 100 g | 100 g | 100 g |

The compositions are lyophilised.

EXAMPLE 201

The same procedure is employed for the following composition:

| Cartaretine F. 8. | 1.5 | g |
|---|---|---|
| 28.29.30 neutralized to pH 8 with triethanolamine | 0.5 | g |
| sodium hydroxide, q.s.p. | pH | 9.9 |
| water, q.s.p. | 100 | g |

The composition is lyophilized.

At the time of use, 0.5 g of lyophilizate of Example 198, 200 or 201 is introduced into 25 g of water and applied to the hair. The hair treated in this way and then dried is springy and holds well.

0.12 g of lyophilizate of Example 199 is introduced into 25 g of water and applied to the hair. Similar results are found.

EXAMPLES 202 to 206

The following examples are intended to illustrate a variant of the invention which consists in first forming a complex with the anionic polymer and the cationic polymer and in then applying it to the hair by means of an agent which permits transfer and fixing.

EXAMPLE 202

The following composition is prepared:

1 g of the product resulting from complexing the chloride of polymer G-12 with the polymer sold under the name Aristoflex A, the two polymers being present in stoichiometric proportions, is mixed with 15 g of the surface-active agent sold under the name AKYPO RLM 100. The pH is adjusted to 8 with sodium hydroxide solution and water is added to make the composition up to 100 g. Perfume and colorants for coloring the composition are also introduced. The composition thus prepared is applied to the hair, and the hair is impregnated therewith. After rinsing and drying, the hair holds well. Similar results are obtained by applying the following compositions:

TABLE IX

| Ex. | Complex Anionic polymer | Complex Cationic polymer | % g | Surface-active agent | % | pH | Acid or base |
|---|---|---|---|---|---|---|---|
| 203 | 28.29.30 | G-4 | 0.9 | Akypo RLM 100 | 10 | 8.2 | NaOH |
| 204 | sodium salt of carboxymethylcellulose | G-12 | 1 | AST 1214 | 12 | 3 | HCl |
| 205 | Flexan 500 | G-4 | 1 | AST 1214 | 25 | 7.5 | NaOH |
| 206 | Flexan 130 | G-4 | 1.5 | AST 1214 | 15 | 7.8 | NaOH |

EXAMPLES 207 to 209

A wave-set which lasts well, and shows virtually no powdering, is obtained with the following compositions (Table X), applied to moist and towel-dried hair, in accordance with the usual processes.

| Ex. | Anionic polymer | % g | Cationic polymer | % g | Solvent | d° alcohol strength | pH |
|---|---|---|---|---|---|---|---|
| 207 | Gantrez ES 425 | 1 | Gafquat 734 | 1 | ethyl alcohol | 10° | 8.3 |
| 208 | " | 1 | KIa | 1 | ethyl alcohol | 70° | 9.2 |
| 209 | " | 1 | Cartaretine F8 | 1 | ethyl alcohol | 10° | 8.9 |

Water is added in sufficient amount to give 100 g.

EXAMPLES 210 to 212

The compositions illustrated in Table XI below are prepared:

| Ex. | Anionic polymer | %g | Cationic polymer | %g | Surface-active agent | %g | Solvent | pH |
|---|---|---|---|---|---|---|---|---|
| 210 | Gantrez ES 425 | 1 | Cartaretine F8 | 1 |  |  | 10° ethyl alcohol | 8.9 |
| 211 | 28.29.30 | 0.5 | Cartaretine F4 | 0.5 | TA-1 | 0.5 | 50° ethyl alcohol | 9.5 |
| 212 | P3 | 0.25 | Cartaretine F4 | 0.5 |  |  | 50° ethyl alcohol | 9.5 |

Each of these compositions is applied to the nails and after drying, which requires a few minutes, the latter are found to have been strengthened.

EXAMPLES 213 to 217

The shampoos having the compositions shown below were prepared.

| Ex. | Polymer Anionic | % g | Cationic | % g | Surface-active agent | % g | pH | Alkalizing or acidifying agent |
|---|---|---|---|---|---|---|---|---|
| 213 | 28.29.30 | 0.4 | K.Ia | 0.6 | Amphosol DMC/MCA | 8 | 8.8 | HCl |
| 214 | 28.29.30 | 0.4 | K.Ia | 0.6 | Steinapon AMB 13 Dehyton AB 30 | 8 | 8.5 | HCl |
| 215 | 28.29.30 | 0.4 | K.Ia | 0.6 | Amphotere 1 | 10 | 8 | HCl |
| 216 | Gantrez ES 425 | 0.2 | KAXb | 0.3 | Deriphat 160 | 10 | 7.5 | HCl |
| 217 | Gantrez ES 425 | 0.4 | KAXb | 0.6 | Aromox DM 14 TA-1 | 5 5 | 8.5 | HCl |

The hair is impregnated with one of these various shampoos and after waiting for a few minutes the hair is rinsed.

It is found that the wet hair combs out easily, has a beautiful lustre and is not sticky.

The dry hair is glossy and free from electrostatic charge, and holds well.

We claim:

1. A composition suitable for the treatment of keratin materials, which composition is intended to be rinsed out after application, said composition comprising at least one anionic polymer containing at least one of a sulfonic acid, carboxylic acid and phosphoric acid unit, said anionic polymer having a molecular weight of from about 500 to 5 million; at least one cationic polymer in a solvent medium, said anionic and said cationic polymers each being present in an amount from about 0.01 to about 10% relative to the total weight of the composition; at least one of an anionic, cationic, non-ionic or amphoteric surface-active agent or a mixture thereof present in an amount from about 0.1 to 70% by weight relative to the total weight of the composition.

2. A composition according to claim 1 which comprises an aqueous solvent medium.

3. A composition according to claim 1 which also comprises a solvent which is a monoalcohol, polyalcohol, glycoester, a fatty acid ester, methylene chloride, or a mixture thereof.

4. A composition according to claim 1 in which the cationic polymer is a polymer which contains primary, secondary, tertiary or quaternary amino units and has a molecular weight of 500 to 2 million.

5. A composition according to claim 1 in which the cationic polymer is:

(1) a quaternary derivative of a cellulose ether;
(2) a water-soluble cyclopolymer which is a homopolymer or copolymer comprising recurring units of the formula:

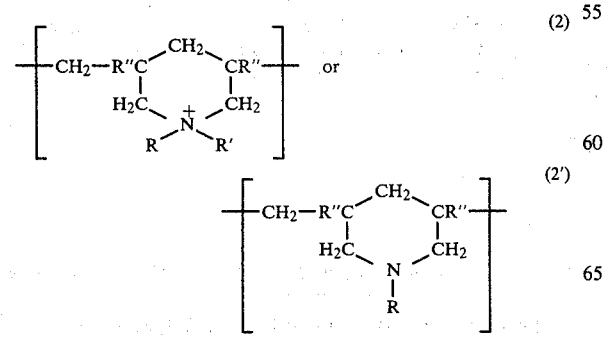

in which R" denotes hydrogen or methyl, and R and R' independently of one another denote an alkyl group having 1 to 22 carbon atoms, a hydroxyalkyl group or an amidoalkyl group, or R and R', together with the nitrogen atom to which they are linked, denote a heterocyclic group, the units of formula (2) comprising a cosmetically acceptable anion;

(3) a cationic homopolymer or copolymer comprising recurring units of the formula:

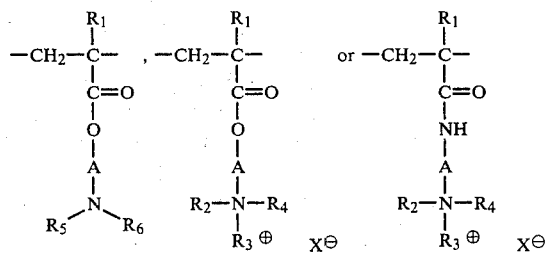

in which $R_1$ is H or $CH_3$, A is a linear or branched alkyl group having up to 6 carbon atoms or a hydroxyalkyl group having 1 to 4 carbon atoms, $R_2$, $R_3$ and $R_4$ are independently an alkyl group having 1 to 18 carbon atoms or benzyl, $R_5$ and $R_6$ denote H or alkyl having 1 to 6 carbon atoms and X denotes halogen or methosulphate;

(4) a cationic polymer having recurring units of the formula —A—Z—A—Z—, in which A denotes a radical having two amino groups and Z denotes the symbol B or B', which symbols may be identical or different and denote an alkylene radical which is unsubstituted or substituted by hydroxyl groups and which can additionally contain chain oxygen, nitrogen or sulphur atoms and 1 to 3 aromatic and/or heterocyclic rings; or having recurring units of the formula —A—$Z_1$—A—$Z_1$—, in which A is as defined above and $Z_1$ denotes the symbol $B_1$ or $B'_1$ such that at least one $Z_1$ denotes $B'_1$, $B_1$ being an alkylene or hydroxyalkylene radical and $B'_1$ being an alkylene radical which is unsubstituted or substituted by one or more hydroxyl radicals and contains one or more chain nitrogen atoms which are substituted by an alkyl radical which optionally contains a chain oxygen atom and contains one or more hydroxyl and/or carboxyl groups; or having recurring units of the formula —A'—Z'—A'—Z'—, in which A' denotes a mixture of radicals:

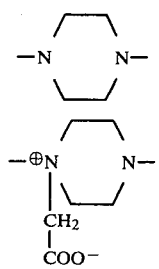

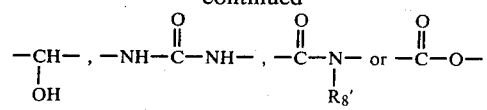

and Z′ is as defined above for $B_1$, B, B′ or $B'_1$; and the quaternary ammonium salts and oxidation products of the polymers —A—Z—A—Z— and —A—$Z_1$—A—$Z_1$—;

(5) a quaternary polymer comprising recurring units of the formula:

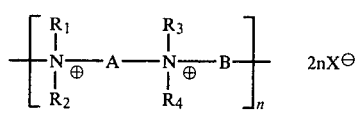

in which $R_1$, $R_2$, $R_3$ and $R_4$ independently represent an aliphatic, alicyclic or araliphatic radical containing at most 20 carbon atoms or a lower hydroxyaliphatic radical, or $R_1$ and $R_2$, and $R_3$ and $R_4$, together or separately, form, together with the nitrogen atoms to which they are linked, a heterocyclic ring which optionally contains a second heteroatom other than nitrogen, or $R_1$, $R_2$, $R_3$ and $R_4$ independently represent a group of the formula:

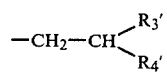

$R'_3$ denoting hydrogen or lower alkyl and $R'_4$ denoting —CN,

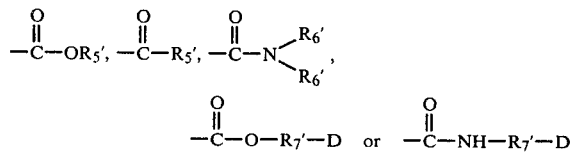

where $R'_5$ denotes lower alkyl, $R'_6$ denotes hydrogen or lower alkyl, $R'_7$ denotes alkylene and D denotes a quaternary ammonium group, and A and B independently represent a hydrocarbon group which contains 2 to 20 carbon atoms and which can be linear or branched, and saturated or unsaturated and can contain, interposed in the main chain, one or more aromatic rings or one or more groups —CH₂—Y—CH₂— in which Y denotes —O—, —S—, —SO—, —SO₂—, —S—S—,

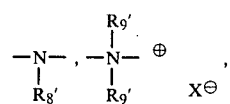

in which $R'_8$ denotes hydrogen or lower alkyl and $R'_9$ denotes lower alkyl, or A and $R_1$ and $R_3$, together with the two nitrogen atoms to which they are linked, form a piperazine ring, and B can also denote

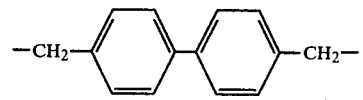

and $X^-$ is a mineral or organic acid anion or

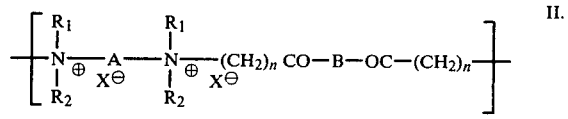

in which A denotes a linear or branched, saturated or unsaturated alkylene or hydroxyalkylene radical, B denotes
(a) a radical of the formula —O—Z—O—, where Z denotes a linear or branched hydrocarbon radical or a group of the formula:

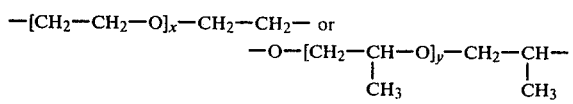

where x and y independently denote an integer from 1 to 4 or, in a mixture of compounds, any number from 1 to 4;
(b) a radical of a bis-secondary diamine;
(c) a radical of a bis-primary diamine of the formula:

where Y denotes a linear or branched hydrocarbon radical or the divalent radical —CH₂—CH₂—S—S—CH₂—CH₂—; or
(d) a ureylene group of the formula —NH—CO—NH—, $R_1$ denotes an alkyl radical having from 1 to 4 carbon atoms, $R_2$ denotes a linear or branched hydrocarbon radical containing from 1 to 12 carbon atoms, such that $R_2$ can also denote a plurality of methylene groups linked to one another and form with A, if A denotes an ethylene radical, and with the two nitrogen atoms, a divalent radical of the formula:

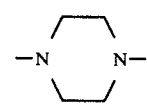

$X^-$ denotes a halide and n denotes the number 1 or an integer from 3 to 10;
(6) a copolymer comprising recurring units of the formulae:

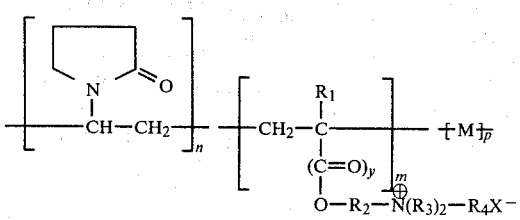

in the proportions n:m:p such that n represents 20 to 99 mol %, m from 1 to 80 mol %, and p 0 to 50 mol %, with n+m+p=100, y denotes 0 or 1, and $R_1$ represents H or $CH_3$; $R_2$ denotes $-CH_2-CHOH-CH_2-$ or $C_xH_{2x}$, where x is from 2 to 18; $R_3$ denotes $CH_3$, $C_2H_5$ or

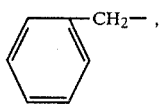

$R_4$ denotes $CH_3$ or $C_2H_5$, X denotes Cl, Br, I, $\frac{1}{2}SO_4$, $HSO_4$ or $CH_3SO_4$ and M is derived from a further monomer;

(7) an optionally crosslinked polyaminoamide;
(8) an optionally alkoxylated or alkylated polyalkyleneamine;
(9) a polymer containing chain vinylpyridine or vinylpyridinium units;
(10) a urea-formaldehyde cationic resin;
(11) a polyamine/epichlorohydrin condensate;
(12) a vinylbenzylammonium homopolymer or copolymer;
(13) a quaternary polyureylene; and
(14) a coloring polymer in the form of a mixture of water-soluble cationic polymers which contain secondary or tertiary amino groups or quaternary ammonium groups which either form part of, or are attached directly or indirectly to, compounds which carry chromophoric or chromogenic aryl or araliphatic groups, provided that if the main chain contains amino groups which form part of said chromophoric or chromogenic compounds, it necessarily also contains at least 10% of aliphatic amino groups to the total number of amino groups of the polymer chain.

6. A composition according to claim 5, in which the crosslinked polyaminoamide is either:
   (a) a crosslinked, alkylated or non-alkylated, polyamino-amide obtained by crosslinking a polyaminoamide which is a polycondensation product of an acid with a polyamine, with a crosslinking agent which is an epihalohydrin, a diepoxide, a dianhydride, an unsaturated anhydride or a bis-unsaturated compound, in an amount from 0.025 to 0.35 mol per amino group of the polyaminoamide;
   (b) a water-soluble crosslinked polyaminoamide obtained by crosslinking a polyaminoamide as defined above, with a crosslinking agent which is:
      I. a bis-halohydrin, a bis-azetidinium compound, a bis-haloacyl substituted diamine or a bis-alkyl halide;
      II. an oligomer obtained by reacting a compound of group I, or an epihalohydrin, diepoxide or bis-unsaturated compound, with a bifunctional compound;
      III. a quaternization product of a compound of group I or of an oligomer of group II which contains a tertiary amino group which can be alkylated, with an alkylating agent in an amount from 0.025 to 0.35 mol per amine group of the polyaminoamide;
   (c) a water-soluble polyaminoamide which is a condensation product of a polyalkylene-polyamine with a polycarboxylic acid followed by alkylation by a bifunctional agent of the formula:

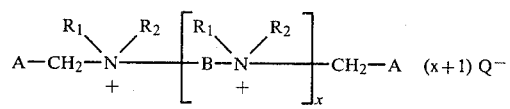

where x denotes 0 or an integer from 1 to 7, A denotes a

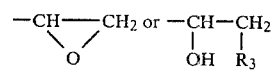

group, $R_3$ denotes halogen, $R_1$ and $R_2$ independently denote a lower alkyl or hydroxyalkyl group, $Q^-$ denotes halogen, sulphate or methosulphate, B represents an alkylene radical or a

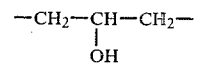

or $-(CH_2)_y-NH-CO-NH-(CH_2)_y-$ radical and y is an integer from 1 to 4, or
   (d) a polymer which is a reaction product of a polyalkylenepolyamine containing two primary amino groups and at least one secondary amino group, with a dicarboxylic acid which is diglycollic acid or a saturated aliphatic dicarboxylic acid having 3 to 8 carbon atoms, the molar ratio of the polyalkylenepolyamine to the dicarboxylic acid being from 0.8:1 to 1.4:1, and reacting the resulting polyamide with epichlorohydrin in a molar ratio of epichlorohydrin to the secondary amino group of the polyamide of from 0.5:1 to 1.8:1.

7. A composition according to claim 1 in which the anionic polymer is a polymer containing recurring units derived from one of the following acids or a salt or derivative of said acids:
   (a) sulphonic acid, in which case the polymer is a salt of a polystyrenesulphonic acid or an alkali metal or alkaline earth metal salt of a lignin sulphonic acid,
   (b) crotonic acid,
   (c) acrylic or methacrylic acid,
   (d) ethylene-$\alpha,\beta$-dicarboxylic acid, or
   (e) allyloxyacetic acid, methallyloxyacetic acid, 3-allyloxypropionic acid, allylthioacetic acid, allylaminoacetic acid, vinylacetic acid, vinyloxyacetic acid, crotyloxyacetic acid, 3-butenoic acid, 4-pentenoic acid, 10-undecenoic acid, allylmalonic acid, maleamic acid, itaconamic acid or N-monohydroxyalkyl- or N-dihydroxy-alkyl-maleamic acids, or a salt or derivative thereof.

8. A composition according to claim 7 in which the crotonic acid-derived-polymer is:
   (a) a graft polymer obtained from a vinyl ester and an acrylic or methacrylic acid ester, alone or as a mixture copolymerized with crotonic acid, grafted onto a polyalkylene glycol of which the terminal OH groups are optionally etherified or esterified, or onto an oxide of a nitrogen-containing polyalkylene glycol;

(b) a grafted and crosslinked polymer resulting from the copolymerization of a non-ionic monomer, crotonic acid, polyethylene glycol and a crosslinking agent;

(c) a terpolymer derived from crotonic acid, vinyl acetate and an allyl or methallyl ester of the formula:

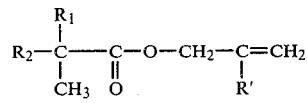 (11)

in which R' represents a hydrogen or a —CH$_3$ radical, R$_1$ represents a saturated linear or branched hydrocarbon chain having from 1 to 6 carbon atoms and R$_2$ represents either the —CH$_3$ radical or the —HC(CH$_3$)$_2$ radical;

(d) a tetrapolymer or pentapolymer resulting from the copolymerization of crotonic acid, vinyl acetate or vinyl propionate, an allyl or methallyl ester of formula (11), and a monomer which is a vinyl ether of the formula CH$_2$=CH-O-R$_3$, (12) where R$_3$ denotes an alkyl radical, a vinyl ester of the formula (13)

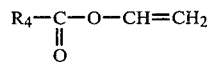

where R$_4$ is a linear alkyl radical having from 7 to 11 carbon atoms, or an allyl or methallyl ester of the formula: (14)

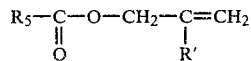

where R' is a hydrogen atom or a methyl radical and R$_5$ is an alkyl radical;

(e) a terpolymer of vinyl acetate, crotonic acid and a vinyl ester of an α-branched saturated aliphatic monocarboxylic acid having at least 5 carbon atoms in the carboxyl radical.

9. A composition according to claim 7 in which the crotonic-derived polymer is:

(a) a copolymer obtained by copolymerizing an ester of an unsaturated alcohol with a short-chain saturated acid or an ester of a short-chain saturated alcohol with an unsaturated acid; crotonic acid; and an ester of a long-chain acid with an unsaturated alcohol, an ester of an unsaturated acid with a saturated or unsaturated alcohol containing 8 to 18 carbon atoms or with a lanolin alcohol, an alkylvinyl ether, an alkylallyl ether, an alkyl methallyl ether, an alkyl crotyl ether or an α-olefine;

(b) a homopolymer of crotonic acid or a copolymer of crotonic acid with an unsaturated monoethylenic monomer;

(c) a copolymer of vinyl acetate, crotonic acid and an acrylic or methacrylic ester or an alkyl vinyl ether;

(d) a copolymer of vinyl acetate, crotonic acid and a vinyl, allyl or methallyl ester containing a long carbon chain.

10. A composition according to claim 7 in which the acrylic acid or methacrylic acid-derived polymer is:

(a) a graft polymer obtained by grafting a vinyl ester, acrylic acid ester or methacrylic acid ester, alone or as a mixture, copolymerised with acrylic acid or methacrylic acid, onto an optionally etherified or esterified polyalkylene glycol or onto an oxide of a nitrogen-containing polyalkylene glycol;

(b) a grafted and crosslinked polymer resulting from the copolymerization of a non-ionic monomer, acrylic or methacrylic acid, polyethylene glycol and a crosslinking agent;

(c) a terpolymer, tetrapolymer, pentapolymer or higher polymer of a monomer of the formula:

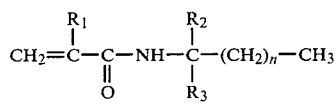 (15)

in which R$_1$, R$_2$ and R$_3$ represent hydrogen or methyl and n is 0 or an integer from 1 to 10, a water-soluble monomer:

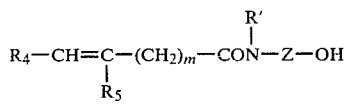 (16)

in which R' represents hydrogen or methyl, Z represents a linear or branched alkylene radical optionally substituted by one or two hydroxymethyl groups, m is equal to 0 or 1, R$_4$ denotes H or COR$_6$, where R$_6$ is OH or —NH—R$_7$ denotes H or —Z—OH and R$_5$ denotes H or CH$_3$, if m=0, or R$_4$ denotes H and R$_5$ denotes COR$_6$, R$_6$ being as defined above, if m=1, and acrylic acid or methacrylic acid, optionally together with one or more copolymerisable monomers;

(d) a N-tertiary butyl-acrylamide or N-isopropyl-acrylamide/acrylamide or methacrylamide/acrylic or methacrylic acid/N-vinylpyrrolidone terpolymer.

11. A composition according to claim 7 in which the acrylic acid or methacrylic acid-derived polymer is:

(a) a water-soluble polymer of acrylic acid or methacrylic acid and/or a copolymer of said acid with a monoethylenic unsaturated monomer, (b) a homopolymer of acrylic acid crosslinked by means of a polyfunctional-crosslinking agent, (c) a copolymer of acrylic acid or methacrylic acid with acrylamide, (d) a copolymer of acrylic acid or methacrylic acid with vinyl alcohol, (e) a polyacrylamide containing carboxylate groups, (f) a copolymer derived from 40 to 90 mol % of vinylpyrrolidone, 40 to 50 mol % of a vinyl ester and 20 to 30 mol % of acrylic acid or methacrylic acid.

12. A composition according to claim 7 in which the ethylene-α,β-dicarboxylic acid-derived polymer is:

(a) a copolymer of said acid with a compound containing a >C=CH$_2$ group, which is a vinyl ester, a C$_1$-C$_4$ alkyl vinyl ether, a phenylvinyl derivative of acrylic acid, (b) a $C_1$–$C_8$ half-ester of a said copolymer derived under (a), (c) a copolymer of said acid with an olefine having 2 to 4 carbon atoms, which copolymers are partially esterified with an alkanol, (d) a copolymer of said acid with an allyl or methallyl ester, which copolymers are mono-esterified with an aliphatic alcohol or amidified with an aliphatic, cyclic or heterocyclic amine or (e) a terpolymer of said acid with an allyl or methallyl ester and an acrylamide or methacrylamide, in which the acid groups are mono-esterified or amidified; or a polymer derived from said monomers and an α-olefine, vinyl ether or acrylic or methacrylic ester and optionally acrylic or methacrylic acid or N-vinylpyrrolidone, (f) a terpolymer, tetrapolymer and pentapolymer of a said acid and a monomer of the formula:

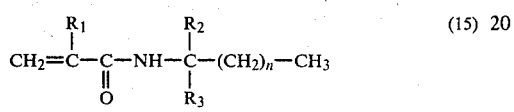 (15)

in which $R_1$, $R_2$ and $R_3$ represent hydrogen or methyl and n is 0 or an integer from 1 to 10, a water-soluble monomer of the formula:

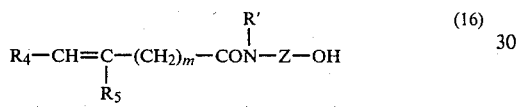 (16)

in which R' represents hydrogen or methyl, Z represents a linear or branched alkylene radical optionally substituted by one or two hydroxymethyl groups, m is 0 or 1, $R_4$ denotes H or —$COR_6$, where $R_6$ is OH or —NH—$R_7$, $R_7$ denoting H or —Z—OH, and $R_5$ denotes H or $CH_3$, if m=0, or $R_4$ denotes H and $R_5$ denotes $COR_6$, $R_6$ being as defined above, if m=1, and maleic anhydride;

(g) a polymer resulting from the polymerization of a said acid, a monomer of formula (15), a monomer of the formula:

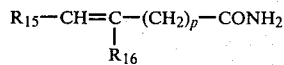

where $R_{15}$ denotes H or COOH and $R_{16}$ denotes H or $CH_3$ if p=0, or $R_{15}$ denotes H and $R_{16}$ denotes COOH if p=1, and maleic anhydride, and optionally other monomers, (h) a coloured maleic anhydride polymer.

13. A composition according to claim 7 in which the anionic polymer is:

(a) a grafted and crosslinked copolymer resulting from the copolymerization of at least one non-ionic monomer, allyloxyacetic or vinylacetic acid, polyethylene glycol and a crosslinking agent, (b) a copolymer obtained by copolymerizing: an ester of an unsaturated alcohol with a short-chain saturated carboxylic acid or an ester of a short-chain saturated alcohol with an unsaturated acid, an unsaturated acid which is 3-butenoic acid, 4-pentenoic acid, 10-undecenoic acid, allylmalonic acid, allyloxyacetic acid, crotyloxyacetic acid, methallyloxyacetic acid, 3-allyloxypropionic acid, allylthioacetic acid, allylaminoacetic acid or vinyloxyacetic acid, and an ester of a long-chain acid with an unsaturated alcohol, or an ester of said unsaturated acids with a linear or branched saturated or unsaturated alcohol, (c) a tetra- or penta-polymer resulting from the copolymerization of allyloxyacetic acid, vinyl acetate or propionate, an allyl or methallyl ester of formula (11), and a monomer which is a vinyl ether of the formula $CH_2=CH-O-R_3$, where $R_3$ denotes an alkyl radical, a vinyl ester of the formula:

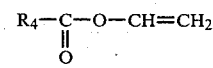

where $R_4$ is a linear alkyl radical having from 7 to 11 carbon atoms, or an allyl or methallyl ester of the formula:

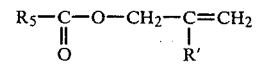

where R' is a hydrogen atom or a methyl radical and $R_5$ is an alkyl radical, (d) a copolymer obtained by copolymerizing at least one monomer of formula (15), N-monohydroxyalkyl- or N-dihydroxy-alkylmaleamic or -itaconamic acid, and N-vinylpyrrolidone or an acrylate or methacrylate of the formula:

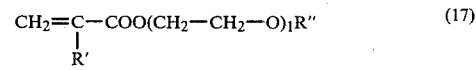 (17)

in which R' denotes H or methyl, l is 3 or 4 and R" is methyl or ethyl, optionally together with another monomer, (e) a copolymer obtained by copolymerizing at least one monomer of formula (15), maleamic or itaconamic acid, a monomer of formula (16) or (17) and, optionally, one or more other monomers.

14. A composition according to claim 1 which also contains an oxidation dyestuff or a direct dyestuff which is a nitrobenzene dyestuff, and has a pH from 9 to 11.

15. A composition according to claim 1 which contains a non-ionic or cationic surface-active agent which is a condensation product of a monoalcohol, an α-diol, an alkylphenol or an amide with glycidol, or a polyethoxylated or polyglycerolated alcohol, an alkylphenol or a fatty acid having a linear fatty chain of 8 to 18 carbon atoms, in an amount up to 20% by weight, the pH of the composition being from 2 to 9.5.

16. A composition according to claim 1 in which the non-ionic surface-active agent has the formula:

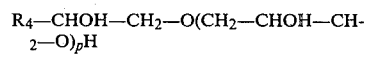

in which $R_4$ denotes an aliphatic, cycloaliphatic or araliphatic radical having 7 to 21 carbon atoms, with the aliphatic chains optionally containing chain ether, thioether or hydroxymethylene groups, and p is from 1 to 10.

17. A composition according to claim 1 in which the cationic polymer is present in an amount from 0.05 to 5% by weight.

18. A composition according to claim 1 in which the anionicpolymer is present in an amount from 0.02 to 5% by weight.

19. A composition suitable for the treatment of keratin materials, which composition is intended to be rinsed out after application, said composition comprising at least one anionic polymer containing at least one of a sulfonic acid, carboxylic acid and phosphoric acid unit, said anionic polymer having a molecular weight of from about 500 to 5 million; at least one cationic polymer in a solvent medium, said anionic and said cationic polymers each being present in an amount from about 0.01 to about 10% relative to the total weight of the composition; a soap present in an amount from about 10 to 30% by weight; an oxyethlenated or polyglycerolated fatty alcohol emulsifier in an amount from about 0.5 to 25% by weight; an oxyethyleneated alkyl-sulphate is an amount from about 0.05 to 15% by weight, a fatty amide in an amount from 0 to 10% by weight; a fatty alcohol in an amount from 0 to 25% by weight; and an alkalizing agent.

20. A composition suitable for the treatment of keratin materials, which composition is intended to be rinsed out after application, said composition comprising at least one anionic polymer containing at least one of a sulfonic acid, carboxylic acid and phosphoric acid unit, said anionic polymer having a molecular weight of from about 500 to 5 million; at least one cationic polymer in a solvent medium, said anionic and said cationic polymers each being present in an amount from about 0.01 to about 10% relative to the total weight of the composition; a natural or synthetic alcohol having 12 to 18 carbon atoms in an amount from about 0.5 to 25% by weight; an oxyethyleneated or polyglcerolated fatty alcohol emulsifier present in an amount from about 0.5 to 25% by weight; an oxyethleneated alkyl-sulphate in an amount from about 0.5 to 15% by weight; and a fatty amide in an amount from 0 to 10% by weight.

21. A composition suitable for the treatment of keratin materials, which composition is intended to be rinsed out after application, said composition comprising at least one anionic polymer containing at least one of a sulfonic acid, carboxylic acid and phosphoric acid unit, said anionic polymer having a molecular weight of from about 500 to 5 million; at least one cationic polymer in a solvent medium, said anionic and said cationic polymers each being present in an amount from about 0.01 to about 10% relative to the total weight of the composition, said composition in the form of a non-ionic or anionic emulsion based on oils, fatty alcohols or mixtures thereof; and further comprising at least one of a polyoxyethyleneated fatty alcohol and a soap.

22. A composition suitable for the treatment of keratin materials comprising in a solvent medium at least one anionic polymer containing at least one of a sulfonic acid, carboxylic acid and phosphoric acid unit having a molecular weight of from about 500 to 5 million and at least one cationic polymer selected from the group consisting of (1) a water-soluble cyclopolymer which is a homopolymer or copolymer comprising recurring units of the formula:

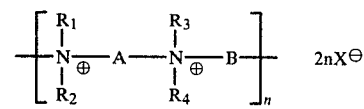

in which R″ denotes hydrogen or methyl, and R and R′ independently of one another denote an alkyl group having 1 to 22 carbon atoms, a hydroxyalkyl group or an amidoalkyl group, or R and R′, together with the nitrogen atom to which they are linked, denote a heterocyclic group, the units of formula (2) comprising a cosmetically acceptable anion;

(2) a quaternary polymer comprising recurring units of the formula:

$$\left[\begin{array}{c} R_1 \\ | \\ -N^\oplus - A - N^\oplus - B - \\ | \\ R_2 \end{array} \begin{array}{c} R_3 \\ | \\ \\ | \\ R_4 \end{array}\right]_n \quad 2nX^\ominus$$

in which $R_1$, $R_2$, $R_3$ and $R_4$ independently represent an aliphatic, alicyclic or araliphatic radical containing at most 20 carbon atoms or a lower hydroxyaliphatic radical, or $R_1$ and $R_2$, and $R_3$ and $R_4$, together or separately, form, together with the nitrogen atoms to which they are linked, a heterocyclic ring which optionally contains a second heteroatom other than nitrogen, or $R_1$, $R_2$, $R_3$ and $R_4$ independently represent a group of the formula:

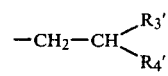

R′3 denoting hydrogen or lower alkyl and R′4 denoting —CN,

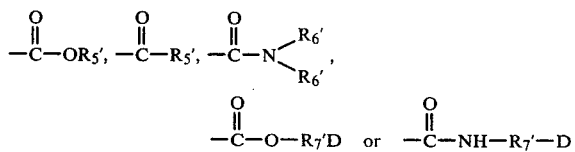

where R′5 denotes lower alkyl, R′6 denotes hydrogen or lower alkyl, R′7 denotes alkylene and D denotes a quaternary ammonium group, and A and B independently represent a hydrocarbon group which can be linear or branched, and saturated or unsaturated and can contain, interposed in the main chain, one or more aromatic rings or one or more groups —CH2—Y—CH2 in which Y denotes —O—, —S—, —SO—, —SO2—, —S—S—,

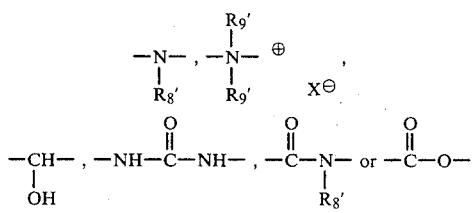

in which R'$_8$ denotes hydrogen or lower alkyl and R'$_9$ denotes lower alkyl, or A and R$_1$ and R$_3$, together with the two nitrogen atoms to which they are linked, form a piperazine ring, and B can also denote

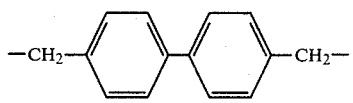

and X$^-$ is a mineral or organic acid anion or

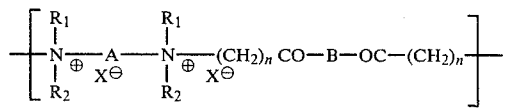

in which A denotes a linear or branched, saturated or unsaturated alkylene or hydroxyalkylene radical, B denotes (a) a radical of the formula —O—Z—O, where Z denotes a linear or branched hydrocarbon radical or a group of the formula:

—[CH$_2$—CH$_2$—O]$_x$—CH$_2$—CH$_2$— or

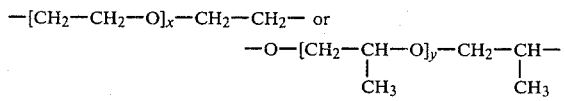

where x and y independently denote an integer from 1 to 4 or, in a mixture of compounds, any number from 1 to 4;

(b) a radical of a bis-secondary diamine;

(c) a radical of a bis-primary diamine of the formula:

—NH—Y—NH— where Y denotes a linear or branched hydrocarbon radical or the divalent radical —CH$_2$—CH$_2$—S—S—CH$_2$—CH$_2$—; or (d) a ureylene group of the formula —NH—CO—NH—, R$_1$ denotes an alkyl radical having from 1 to 4 carbon atoms, R$_2$ denotes a linear or branched hydrocarbon radical containing from 1 to 12 carbon atoms, such that R$_2$ can also denote a plurality of methylene groups linked to one another and form with A, if A denotes an ethylene radical, and with the two nitrogen atoms, a divalent radical of the formula:

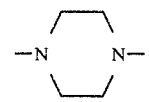

X$^-$ denotes a halide and n denotes the number 1 or an integer from 3 to 10;

said anionic and said cationic polymers present in an amount from about 0.01 to 10% relative to the total weight of the composition; and at least one anionic surface active agent.

23. A composition according to claim 22 which also contains at least one non-ionic surface-active agent.

24. Process for the treatment of keratin material comprising the steps of applying to hair a composition comprising at least one anionic polymer containing at least one of a sulfonic acid, carboxylic acid and phosphoric acid unit, said anionic polymer having a molecular weight of from about 500 to 5 million, and at least one cationic polymer in a solvent medium, said anionic and cationic polymers each being present in an amount of from about 0.01 to about 10% relative to the total weight of the composition, said composition being applied at a pH at which the combination of anionic polymer and cationic polymer does not precipitate, and subsequently, without intermediate rinsing, modifying the pH on the hair to cause the combination of anionic polymer and cationic polymer to precipitate onto said material and subsequently rinsing said material thereby to produce a conditioning effect on the hair.

25. Process according to claim 24 in which the composition is first prepared by adding a solvent to a lyophilizate of the combination of anionic and cationic polymers.

26. Process for the treatment of keratin fibres, which comprises applying to hair a first composition containing a cationic polymer and a reducing agent and in a second stage, applying a neutralizing composition containing an anionic polymer said anionic polymer containing at least one of a sulfonic acid, carboxylic acid and phosphoric acid unit having a molecular weight of from about 500 to 5 million and being present in an amount of from about 0.01 to 10% by weight relative to the weight of said neutralizing composition thereby to straighten or curl the hair.

27. Process for the treatment of keratin material comprising the steps of first applying to hair a first composition containing an effective amount of a cationic polymer in solution, subsequently applying to the hair a second composition containing an effective amount of an anionic polymer containing at least one of a sulfonic acid, carboxylic acid and phosphoric acid unit and having a molecular weight of from about 500 to 5 million, and rinsing said material thereby to produce a conditioning effect on the hair.

28. Process according to claim 27 in which at least one of the compositions also contains a surface-active agent present in an amount from about 0.1 to 70% by weight relative to the total weight of said compositions.

29. Process according to claim 27 in which the first composition is at a pH which does not cause the precipitation of the cationic polymer and the second composition is at a pH such that after application it causes the precipitation of the combination of the polymers onto the keratin materials.

* * * * *